(12) United States Patent
Armour et al.

(10) Patent No.: US 10,827,786 B2
(45) Date of Patent: Nov. 10, 2020

(54) APPARATUS, SYSTEM, AND METHOD FOR REDUCING HEAD OR NECK TRAUMA

(71) Applicant: Armour Technologies, Inc., Swarthmore, PA (US)

(72) Inventors: Andrew W. Armour, Swarthmore, PA (US); Philbin McCleary, Swarthmore, PA (US); Brady White, Mount Laurel, NJ (US)

(73) Assignee: Armour Technologies, Inc., Swarthmore, PA (US)

( * ) Notice: Subject to any disclaimer, the term of this patent is extended or adjusted under 35 U.S.C. 154(b) by 45 days.

(21) Appl. No.: 16/221,830

(22) Filed: Dec. 17, 2018

(65) Prior Publication Data

US 2019/0116896 A1    Apr. 25, 2019

Related U.S. Application Data

(63) Continuation of application No. 15/031,897, filed as application No. PCT/US2014/062139 on Oct. 24, 2014, now Pat. No. 10,188,159.
(Continued)

(51) Int. Cl.
*A61N 1/04*      (2006.01)
*A41D 13/05*      (2006.01)
(Continued)

(52) U.S. Cl.
CPC .......... *A41D 13/0512* (2013.01); *A61F 5/055* (2013.01); *A61N 1/0452* (2013.01);
(Continued)

(58) Field of Classification Search
USPC ...................................................... 607/115
See application file for complete search history.

(56) References Cited

U.S. PATENT DOCUMENTS 3,212,496 A    10/1965   Preston
3,765,412 A    10/1973   Ommaya et al.
(Continued)

FOREIGN PATENT DOCUMENTS

CA          2822642 A1    2/2014
WO     2007146703 A2    12/2007
(Continued)

OTHER PUBLICATIONS

International Preliminary Report on Patentability for International Application No. PCT/US2014/062139, dated Apr. 26, 2016—8 pages.
(Continued)

*Primary Examiner* — Nicole F Lavert
(74) *Attorney, Agent, or Firm* — RatnerPrestia

(57) ABSTRACT

Apparatus, systems, and methods are provided for the reduction of head or neck trauma in a living being by mitigating the acceleration experienced by the head, relative to the torso, during a change in motion; for example, creating a neck support that provides improved extension, compression, rotation, and bending properties to the neck in order to control the acceleration experienced by the head. The apparatus can be configured to create a neck support in which acceleration of the head, relative to the torso, is reduced with minimal structure, discomfort, and other potential downsides to the user of the apparatus.

35 Claims, 45 Drawing Sheets

Related U.S. Application Data

(60) Provisional application No. 61/895,500, filed on Oct. 25, 2013.

(51) Int. Cl.
*A61F 5/055* (2006.01)
*A63B 71/08* (2006.01)
*A63B 71/12* (2006.01)
*A63B 71/06* (2006.01)
*A63B 102/14* (2015.01)

(52) U.S. Cl.
CPC ........ *A63B 71/081* (2013.01); *A63B 71/1291* (2013.01); *A63B 2071/0625* (2013.01); *A63B 2102/14* (2015.10); *A63B 2207/02* (2013.01); *A63B 2209/08* (2013.01); *A63B 2209/10* (2013.01); *A63B 2213/004* (2013.01); *A63B 2220/20* (2013.01); *A63B 2220/40* (2013.01); *A63B 2220/51* (2013.01); *A63B 2225/50* (2013.01); *A63B 2230/06* (2013.01); *A63B 2230/20* (2013.01); *A63B 2230/202* (2013.01); *A63B 2230/207* (2013.01); *A63B 2230/30* (2013.01); *A63B 2230/42* (2013.01); *A63B 2230/75* (2013.01); *A63B 2243/007* (2013.01); *A63B 2243/0025* (2013.01); *A63B 2243/0037* (2013.01)

(56) References Cited

U.S. PATENT DOCUMENTS

| | | | |
|---|---|---|---|
| 3,900,896 | A | 8/1975 | Ackerman |
| 4,333,179 | A | 6/1982 | Laurita |
| 4,595,010 | A | 6/1986 | Radke |
| 4,686,710 | A | 8/1987 | Marston et al. |
| 5,562,707 | A | 10/1996 | Prochazka et al. |
| 5,566,290 | A | 10/1996 | Silverbrook |
| 6,058,517 | A | 5/2000 | Hartunian |
| 7,144,375 | B2 | 12/2006 | Kosuda |
| 7,498,276 | B2 | 3/2009 | Wagner et al. |
| 7,844,340 | B2 | 11/2010 | Pawlowicz |
| 7,846,117 | B2 | 12/2010 | Leatt et al. |
| 8,679,047 | B2 | 3/2014 | Holt et al. |
| 2003/0028072 | A1 | 2/2003 | Fischell et al. |
| 2004/0255368 | A1 | 12/2004 | Baker |
| 2006/0173510 | A1 | 8/2006 | Besio et al. |
| 2006/0234572 | A1 | 10/2006 | Wagner et al. |
| 2009/0064396 | A1 | 3/2009 | Ghajar |
| 2010/0204628 | A1* | 8/2010 | Ghajar .............. A61F 5/055 602/18 |
| 2012/0094789 | A1 | 4/2012 | Lammer et al. |
| 2012/0226330 | A1 | 9/2012 | Kolen et al. |
| 2013/0205480 | A1 | 8/2013 | Nagely |
| 2013/0239310 | A1 | 9/2013 | Flug |
| 2013/0281759 | A1* | 10/2013 | Hagedorn ............ A61B 5/0482 600/13 |

FOREIGN PATENT DOCUMENTS

| | | |
|---|---|---|
| WO | 2009053946 A2 | 4/2009 |
| WO | 2012054262 A1 | 4/2012 |

OTHER PUBLICATIONS

International Search Report and Written Opinion for International Application No. PCT/US2014/062139, dated Jan. 21, 2015—11 pages.

Entire patent prosecution history of U.S. Appl. No. 15/031,897, filed Apr. 25, 2016, entitled, "Apparatus, System, and Method for Reducing Head or Neck Trauma," now U.S. Pat. No. 10,188,159, issued Jan. 29, 2019.

\* cited by examiner

| 1 | *Desired Use* |
|---|---|
| 2 | Activity/Sport |
| 3 | *User Characteristics* |
| 4 | Name |
| 5 | Age |
| 6 | Gender |
| 7 | Size |
| 8 | Height |
| 9 | Weight |
| 10 | Neck Girth |
| 11 | Neck Length |
| 12 | Neck Muscle Strength |
| 13 | *Sensor Characteristics* |
| 14 | Sampling Rate |
| 15 | *Muscles to be Stimulated* |
| 16 | Trapezius |
| 17 | Sternocleidomastoid |
| 18 | Anterior Scalene |
| 19 | Medius Scalene |
| 20 | Posterior Scalene |
| 21 | Splenius Capitis |
| 22 | Semisinalis Capitis |
| 23 | Levator Scapulae |
| 24 | *Electrode Settings* |
| 25 | Mode |
| 26 | Frequency |
| 27 | Duration |
| 28 | Intensity |
| 29 | User Feedback |
| 30 | Saved Settings |

FIG 38

APPARATUS, SYSTEM, AND METHOD FOR REDUCING HEAD OR NECK TRAUMA

CROSS REFERENCE TO RELATED APPLICATION

This patent application is a U.S. Continuation Patent Application of U.S. application Ser. No. 15/031,897, filed Apr. 25, 2016 (now U.S. Pat. No. 10,188,159, issued Jan. 29, 2019), which is a U.S. National Phase Patent Application of PCT Application No. PCT/US2014/062139, published as WO 2015/061663 and filed Oct. 24, 2014, which claims priority to U.S. Provisional Application No. 61/895,500 entitled "NECK SUPPORTING APPARATUS, SYSTEM, AND METHOD OF USING THE SAME," filed on Oct. 25, 2013, the contents of each application are incorporated herein by reference in their entirety for all purposes.

FIELD OF THE INVENTION

This invention relates generally to an apparatus, system, and method for the reduction of trauma to the head and/or neck of a living being, and more specifically to the apparatuses, systems, and methods which create a neck support in order to reduce head acceleration.

BACKGROUND OF THE INVENTION

Concussion is a mild traumatic brain injury (MTBI) caused by a jostling of the brain in the intracranial space. Concussion can be caused both by direct impact to the head and by movement to the body resulting in jostling of the brain. Linear and angular/rotational brain accelerations are the two variables to consider in head injury since most head injuries will involve both linear and angular forces. The kinetic energy is half of the mass multiplied by the squared velocity; therefore, the velocity has a large impact when considering the biophysical aspect of a concussion. When a concussion occurs, there are high strain forces on the midbrain, and cerebral blood flow decreases significantly after injury. Excessive amounts of a neurotransmitter, glutamate, are released in the body and in turn, cause neurons to fire excessively. This results in an imbalance of ions across the cell membrane, affecting action potentials. Current head and neck protection are effective in skull and cervical injuries, but there remains a need for protection to reduce or prevent harmful lateral and rotational forces on the brain.

Other injuries to the neck, including neck strain or sprain, whiplash, other injuries due to neck hyperextension or hyper flexion, and overuse of muscles, may also require preventative or restorative support to the neck, head, and/or back. For instance, stress injuries occur during daily tasks such as sitting at a computer, where incorrect posture is common, and exercising, when improper form places undue stress on the neck muscles. A device is needed that will not impede any and all activities desired by the user while reducing excessive force or strain on the musculature. Recent findings indicate a correlation between neck strength and concussion incidence. As neck strength increases so does the ability of the neck to counteract a force applied to the head. However, in many cases, athletes do not see an impact coming and thus cannot prepare for impact. When the athlete does not see the impact coming, neck strength becomes less relevant as the muscles are not engaged, and concussion incidence is higher.

Many attempts to address these problems are designed to work in conjunction with a helmet. For example, U.S. Pat. No. 6,058,517 discloses a foam-like neck collar to be fastened around the neck to reduce and cushion extreme motions of the neck for lessening the occurrence of or eliminating neck injuries. Further, U.S. Pat. No. 3,900,896 discloses a neck brace for athletes to be secured to the base of a helmet as well as shoulder pads which functions to limit flexion and extension of the neck. Additionally, U.S. Pat. No. 7,846,117 discloses a neck brace to be used in conjunction with a helmet that inhibits excessive neck movement during impact, yet otherwise allows a high degree of motion.

U.S. Pat. No. 3,765,412 discloses an inflatable cervical collar functioning to prevent whiplash-like head and neck injury. The collar is connected to a compressed natural gas source for inflation upon impact; therefore, it is not suitable for wear in most circumstances.

U.S. Pat. No. 4,686,710 A discloses a sports neck guard that protects hockey players from lacerations in the wearer's throat caused by a hockey stick blade or a skate blade. The neck guards protect the player from dangerous blows to the throat, but the neck guard does not protect the wearer from concussions that occur due to neck movement.

Similar to U.S. Pat. No. 4,686,710A is U.S. Pat. No. 4,333,179 that provides air-inflated padding to serve as a throat protector but does not protect the carotid artery nor does it protect the neck to avoid mild traumatic brain injury.

U.S. Pat. No. 7,144,375 discloses a pulsimeter which utilizes a wrist watch as a user interface to detect a pulse wave and has a pulse wave sensor to output a pulse wave signal. The pulsimeter has a control program through a computer device to allow an accurate calculation of pulse rate despite body motion components that overlap pulse wave components. Disclosed in U.S. Pat. No. 3,212,496 A is a molecular physiological monitoring system that measure electrocardiogram, respiration rate, and heart rate and transmits the data with or without the use of wires. The miniature transducer contains electronic circuits that can be implanted subcutaneously or externally on the human body.

Research published in Computers in Biology and Medicine reveals an interactive graphical user interface that analyzes human cardiac monophasic action potentials. The graphical user interface coupled with an algorithm analyzes data from both swine and human hearts can detect ischemic and assess appropriate pharmaceutical interventions.

Polar (www.polar.com) has developed and commercialized many different heart rate monitors and sport watches. These systems have transmitters that measure human physiology, GPS data, speed, distance, etc. and calculate and communicate this information to a user interface such as a watch or smart phone through Bluetooth and other wireless means.

There are also disclosures for adhesive supports such as U.S. Pat. No. D265,828 and other similar kinesiology tapes that function to increase healing and provide support with no appreciable thickness on the skin. This support, however, is quite limited and largely for rehabilitation purposes.

U.S. Patent Application Publication No. US 2013/0239310 A1, now abandoned, relates to an anti-concussion compression device meant to protect the neck and spine.

U.S. Pat. No. 3,765,412 relates to an inflatable cervical collar meant to protect the head and neck from whiplash-like injuries.

EP 2637927 A1 relates to a device to be worn around the neck that will compress the veins and restrict brain venous drainage to reduce energy absorption.

U.S. Patent No. CA 2,822,642 A1 relates to an apparatus for preventing neck, spinal cord injury, and concussion comprising a helmet and body harness that may limit cervical rotation, lateral bending, flexion, and extension.

PCT Patent No. WO 2009053946 A2 relates to the method to process composite structures with adaptive stiffness integrating shear thickening fluids. U.S. Pat. No. 7,498,276 B2 relates to the use of shear thickening fluids in body armor and protective devices.

U.S. Patent Application Publication No. US 2012/0094789 A1, now abandoned, relates to a system and method of using shear thickening materials in sports products.

U.S. Pat. No. 8,679,047 B2 relates to an athletic tape or protective athletic sleeve using shear thickening fluid.

U.S. Pat. No. 4,595,010 relates to an electrical muscle stimulator used to stimulate one or more muscles through one or more electrodes attached to the body.

U.S. Pat. No. 7,844,340 B2 relates to a device and method for performing transcutaneous electrical stimulation on a human patient.

U.S. Patent Application Publication No. US 2006/0173510 A1 (now U.S. Pat. No. 8,190,248, issued May 29, 2012), relates to a medical device utilizing electrical stimulation to prevent and/or treat neurological disorders.

U.S. Pat. No. 5,566,290 A relates to a garment that reduces the risk of bone fracture due to impact forces that may utilize a dilatant material for energy dissipation.

U.S. Patent Application Publication No. U.S. 2006/0234572 A1, now abandoned, details a method of containment for shear thickening fluids using polymer composites.

PCT Patent No. WO 2007146703 A2 details a process used to coat a shear thickening fluid onto a material.

U.S. Pat. No. 5,562,707 describes an electrical stimulation garment with a joint movement sensor that aids a user in gripping objects.

To any extent needed to explain the foregoing technologies, the disclosures of the foregoing publications are incorporated herein by reference. As stated above, most current head and neck protective devices provide significant protection from skull and cervical injuries, but lack substantial ability to manage jostling of the brain especially in sports such as soccer and basketball where concussion incidence is still high despite limited contact. There is, therefore, a need for a wearable device that manages jostling of the brain while remaining suitable for use during activities including non-contact, non-helmeted sports.

SUMMARY OF THE INVENTION

According to one embodiment, this invention provides an apparatus for engaging or supporting the head of a living being, the apparatus having a portion configured to be positioned over the neck's sternocleidomastoid muscle, the apparatus being configured to allow a full range of neck positions, while restricting the neck's speed of motion, thereby increasing the time necessary for the head to reach an extreme position in the neck's full range of motion. The apparatus may also have a portion configured to be positioned over the upper trapezius muscles. The apparatus may also have a portion configured to be positioned over the occipital cup muscles. The apparatus may also have a portion configured to be positioned over the scalene muscles. The apparatus may also have a portion configured to be positioned over the frontal trapezius muscle. The apparatus may also have a portion configured to be positioned over the upper trapezius muscles. The apparatus may also be configured to require a greater force for the head to reach the extreme position in the neck's range of motion. The apparatus may be comprised of an elastic material, a viscoelastic material or both elastic and viscoelastic materials. The apparatus may be comprised of an electroactive material or a ferrofluid material. It may also comprise a sensor and have an adhesive positioned to releasably attach the apparatus to the neck or have a high friction material positioned for contact with the neck.

According to another embodiment, this invention provides an apparatus for supporting the head of a user whereby at least a portion of the apparatus is configured to be positioned over the user's neck, the apparatus comprising elastic and viscoelastic materials configured to allow a complete range of physical neck extension, flexion, lateral bending, and rotation positions while simultaneously increasing the force required by the user to reach said neck positions and to increase the time necessary for the head to reach said neck positions. The apparatus may have an increased force required by the user between 1 and 10 pounds force greater than the force required without the neck apparatus. The apparatus may have an increased time necessary for the head to reach said neck positions approximately 100% greater than the time required without the neck apparatus. The apparatus may be configured to wrap entirely around the neck. The apparatus may be configured for attachment to the posterior portion of the neck by engaging a position corresponding to the posterior sternocleidomastoid muscle. The apparatus may be configured for attachment to the posterior portion of the neck by engaging a position corresponding to the posterior portion of the frontal trapezius muscle. The apparatus may comprise a spring formed from an elastomer, a polymer, a rubber, graphene, and/or a metal. The apparatus may have a spring comprised of nitinol.

According to yet another embodiment, this invention provides an apparatus configured for supporting the neck of a user whereby at least a portion of the apparatus is configured to be. frictionally engaged with the user's neck skin, the apparatus comprising elastic and viscoelastic materials configured to stretch and compress in parallel with the underlying skin and to allow a complete range of physical neck extension, flexion, lateral bending, and rotation positions while simultaneously increasing the force required by the user to reach said neck positions and increasing the time necessary for the neck to reach said neck positions. The apparatus may also be comprised of a rubber or elastomer, wherein the frictional engagement to the skin is made with the rubber or elastomer. The apparatus may also have a polished surface, wherein the frictional engagement to the skin is made with the polished surface. The apparatus may also have a temporary adhesive, wherein the frictional engagement to the skin is made with the temporary adhesive. The apparatus may also have a permanent adhesive, wherein the frictional engagement to the skin is made with the permanent adhesive.

According to yet another embodiment, this invention provides an apparatus for supporting the head of a living being, the apparatus comprising a structure that completely encircles the neck of the living being.

According to yet another embodiment, this invention provides an apparatus for supporting the head of a living being, the apparatus comprising means for allowing a full range of neck positions while restricting the neck's speed of motion and increasing the time necessary for the head to reach the extreme position in the neck's full range of motion when the means is positioned over the neck's sternocleidomastoid muscle.

According to yet another embodiment, this invention provides a system for supporting the head of a user, the system comprising an apparatus including at least one sensor and having a structure configured to allow a full range of neck positions, while restricting the neck's speed of motion, thereby increasing the time necessary for the head to reach the extreme position in the neck's full range of motion; and a user interface, wherein the sensor of the apparatus is in communication with the user interface. The system may have a sensor used to control an electroactive material in order to restrict the neck's speed of motion. The sensor may also be used to control a ferrofluid material in order to restrict the neck's speed of motion. According to yet another embodiment, this invention provides a method for supporting the head of a living being, the method comprising the steps of 1) positioning a support over the sternocleidomastoid muscle of a neck of the living being; 2) arranging the support to allow a full range of neck positions; 3) restricting the neck's speed of motion through the full range of neck positions; and 4) increasing the time necessary for the head to reach the extreme position in the neck's full range of motion. The method further comprising reducing the incidence of concussions. The method further comprising limiting the support to extend up to 60 degrees with a forward extension of the neck. The method further comprising limiting the support to flex up to 50 degrees with a backward flexion of the neck. The method further comprising limiting the support to laterally bend up to 45 degrees with a left or right bending of the neck. The method further comprising limiting the support to rotate up to 80 degrees with a left or right rotation of the neck. The method further comprising configuring the support to increase the force and time necessary for the neck to reach the ranges of motion.

According to yet another embodiment, this invention provides a method for stimulating the musculature of the neck in such a way that the muscles contract. The method comprising an electrical control system and electrodes will cause the neck muscles to act as dampers to lessen the force of an impact.

According to yet another embodiment, this invention provides a method for stimulating the musculature of the neck in such a way that the muscles contract. The method comprising an electrical control system and electrodes will cause the neck muscles to constrict along with the upper torso. This will cause the projected whiplash of the head to be distributed over a much larger area minimizing the acceleration of the head will slightly increasing the acceleration of the entire body.

According to yet another embodiment, this invention provides an apparatus for reducing trauma in the head or neck of a living being caused by acceleration of the head relative to the torso of the living being within a range of motion, the apparatus comprising a support configured to engage at least one of the head, neck, and shoulder of the living being without limiting the range of motion of the head and neck relative to the torso and a damper associated with the support and configured to mitigate the speed or acceleration of the head relative to the torso, wherein the damper provides a lower resistance to the motion when the speed or acceleration of the head relative to the torso is lower and a higher resistance to the motion when the speed or acceleration of the head relative to the torso is higher. The apparatus may further comprise a support having at least one head engagement portion positioned to engage the head and at least one neck engagement portion coupled to the head engagement portion and positioned to engage at least one of the neck and shoulder, and the damper coupled to the head engagement portion of the support and the neck engagement portion of the support. The apparatus may also comprise a support which includes an adhesive configured to temporarily attach the support to a portion of at least one of the head, neck, and shoulder. The apparatus may also comprise a support which includes a high friction material configured to contact a portion of at least one of the head, neck, and shoulder. The apparatus may also comprise a support configured to wrap entirely around the neck. The apparatus may also comprise a support configured to be attached to the posterior portion of the neck along a posterior sternocleidomastoid muscle. The apparatus may also comprise a support which is configured to be attached to the posterior portion of the neck along a posterior portion of the frontal trapezius muscle. The apparatus may also comprise a support including a spring made from elastomer, polymer, rubber, or metal, the spring being configured to attach the support to the posterior portion of the neck. The apparatus may also comprise a spring which is formed from nitinol. The apparatus may also comprise a high friction material that is a rubber or elastomer. The apparatus may also comprise a damper which is configured to elongate, compress, rotate, or bend so as to resist the motion. The apparatus may also be configured where the elongation, compression, rotation, or bending of the damper generates a force adequate to resist the motion. The apparatus may also comprise a damper which is configured to provide a lower resistance to the motion when the position of the head relative to the torso is closer to a center of the range of motion and a higher resistance to the motion when the position of the head relative to the torso is closer to extents of the range of motion. The apparatus may also be configured wherein the head engagement portion is positioned to be placed in close proximity to the base of the skull of the living being. The apparatus may also be configured wherein the neck engagement portion is positioned to be in close proximity to spinal vertebrae C3 of the living being.

The apparatus may also comprise a damper including a mechanical damper, wherein the damper is configured to provide the support with the resistance to the motion. The apparatus may also be configured with a mechanical damper comprising a dashpot associated with the support. The apparatus may also be configured with a mechanical damper comprising a viscoelastic material associated with the support. The apparatus may also be configured with a mechanical damper comprising a shear thickening fluid associated with the support. The apparatus may also be configured with a mechanical damper comprising an oil or grease associated with the support. The apparatus may also be configured with a mechanical damper comprising an elastic material associated with the support. The apparatus may further comprise a mechanical damper being configured to generate an opposing force proportional to a speed of elongation, compression, rotation, or bending of the support.

The apparatus may also comprise a damper including a physiological damper, wherein the apparatus further comprises at least one electrode associated with the support and an actuator coupled to actuate the electrode in response to a sensed position, speed or acceleration of the head, wherein the electrode is positioned to stimulate a muscle of the living being to increase the resistance to the motion provided by the muscle in response to the sensed position, speed or acceleration of the head. The apparatus may further comprise at least one sensor positioned to sense at least one of position, speed, or acceleration of the head or neck. The apparatus may further comprise at least one sensor positioned to sense at least one of position, speed, or acceleration of elongation, compression, rotation, or bending of the support. The apparatus may also comprise an electronic controller and a power source. The apparatus may also comprise a battery. The apparatus may also comprise at least one electrode being configured to stimulate a muscle in at least one of the neck and shoulder. The apparatus may also be configured to stimulate a muscle being selected from a group consisting of the splenius capitis, levator scapulae, sternocleidomastoideus, scalenus, and trapezius. The physiological damper may also be configured to create opposing force proportional to a speed of elongation, compression, rotation, or bending of the support.

The apparatus may further comprise a damper including an electromechanical damper, wherein the damper is configured to provide the support with the lower resistance to the motion when the speed or acceleration of the head relative to the torso is lower and to provide the support with the higher resistance to the motion when the speed or acceleration of the head relative to the torso is higher, wherein the apparatus further comprises an electrically activated material associated with the support and an actuator coupled to actuate the electrically activated material in response to a sensed position, speed or acceleration of the head, wherein the electrically activated material is positioned to increase resistance to the motion provided by the support in response to the sensed position, speed or acceleration of the head. The apparatus may further comprise at least one sensor configured to sense at least one of position, speed, or acceleration of the head or neck. The apparatus may further comprise at least one sensor configured to sense at least one of position, speed, or acceleration of elongation, compression, rotation, or bending of the support. The apparatus may further comprise a control system. The apparatus may also be configured where the electrically activated material comprises an electroactive polymer. The apparatus may also be configured where the electrically activated material comprises a ferrofluid. The apparatus may also be configured where the electrically activated material comprises a shape memory alloy. The apparatus may also comprise an electromechanical damper being configured to create an opposing force proportional to a speed of elongation, compression, rotation, or bending of the support.

According to yet another embodiment, this invention provides an apparatus for reducing trauma in the head or neck of a living being caused by acceleration of the head relative to the torso of the living being within a range of motion, the apparatus comprising a support configured to engage at least one of the head, neck, and shoulder without limiting the range of motion of the head or neck relative to the torso, the support having at least one head engagement portion positioned to engage the head and at least one neck engagement portion coupled to the head engagement portion and positioned to engage at least one of the neck and shoulder, and means coupled to the head engagement portion of the support and the neck engagement portion of the support for mitigating the speed or acceleration of the head relative to the torso within the range of motion. The apparatus may be further configured wherein the mitigating means comprises a damper associated with the support and configured to provide a lower resistance to the motion when the speed or acceleration of the head relative to the torso is lower and a higher resistance to the motion when the speed or acceleration of the head relative to the torso is higher. The apparatus may also be configured wherein the mitigating means comprises a damper associated with the support and configured to provide a lower resistance to the motion when the position of the head relative to the torso is closer to a center of the range of motion and a higher resistance to the motion when the position of the head relative to the torso is closer to extents of the range of motion. According to yet another embodiment, this invention provides a system for reducing trauma in the head or neck of a living being caused by acceleration of the head relative to the torso of the living being within a range of motion, the system comprising a support engaging at least one of the head, neck, and shoulder of the living being without limiting the range of motion of the head or neck relative to the torso, a sensor in electrical communication with the system, and a damper associated with the support and configured to mitigate the speed or acceleration of the head relative to the torso. The system may be configured wherein the damper is configured to provide a lower resistance to the motion when the speed or acceleration of the head relative to the torso is lower and a higher resistance to the motion when the speed or acceleration of the head relative to the torso is higher. The system may also be configured wherein the damper is configured to provide a lower resistance to the motion when the position of the head relative to the torso is closer to a center of the range of motion and a higher resistance to the motion when the position of the head relative to the torso is closer to extents of the range of motion. The system may comprise a sensor which is configured to sense at least one of the position, speed, and acceleration of the head or neck. The sensor may be configured to sense at least one of the position, speed, and acceleration of elongation, compression, rotation, or bending of the support. The system may also comprise a control system, wherein the control system may further comprise a battery. The system may also comprise a control system which is configured to actuate the damper in response to a communication from the sensor in order to increase the time needed for the head to move through the range of motion. The system may further comprise a user interface, wherein the user interface may be wired or wirelessly connected to the control system and configured to alert the living being to a speed or acceleration of the head relative to the torso. The system may also be configured for electrical communication with an external database, wherein the external database may be wired or wirelessly connected to the control system and stores the speed or acceleration of the head relative to the torso. The system may further comprise a damper including a mechanical damper, wherein the damper provides the support with the lower resistance to the motion when the speed or acceleration of the head relative to the torso is lower and provides the support with the higher resistance to the motion when the speed or acceleration of the head relative to the torso is higher. The system may further comprise a damper including a physiological damper, wherein the system further comprises at least one electrode associated with the support and an actuator coupled to actuate the electrode in response to a sensed position, speed or acceleration of the head, wherein the electrode is positioned to stimulate a muscle of the living being to increase the resistance to the motion provided by the muscle in response to the sensed position, speed or acceleration of the head. The system may further comprise a damper including an electromechanical damper, wherein the damper provides the support with the lower resistance to the motion when the speed or acceleration of the head relative to the torso is lower and provides the support with the higher resistance to the motion when the speed or acceleration of the head relative to the torso is higher, wherein the system further comprises an electrically activated material associated with the support and an actuator coupled to actuate the electrically activated material in response to a sensed position, speed or acceleration of the head, wherein the electrically activated material increases resistance to the motion provided by the support in response to the sensed position, speed or acceleration of the head.

According to yet another embodiment, this invention provides a method for reducing trauma in the head or neck of a living being caused by acceleration of the head relative to the torso of the living being within a range of motion, the method comprising steps for engaging a support with at least one of the head, neck, and shoulder without limiting the range of motion of the head or neck relative to the torso, and mitigating the speed at which the head moves relative to the torso and increasing the time needed for the head to move through the range of motion using a damper associated with the support. The method may further comprise the mitigating step being performed at least in part by the damper providing a lower resistance to the motion when the speed or acceleration of the head relative to the torso is lower and a higher resistance to the motion when the speed or acceleration of the head relative to the torso is higher, thereby mitigating the acceleration of the head relative to the torso. The method may further comprise the mitigating step being performed at least in part by the damper providing a lower resistance to the motion when the position of the head relative to the torso is closer to a center of the range of motion and a higher resistance to the motion when the position of the head relative to the torso is closer to extents of the range of motion. The method may further comprise the mitigating step being performed at least in part by a mechanical damper providing the support with the lower resistance to the motion when the speed or acceleration of the head relative to the torso is lower and the higher resistance to the motion when the speed or acceleration of the head relative to the torso is higher. The method may further comprise the mitigating step being performed at least in part by a physiological damper actuating an electrode in response to a sensed position, speed or acceleration of the head, thereby stimulating a muscle of the living being to increase the resistance to the motion provided by the muscle in response to the sensed position, speed or acceleration of the head. The method may further comprise the mitigating step including stimulating a muscle of at least one of the neck and shoulder, whereby the shoulder is raised with respect to the head, effectively shrugging the shoulder. The method may further comprise the mitigating step including stimulating the levator scapulae or trapezius muscles. The method may further comprise the mitigating step including stimulating the muscle of at least one of the neck and shoulder, whereby contraction of the muscle causes the neck to stiffen. The method may further comprise the mitigating step including stimulating the trapezius or sternocleidomastoid muscles. The method may further comprise the mitigating step including stimulating a muscle of at least one of the neck and shoulder opposing the motion, thereby counteracting the motion. The method may further comprise the mitigating step being performed at least in part by an electromechanical damper applying electric current to an electrically activated material in response to a sensed acceleration of the head, thereby increasing the resistance to the motion provided by the support in response to the sensed position, speed or acceleration of the head. The method may further comprise step for sensing a position, speed, or acceleration of the head or neck. The method may further comprise a step for sensing a position, speed, or acceleration of elongation, compression, rotation, or bending of the support. The method may also include a mitigating step further comprising applying the electric current to an electroactive polymer. The method may also include the mitigating step further comprising applying the electric current to a ferrofluid. The method may also include the mitigating step further comprising applying the electric current to a shape memory alloy. The method may further comprise the mitigating step being performed at least in part by creating opposing force proportional to the speed of elongation, compression, rotation, or bending of the support.

According to yet another embodiment, this invention provides a method for reducing trauma in the head or neck of a living being caused by acceleration of the head relative to the torso of the living being within a range of motion, the method comprising the steps of engaging a support with at least one of the head, neck, and shoulder of the living being without limiting the range of motion of the head or neck relative to the torso, sensing a position, speed, or acceleration of the head or neck, and electrically activating a damper coupled to the support to mitigate the speed at which the head moves relative to the torso. The method may further comprise the mitigating step being performed at least in part by the damper providing a lower resistance to the motion when the speed or acceleration of the head relative to the torso is lower and a higher resistance to the motion when the speed or acceleration of the head relative to the torso is higher, thereby mitigating the acceleration of the head relative to the torso. The method may further comprise the mitigating step being performed at least in part by the damper providing a lower resistance to the motion when the position of the head relative to the torso is closer to a center of the range of motion and a higher resistance to the motion when the position of the head relative to the torso is closer to extents of the range of motion. The method may further comprise the mitigating step being performed at least in part by a physiological damper actuating an electrode in response to the sensed position, speed or acceleration of the head, thereby stimulating a muscle of the living being to increase the resistance to the motion provided by the muscle in response to the sensed position, speed or acceleration of the head. The method may further comprise the mitigating step including stimulating a muscle of at least one of the neck and shoulder, whereby the shoulder is raised with respect to the head, effectively shrugging the shoulder. The method may further comprise the mitigating step including stimulating the levator scapulae or trapezius muscles. The method may further comprise the mitigating step including stimulating the muscle of at least one of the neck and shoulder, whereby contraction of the muscle causes the neck to stiffen. The method may further comprise the mitigating step including stimulating the trapezius or sternocleidomastoid muscles. The method may further comprise the mitigating step including stimulating a muscle of at least one of the neck and shoulder opposing the motion, thereby counteracting the motion. The method may further comprise the mitigating step being performed at least in part by an electromechanical damper applying electric current to an electrically activated material in response to the sensed acceleration of the head, thereby increasing the resistance to the motion provided by the support in response to the sensed position, speed or acceleration of the head. The method may also include a step comprising sensing a position, speed, or acceleration of elongation, compression, rotation, or bending of the support. The method may also include the mitigating step further comprising applying the electric current to an electroactive polymer. The method may also include the mitigating step further comprising applying the electric current to a ferrofluid. The method may also include the mitigating step further comprising applying the electric current to a shape memory alloy. The method may also include the mitigating step being performed at least in part by creating opposing force proportional to the speed of elongation, compression, rotation, or bending of the support.

BRIEF DESCRIPTION OF FIGURES

FIG. 38 is a table depicting an embodiment of the external database.

DETAILED DESCRIPTION OF EMBODIMENTS OF THE INVENTION

Figure 1:
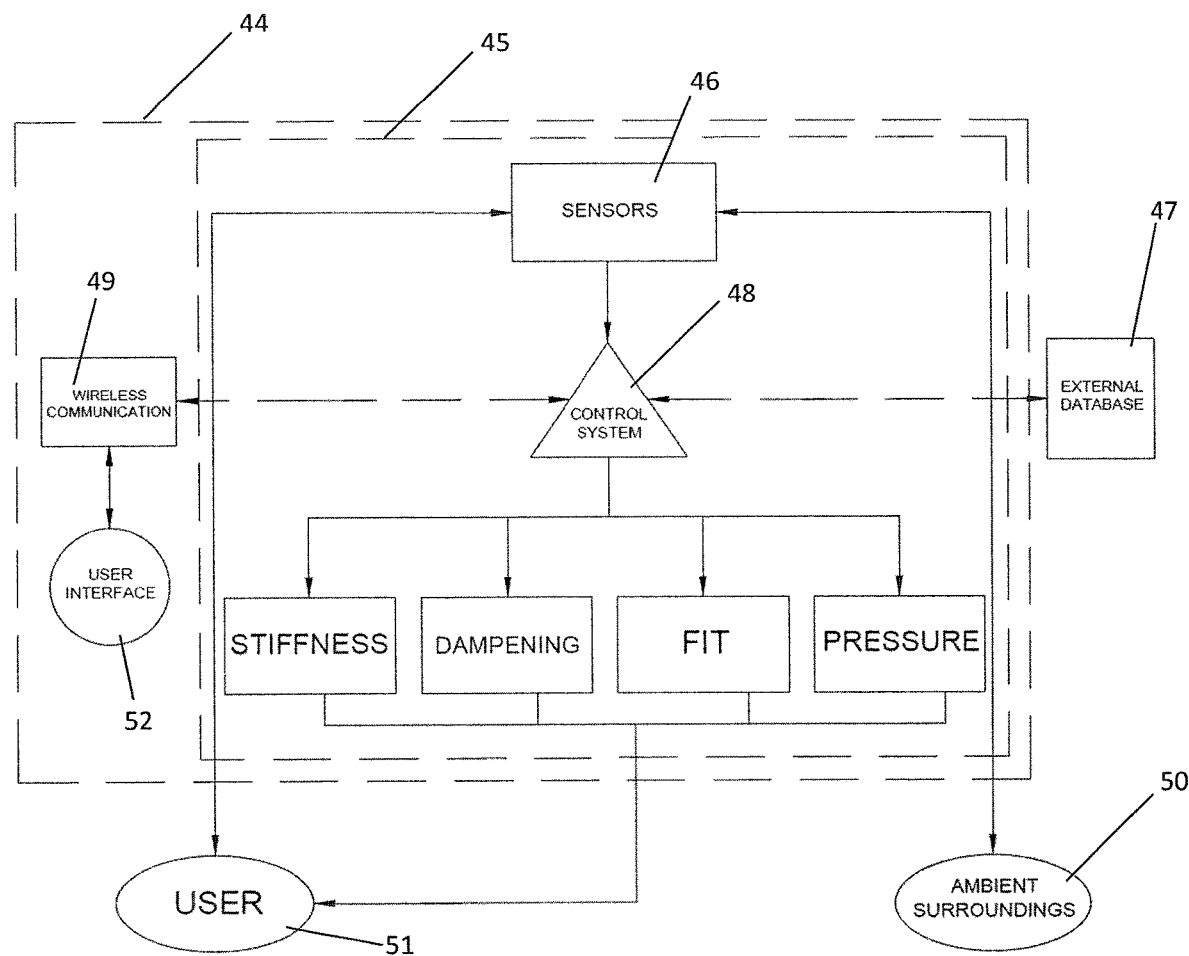
FIG. 1 is a schematic of an embodiment of a neck supporting system according to the invention.

FIG. 1 schematically shows the neck supporting system 44 interacting with a user 51, the ambient surroundings 50, and an external database 47. The neck supporting system 44 is comprised of a neck supporting apparatus 45 and user interface 52, communicating through a wireless communication 49 that may also in fact be wired if this is a more practical solution for the user. Wireless techniques such as Bluetooth, wifi, or other radio waves may be used. The neck supporting system 44 may be passive and structurally support the neck, head, shoulders, and/or back as a mechanical damper or force regulator, or it may be active and embody sensors 46 communicating with active structural materials. These active materials may change in stiffness, such as increasing or decreasing the flexibility of the neck supporting apparatus 45 or cause a change in stiffness of the neck musculature of the user 51. Or the active materials may alter in viscoelasticity (dampening), wherein the structure will slow or absorb or otherwise mitigate or reduce the force of the acceleration or the shock of impact either by virtue of its material composition or by stimulating the neck musculature. Additionally, the active materials may alter in elasticity, size (fit), or they may specifically apply pressure to the jugular veins or arteries in order to increase cranial pressure. The sensors 46 may measure force, acceleration, velocity, displacement, angle, or orientation with respect to gravity. These sensors 46 can measure the kinetic activity of the user 51 and the user's neck, communicate this information to an actuator such as a control system 48 which may consist of a microprocessor and other electronics with the ability to communicate with a user interface 52, or be downloaded to or programmed by an external database 47.

Sensors 46 that measure blood pressure and pulse rate can record or wirelessly broadcast the cardiovascular physiological parameters of the user 51 to provide real time condition status. Other forms of sensors 46 may measure the acceleration, displacement, or force applied to the user 51. The sensors 46 may also communicate with the control system 48 in order to activate portions of the neck supporting system 44. If a force from the user's surroundings 50 is registered by the sensors 46, the control system 48 may activate changes in the material, causing stiffness, dampening, fit, and pressure changes as an electromechanical damper or force regulator, or it may engage electrodes or other means of altering the position, stiffness, and dampening of the user's neck musculature as a physiological damper or force regulator.

Furthermore, the sensors 46 may control the properties of the neck apparatus 45 so as to dynamically change its properties during use. For example, using electroactive polymers, elastomers, piezoelectric, magnetostrictive, ferrofluids, shape memory alloys, dielectric elastomers, or any other intelligent material that change in stiffness upon application of an electric field, magnetic field, temperature, moisture, pH, or other external stimuli could instantaneously respond to a control system 48 output as a function of the sensor 46 inputs to the control system 48. Electroactive fibers are flexible, light weight, and have low fracture tolerance and pliability.

Additionally, electroactive polymers can take on any shape and can exhibit a large displacement when responding to electrical stimuli. Electroactive materials can undergo a large amount of deformation while withstanding a large amount of force. Elastomers can sustain high strains and can be modeled as a capacitor with the ability to change its capacitance when voltage is applied. This allows the polymer to expand in area while compressing in thickness because of the electric field. Since the polymers have high mechanical energy density, there are no major constraints when the materials are operated in air. They do, however, require high activation fields that are close to the breakdown level. An alternative material could be an ionic electroactive polymer, which can be achieved at lower voltages. These materials favor a wet environment, which is a factor to consider since the athletes may be sweating. Electroactive polymers are capable of sustaining large amounts of force and can act as sensors as well. For example, a threshold can be established such that when the user's 51 neck undergoes a force close to this threshold, a signal can be sent to the neck supporting apparatus 45 and can have the material correct the placement of the head and neck.

Figure 2:
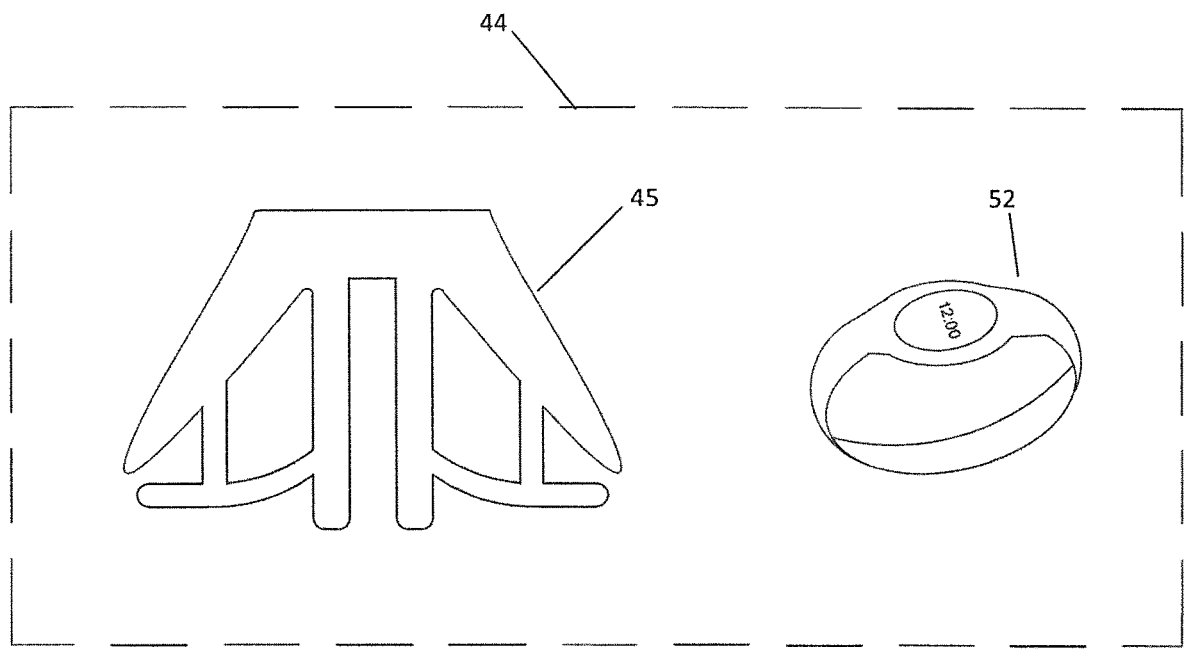
FIG. 2 depicts an embodiment of a neck supporting apparatus and a user interface as part of the neck supporting system.

In FIG. 2, the neck supporting system 44 embodiment may include a neck supporting apparatus 45 and a user interface 52. The neck supporting apparatus 45 may be composed of materials that provide both flexibility and rigidity. Most importantly, the neck supporting apparatus 45 should not limit the user's neck freedom of motion, but rather help to control the allowable acceleration during bending of the neck. The top portion is used to support the sternocleidomastoid muscle (SCM) for rotational and lateral movement while the two middle extensions are used to provide support to the superior trapezius and assist in both flexion and extension. The neck supporting apparatus 45 can send signals to the user interface 52, which could be a watch to tell the user parameters such as heart rate and blood pressure. It may also tell the user such information as how much force or acceleration is experienced by the surrounding muscles in the neck.

Figure 3:
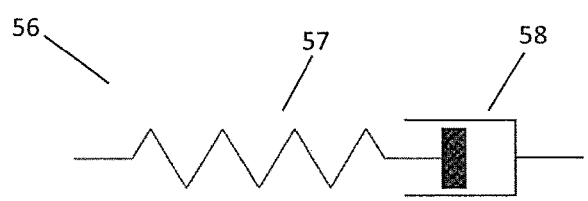
FIG. 3 is a schematic model of a viscoelastic material (Maxwell).
Figure 4:
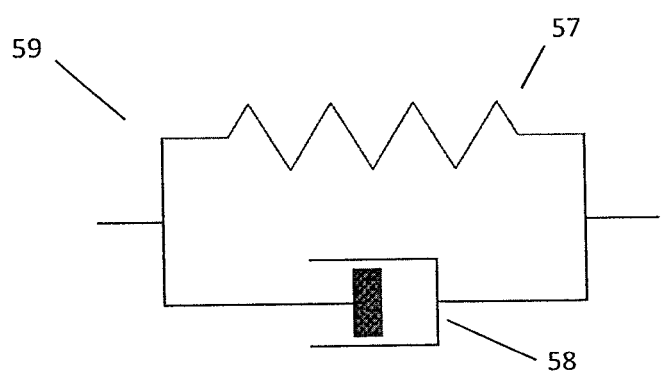
FIG. 4 is a schematic model of a viscoelastic material (Voigt).
Figure 5:
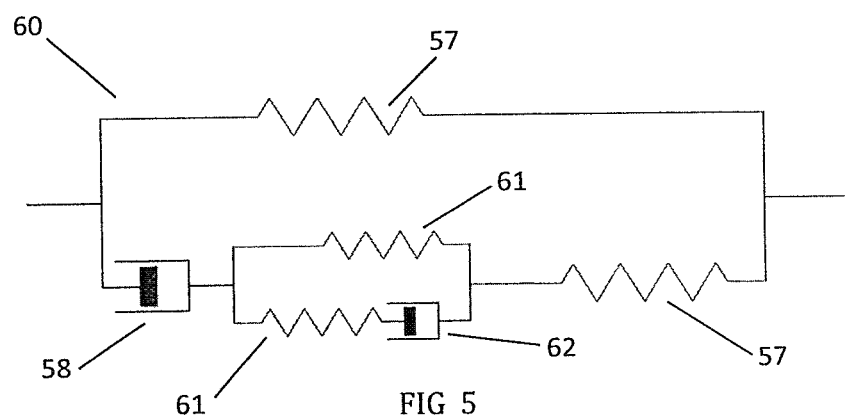
FIG. 5 is a schematic model of a viscoelastic material (Daniel).

In FIGS. 3-5, the neck supporting apparatus may have mechanical properties including those of, springs in series 57 and in parallel 61, and dashpots in series 58 and in parallel 62, which define its elasticity and dampening. In FIG. 3-5, the viscoelastic properties of the soft tissues are represented by three different models, which are Maxwell's model 56, FIG. 3, Voigt's model 59, FIG. 4, and Daniel's model 60, FIG. 5. Soft tissues will experience different properties, such as hysteresis during loading and unloading, stress relaxation at a constant strain, creep at a constant stress, and strain rate dependence. These viscoelastic properties can be displayed by circuit diagrams where the strains add in series and stresses add in parallel. FIG. 3 represents a simple linear viscoelastic model, known as Maxwell's model and assumes a uniform distribution of stress. In FIG. 3, an elastic spring 57 is in series with a viscous damper or a dashpot 58. The elastic stress will depend on strain from the spring 57, and the viscous stress will depend on the strain-rate from the dashpot 58. Since the spring 57 and dashpot 58 are in series, the total strain rate is the spring strain rate added to the dashpot strain rate. Under a constant strain, the stresses experience exponential decay. In this model, the force will exponentially decay; however, the deformation will remain constant as time increases. In FIG. 4, the elastic spring 57 is in parallel with the viscous dashpot 58. This is known as the Voigt model, and since the dashpot 58 and spring 57 are in parallel, the total stress is the spring stress added to the dashpot stress. This model assumes a uniform distribution of strain. The model cannot be instantaneously deformed to a given strain, but in creep, the stress is constant. FIG. 5 is Daniel's model, which utilizes both Maxwell's model and Voigt's model in that there is a dashpot 62 and spring 61 in series, and this system is in parallel with another spring 61. That entire component is in series with another dashpot 58 and a spring 57, which is all in parallel with a different spring 57.

Figure 6:
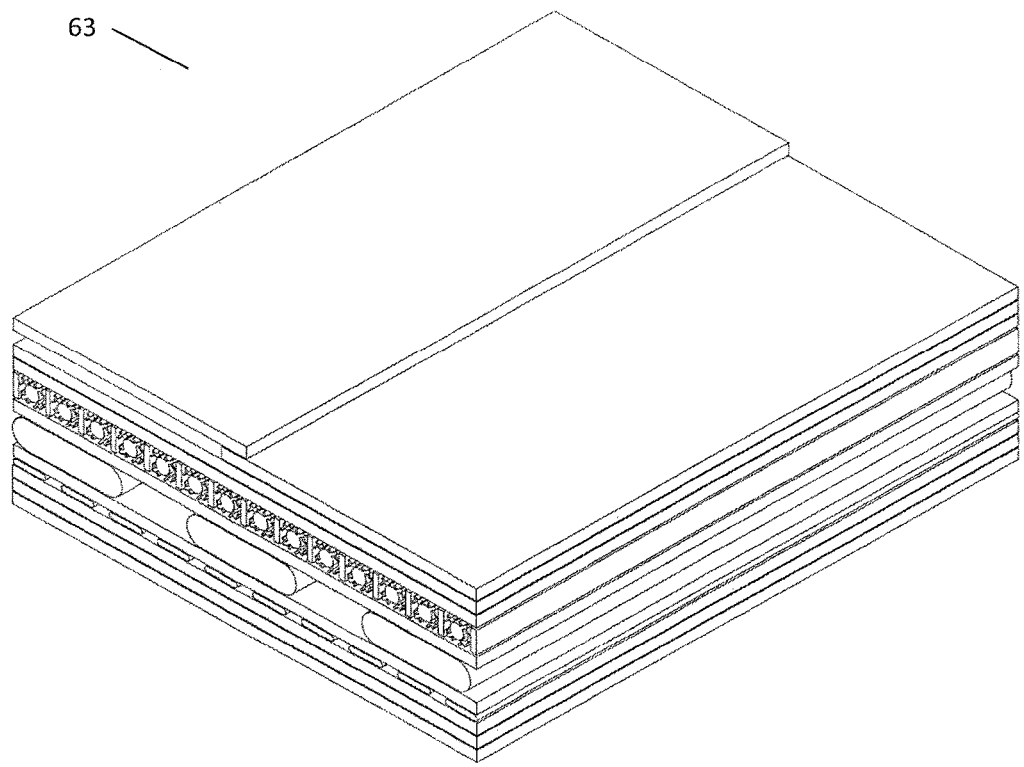
FIG. 6 depicts an embodiment of the neck supporting apparatus layers.
Figure 6A:
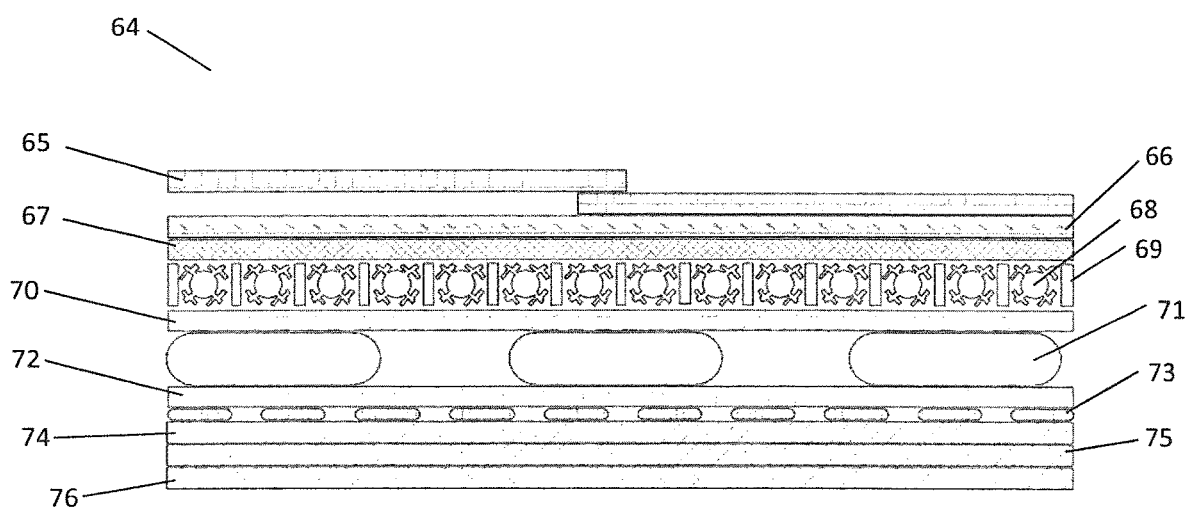
FIG. 6a depicts a cross section of the layers in the neck supporting apparatus of FIG. 6.

In FIGS. 6 and 6*a*, the neck supporting apparatus embodiment 63 and 64 may consist of multiple layers to provide the functionality to the user. An inner screen layer 76 to minimize trauma to the skin and hair during removal, a wicking mesh layer 75 to wick sweat away from the body, an adhesive layer 74 to adhere to the skin, a sensor layer 73, a wicking layer 72 to facilitate removal of the adhesive with an adhesive remover fluid, venous compression members 71, a viscoelastic material 70, flexural stiffening members 69 interspersed with dampened elongation members 68, a control system with microelectronics 67, an elastic fabric 66, and fastening means 65. These layers can be combined to form layers with multiple functionalities and can be arranged in many different ways.

Alternatively, the dampening elongation members 68, could act as miniature (even nanoscale) dashpots that allow complete freedom of motion in elongation, compression, bending, and/or rotation when the changes in position over time or speed over time are smaller, but when changes in position over time or speed over time are greater, the dashpots provide an opposing force to the motion. The dashpots can be pneumatic, hydraulic, or electrically active in nature. They can be self-contained, or act in combination with the layer that they are contained within. One example of this would be to combine the dampening elongation members 68 with a high viscosity oil or grease so that elongation of the neck support apparatus 63 requires the dampening elongation members 68 to slide between the high viscosity oil or grease and the surrounding embodiment. The boundary layer interface with each dampening elongation member 68 will result in increasing resistance of motion due to the friction or drag as the change in position over time or speed over time increases. This is explained by the dynamic shear viscosity equations and also described as Couette flow. The dampening elongation members 68 could also have surface features that would enhance their frictional engagement with a high viscosity fluid or viscoelastic material. For example, tiny hairs, bumps, recesses, ridges, or other disturbances could increase the surface area, thereby increasing the magnitude of the opposing forces created by the dashpots. The dampening elongation members 68, could also be configured as thin sheets or films that are formed in alternating layers with each layer consisting of a boundary layer interface.

To provide the most resistance possible while allowing for the most flexible neck supporting apparatus 63 the flexural stiffening members 69 would have the largest moment of inertia possible in all directions that are being used to resist motion. The ideal structure would be thin elastic cylindrical rods which in great numbers would allow for rotation and motion in all directions while providing significant resistance. This would be similar to muscle utilizing muscle fibers for strength and flexibility.

The neck support apparatus 63 may utilize various types of adhesives for securing the apparatus to the neck, shoulders, head, and/or back. One of the preferred adhesives is a silicone adhesive under the trademark of 3M Kind Removal tape. Removal of the adhesive may be facilitated by using a polysiloxane (silicone) fluid such as Dow 360 medical fluid which is soluble with the silicone adhesive. The neck apparatus 63 could have wicks that allow the silicone medical fluid to wick into communication with the adhesive so that the entire adhesive layer 74 may be easily removed from the skin. Alternatively, bladder containing medical fluid could be contained within the neck apparatus 63 with small valves that can be opened to allow the fluid to come in contact with the adhesive. An alternate method to adhere the neck support apparatus 63 to the user may be to utilize a base layer of a high friction material.

Figure 7:
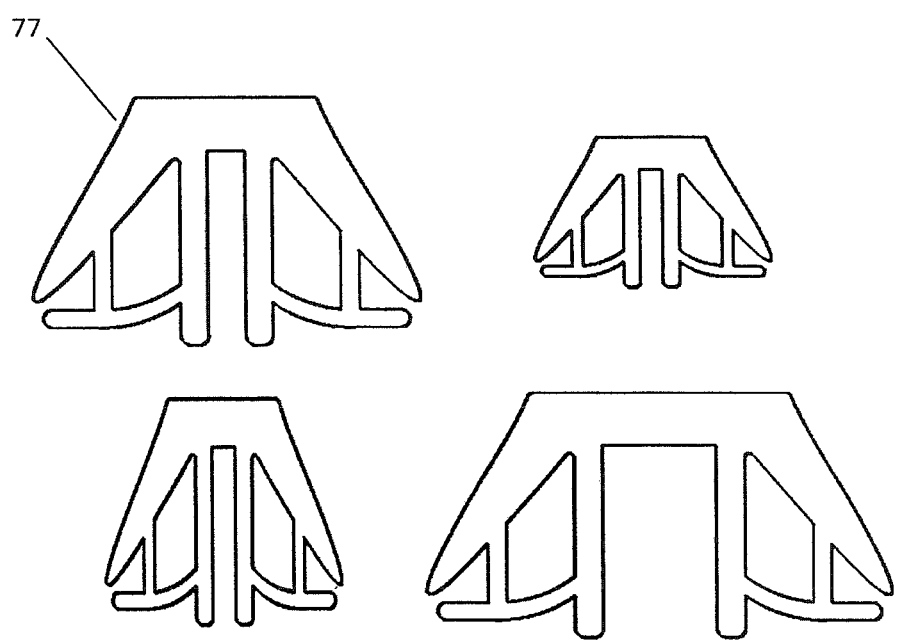
FIG. 7 depicts various sized embodiments of the neck supporting apparatus shown in FIG. 2.

In FIG. 7, the neck supporting apparatus 77 is shown in multiple sizes. The neck support apparatus may be custom sized for a particular person based on measurements or may be pre-made in a range of discrete sizes based on these measurements. In the event of custom sizing, the user will be fitted using measurements that may include but are not limited to, neck circumference, shoulder width, neck length, and measurements determining the length and location of the back of neck hairline for adhesive placement purposes.

Figure 8:
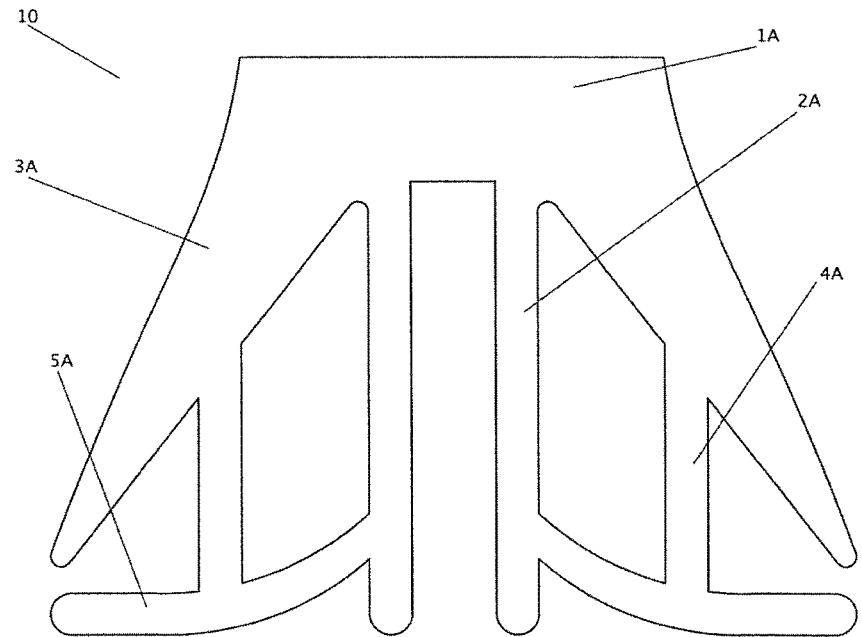
FIG. 8 depicts an embodiment of the neck supporting apparatus support with reinforcement projections that radiate from the base of the head toward the shoulders and base of the neck.

In FIG. 8, the neck supporting apparatus 10 may work in conjunction with the major muscles of the neck associated with extension, flexion, rotation, and lateral motion, namely: sternocleidomastoid, upper trapezius, and the scalene muscles. The sternocleidomastoid functions to rotate the head to the opposite side and it is also involved in flexing the neck and extending the head. It is innervated by the accessory nerve. Scalene muscles include three pairs of muscles: the scalenus anterior, scalenus medius, and scalenus posterior that are innervated by spinal nerves. The superior region of the trapezius is also supplied by the accessory nerve and stabilizes and moves the scapula. The neck supporting apparatus 10 may be of little appreciable thickness lying against the neck and generally soft so as to prevent potential harm to others upon collision and making it acceptable for use in non-contact, non-padded sports such as soccer and basketball. Additionally, the constituting materials and their properties may function to dampen or absorb forces to the head by increasing the time taken for the head to reach the extreme in the neck's range of motion; i.e. flexion, extension, rotation, and lateral motion, thereby inherently reducing the acceleration experienced by the brain. It is also contemplated that the neck supporting apparatus 10 may serve as a neck strengthening training tool to build up the neck muscles separate from its function as a supporting structure.

The neck supporting apparatus 10 may have any number of the following structural properties: rigidity, flexibility, extensibility, inextensibility, elasticity, inelasticity, viscoelasticity, and viscosity. That is, the device may dampen forces to the head employing any of the aforementioned properties. Further, the neck supporting apparatus 10 may be of a single damping material or a composite structure. This includes but is not limited to a single material, such as viscoelastic silicone rubber or graphene, or a composite structure of a laminated elastomer wherein the lamination provides additional structure and alters the properties of the solitary elastomer.

Figure 8A:
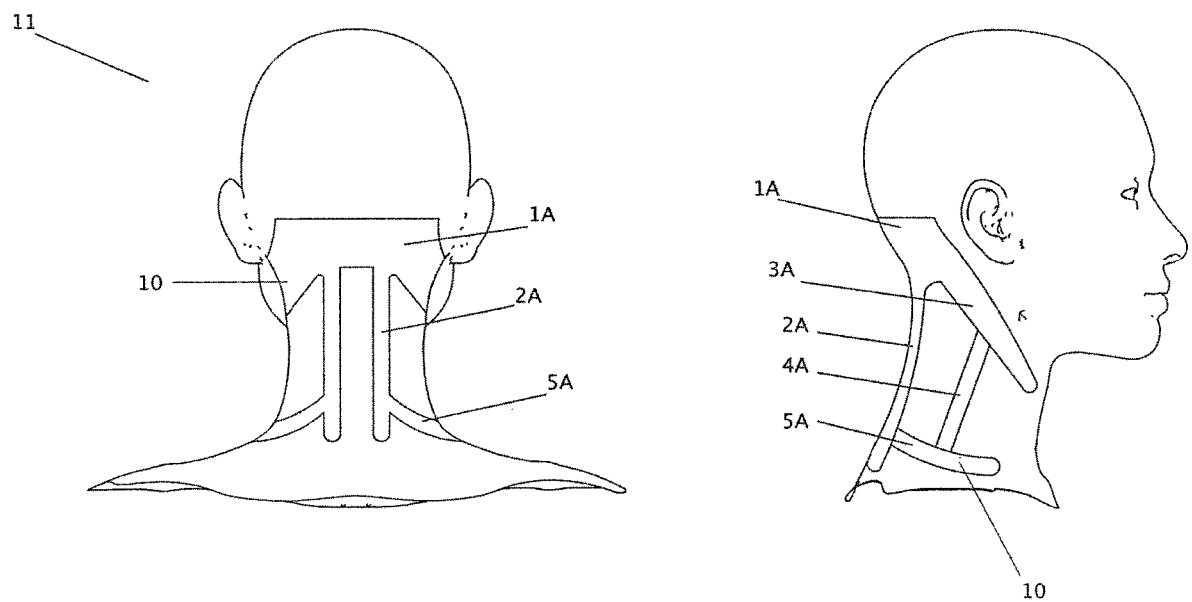
FIG. 8a depicts the embodiment of FIG. 8 as it would appear on a human neck both from a rear and profile perspective.
Figure 8B:
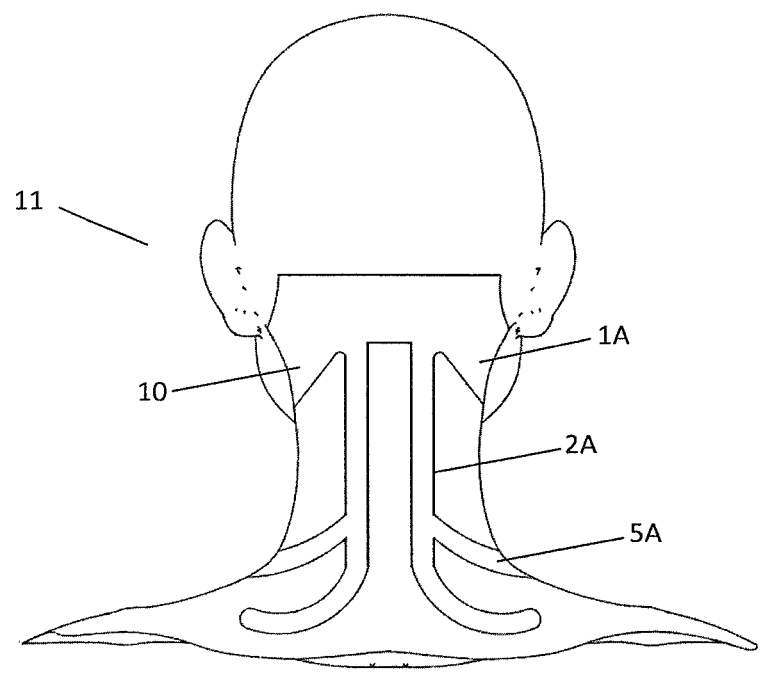
FIG. 8b depicts an embodiment of FIG. 8 with extended trapezius supports as it would appear on a human neck from the rear.

The embodiment depicted in FIG. 8 displays a neck supporting apparatus 10 comprised of a material with structural properties on the spectrum from rigid to flexible, providing some flexibility as well as rigidity. The trapezius supports 2A, which may extend as long as necessary from the skull down to the back, may provide reinforcement for flexion and extension motions, the SCM supports 3A may provide reinforcement for rotational and lateral motion, and the scalene supports 4A provide further reinforcement for lateral motion. The base for the scalene supports 5A, which may sit at the base of the neck or lay down the back or curve around to the front, serves as an anchor to the scalene supports 4A. The top portion 1A of the neck supporting apparatus 10 sits at the base of the head over the occipital bone of the skull. This embodiment 10 can be seen on a human neck from both a rear and profile perspective 11 in FIG. 8a. A similar embodiment may be seen in FIG. 8b, where the trapezius supports 2A extend down to the back and curve out to engage with lower fibers of the trapezius muscle.

Accordingly, embodiments of this invention may include a support having one or more head engagement portions and one or more neck engagement portions. Also, embodiments of this invention may optionally include a damper that is coupled, directly or indirectly, to one or more head engagement portions of a support (such as for example top portion 1A) and one or more neck engagement portions of the support (such as for example bottom portions like scalene supports 5A). The damper and/or the support may be configured to elongate, compress, rotate, or bend or otherwise deform so as to allow or resist motion of the head. For example, such elongation, compression, rotation, or bending of the damper or support can generate a force adequate to resist the motion.

Embodiments of an apparatus according to this invention my include structures, such as a damper, that provides a lower resistance to motion, such as motion of the head, when the speed or acceleration of the head relative to the torso is lower and a higher resistance to the motion when the speed or acceleration of the head relative to the torso is higher. In this way, the resistance can be relatively lower at relatively lower accelerations or speeds and relatively higher at relatively higher accelerations or speeds. Also, embodiments of the apparatus of this invention may be configured to provide a lower resistance to motion of the head when the position of the head relative to the torso is closer to a center of the range of motion and a higher resistance to the motion when the position of the head relative to the torso is closer to extents of the range of motion. Also, the apparatus is optionally configured to generate an opposing force proportional to a speed of elongation, compression, rotation, or bending of the apparatus or support. The apparatus can be designed to directly or indirectly contact or engage various anatomies of a living being. For example, it may directly or indirectly engage the head, neck, one or more shoulders, torso, or other anatomies. As one possible example, a head engagement portion of an exemplary apparatus is optionally positioned to be placed in close proximity to the base of the skull of the living being. In another example, a neck engagement portion of the apparatus is optionally positioned to be in close proximity to spinal vertebrae C3 of the living being.

Figure 9:
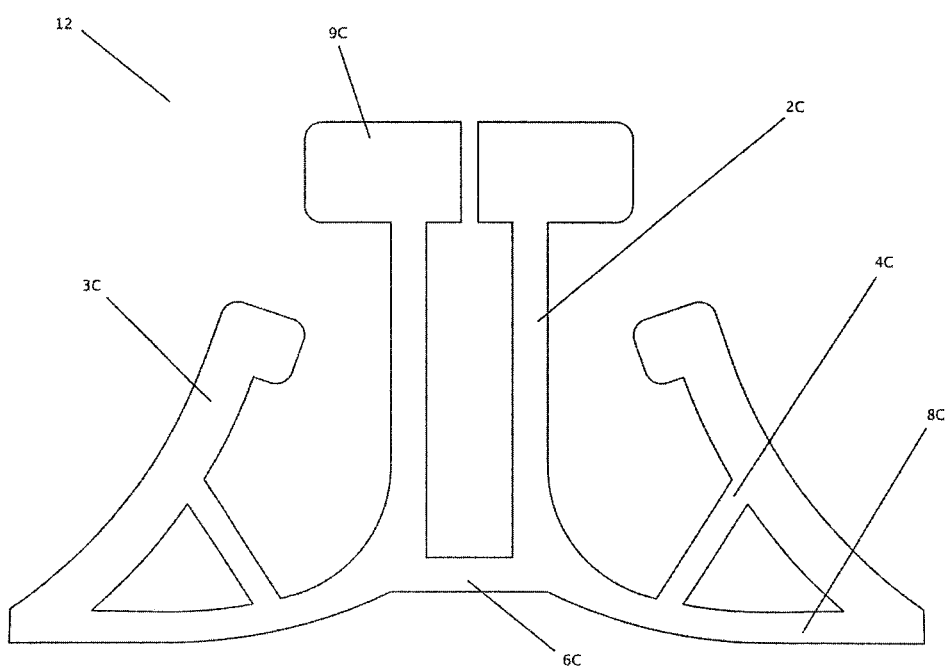
FIG. 9 depicts an embodiment of the neck supporting apparatus with reinforcement projections that radiate from the shoulders and base of the neck towards the head.
Figure 9A:
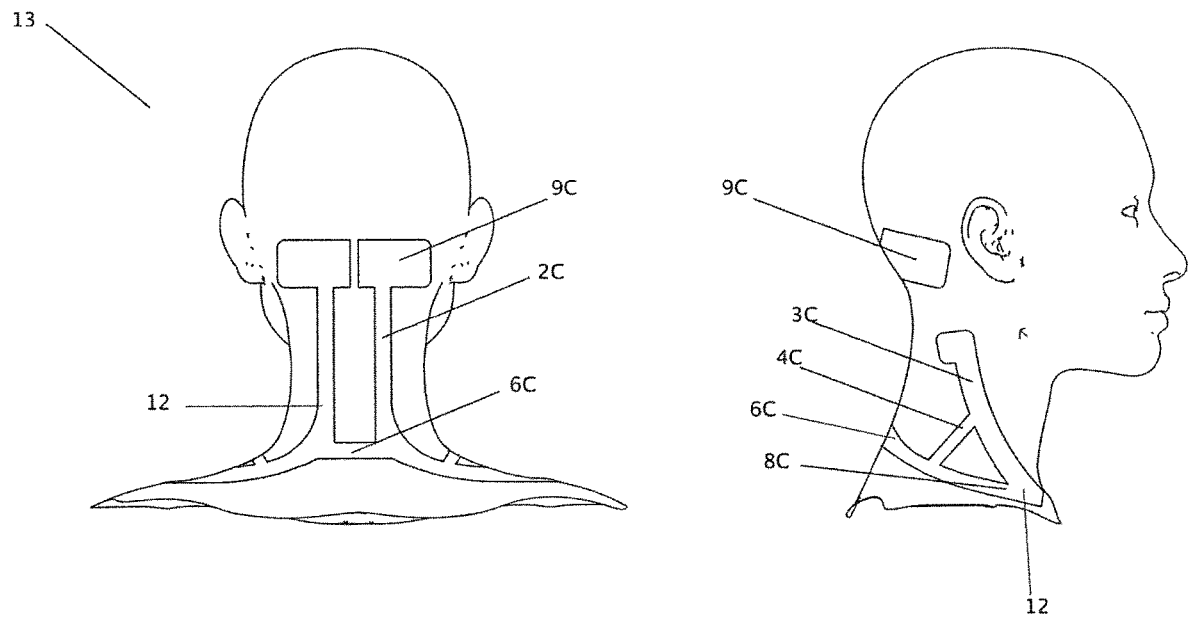
FIG. 9a depicts the embodiment of FIG. 9 as it would appear on a human neck both from a rear and profile perspective.

The embodiment depicted in FIG. 9 displays a neck supporting apparatus 12 comprised of a material with structural properties on the spectrum from extensible to inextensible. This embodiment 12 is based at the shoulders 6C with reinforcements projecting upwards towards the head. The trapezius supports 2C run from the base at the shoulders 6C to the base of the head where each culminates in a separate support 9C. The trapezius supports 2C reinforce the head and neck in flexion and extension motions using damping properties of the aforementioned material. The SCM supports 3C reinforce the head and neck through rotational and lateral motions, and the scalene supports 4C further reinforce the head and neck in lateral motions with the base 8C providing an anchor for both supports 3C, 4C. This embodiment 12 is shown on a human neck 13 in FIG. 9a from both a rear and profile view.

Figure 10:
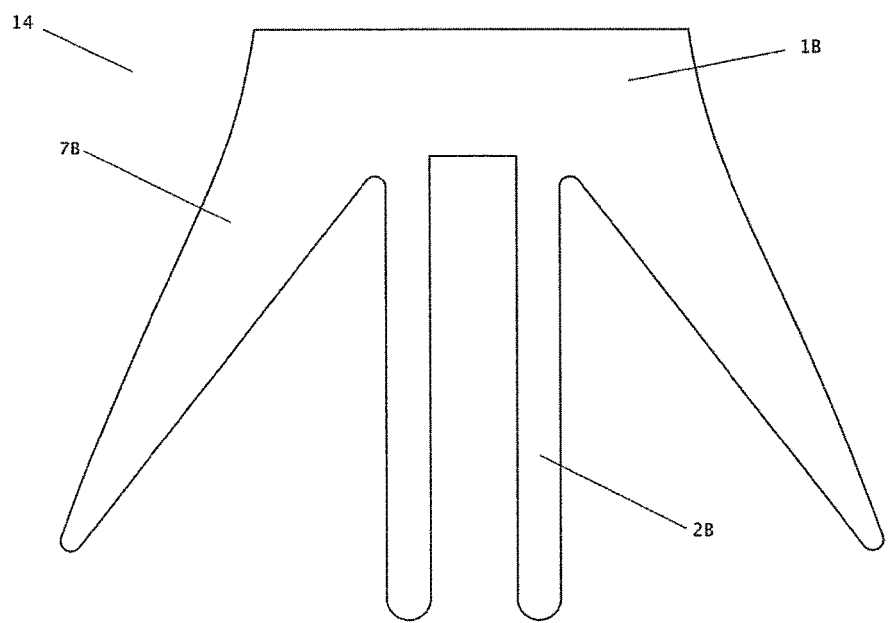
FIG. 10 depicts an embodiment of the neck supporting apparatus with reinforcement projections that radiate from the base of the head toward the shoulders and base of the neck.
Figure 10A:
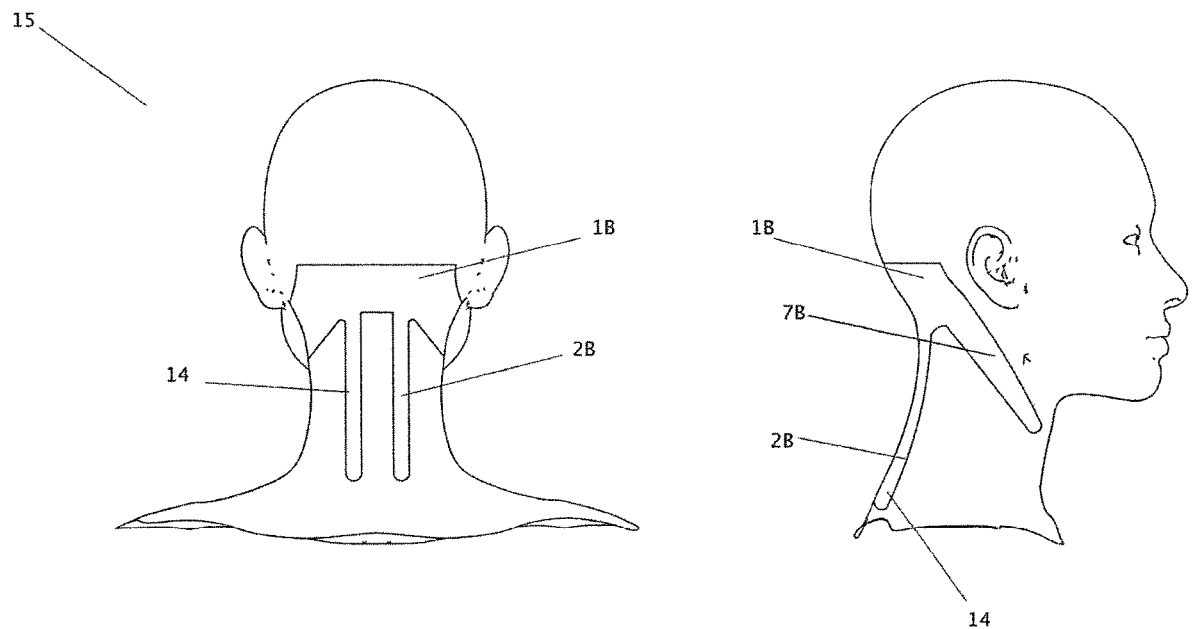
FIG. 10a depicts the embodiment of FIG. 10 as it would appear on a human neck both from a rear and profile perspective.

The embodiment 14 depicted in FIG. 10 displays a neck supporting apparatus 14 comprised of a material with structural properties on the spectrum from elastic to inelastic. This embodiment 14 is based at the bottom of the head over the occipital bone on a with a single head piece IB. The trapezius supports 2B, which may extend downward onto the shoulders and back if necessary, reinforce the head through flexion and extension motions. In this embodiment the support for the SCM and the scalene muscles is combined into one projection 7B for each side of the neck. This projection 7B reinforces the head and neck through rotational and lateral motions. This embodiment 14 is shown on a human neck 14 from both rear and profile perspectives.

Figure 11:
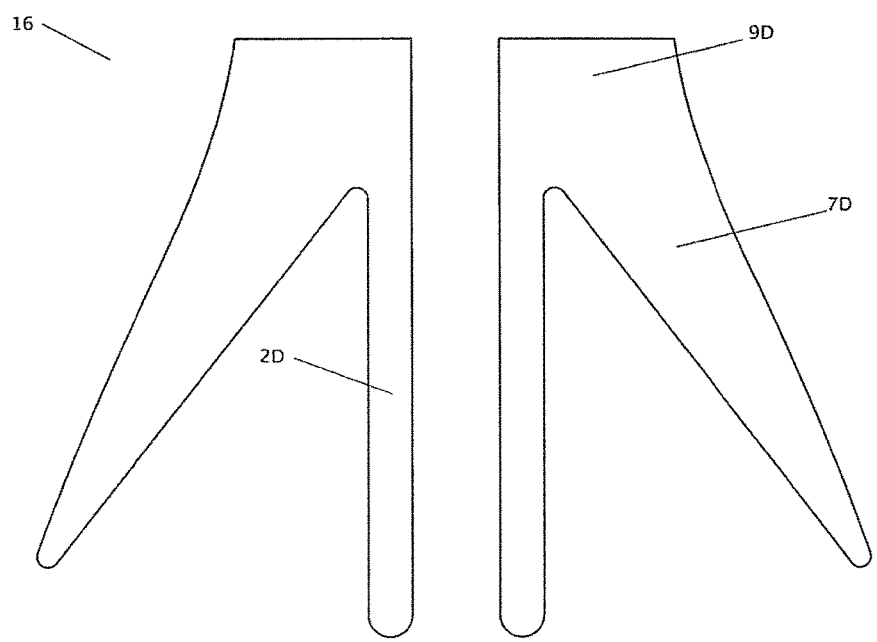
FIG. 11 depicts an embodiment of the neck supporting apparatus with reinforcement projections that radiate from the base of the head toward the shoulders and base of the neck.
Figure 11A:
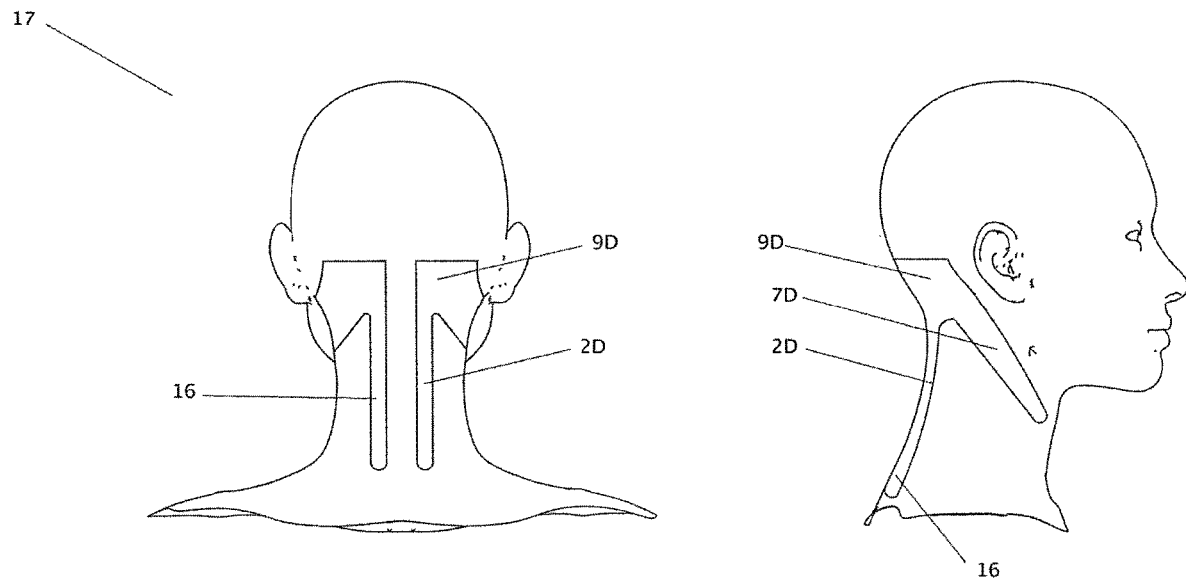
FIG. 11a depicts the embodiment of FIG. 11 as it would appear on a human neck both from a rear and profile perspective.

The embodiment depicted in FIG. 1 displays a neck supporting apparatus 16 comprised of a viscoelastic material, that is, for example, a material having both viscous and elastic properties. This embodiment 16 is based at the bottom of the head over the occipital bone with separate left and right portion of the apparatus. From the separate head supports 9D projects the combined SCM and scalene supports 7D and the trapezius supports 2D. Each of these supports provides damping to forces to the head and neck employing the viscoelastic properties of the material constituting this embodiment 16. The neck supporting apparatus 16 is shown in FIG. 11a as it would appear on a human head and neck 17 from both a profile and rear perspective.

Figure 12:
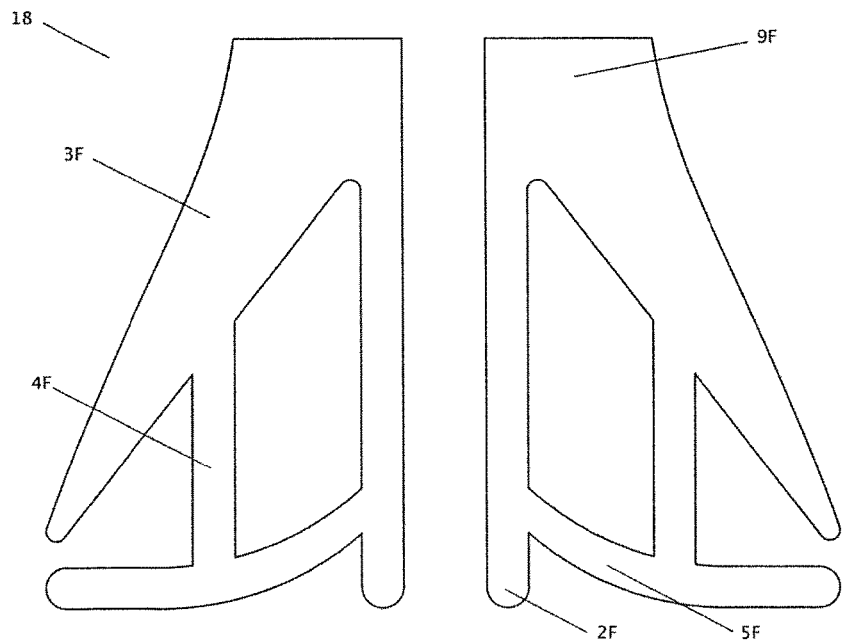
FIG. 12 depicts an embodiment of the neck supporting apparatus with reinforcement projections that radiate from the base of the head toward the shoulders and base of the neck.
Figure 12A:
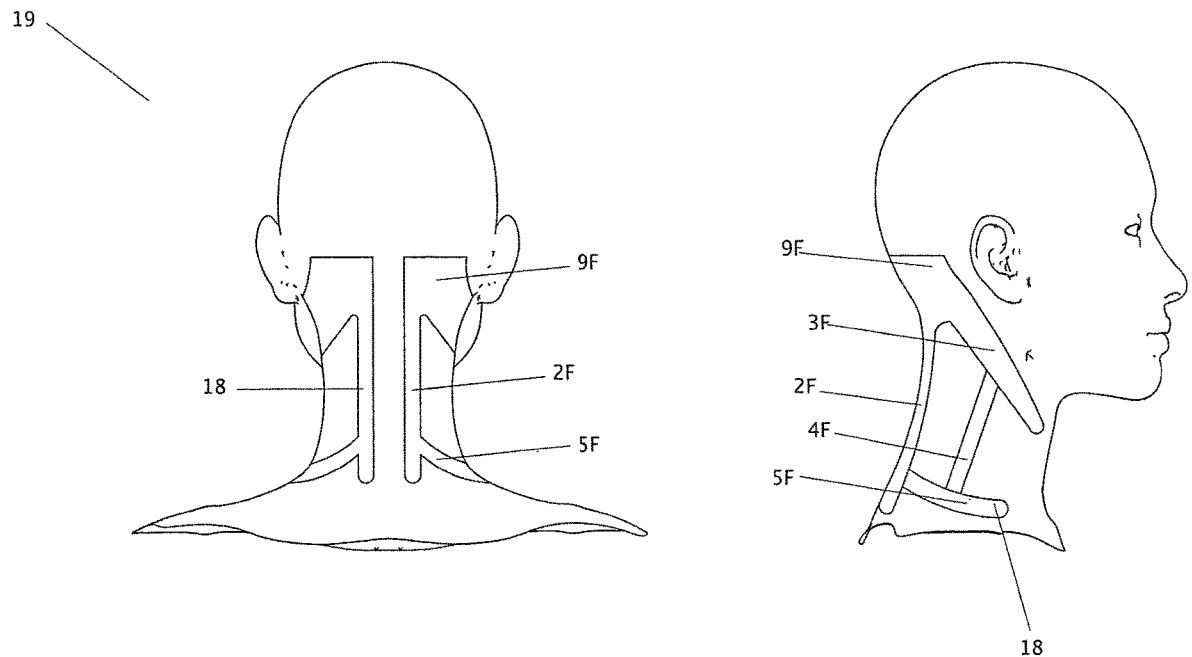
FIG. 12a depicts the embodiment of FIG. 12 as it would appear on a human neck both from a rear and profile perspective.

The embodiment depicted in FIG. 12 displays a neck supporting apparatus 18 comprised of a composite material. Both rigid/flexible materials and extensible/inextensible materials constitute this composite material in proportions and positions best suited for damping forces to the head and neck. This embodiment consists of separate left and right pieces, wherein SCM supports 3F and trapezius supports 2F project from the separate head pieces 9F. Further, the scalene supports 4F project from the SCM supports 3F connecting with the base 5F, which projects from the trapezius 2F. The SCM supports 3F reinforces rotational and lateral motion of the head and neck, the scalene supports 4F further reinforces lateral motion, and the trapezius supports 2F reinforce extension and flexion motion of the head and neck. This embodiment 18 is shown as it would appear on a human neck 19 as shown in FIG. 12a both from a rear and profile perspective.

Figure 13:
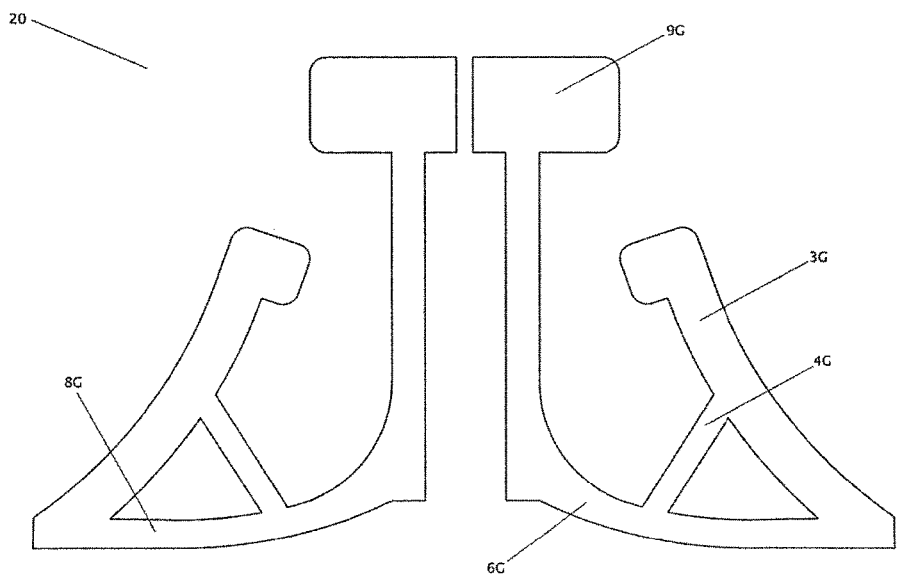
FIG. 13 depicts an embodiment of the neck supporting apparatus with reinforcement projections that radiate from the shoulders and base of the neck toward the head.
Figure 13A:
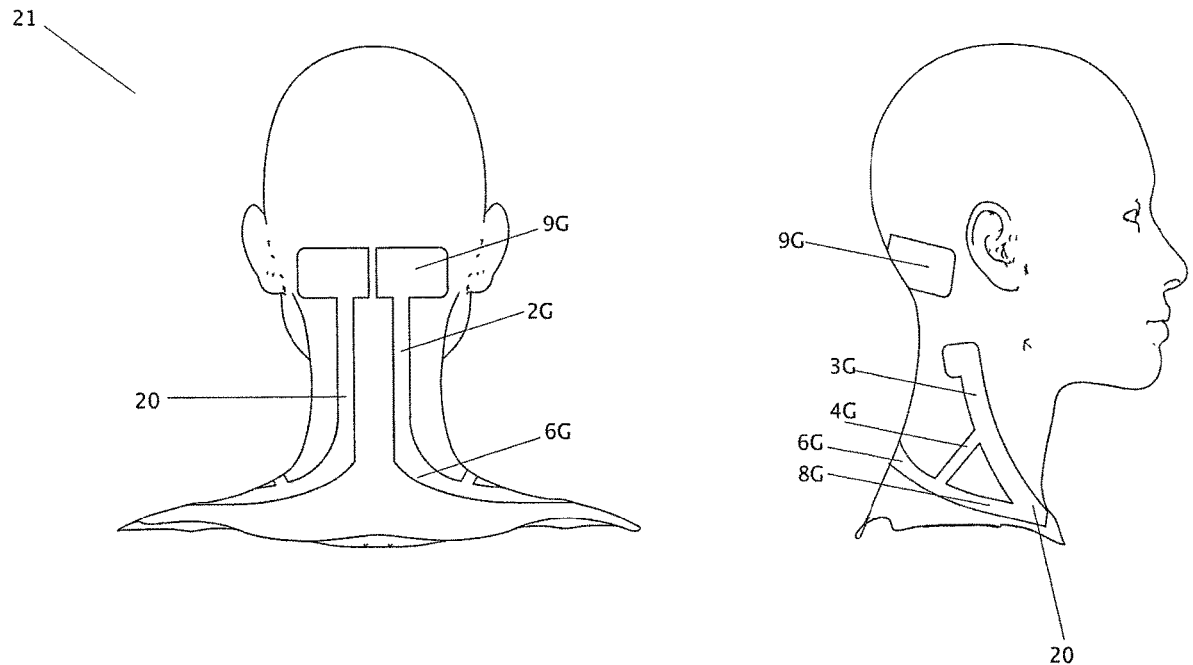
FIG. 13a depicts the embodiment of FIG. 13 as it would appear on a human neck both from a rear and profile perspective.

The embodiment 20 depicted in FIG. 13 displays a neck supporting apparatus with two separated pieces that are comprised of a material with structural properties on the spectrum from extensible to inextensible. There is support on the shoulders 6G with reinforcements that move upwards to the head, which support the trapezius muscles. The SCM support 3G will stabilize the head and neck so that excessive rotational and lateral movement is avoided. The scalene muscles are supported by the straps in 4G to reinforce head and neck lateral motions with the separated bases 8G and 6G acting as supports for 3G and 4G. The embodiment 20 is shown on a human neck in FIG. 13a from both rear and profile view.

Figure 14:
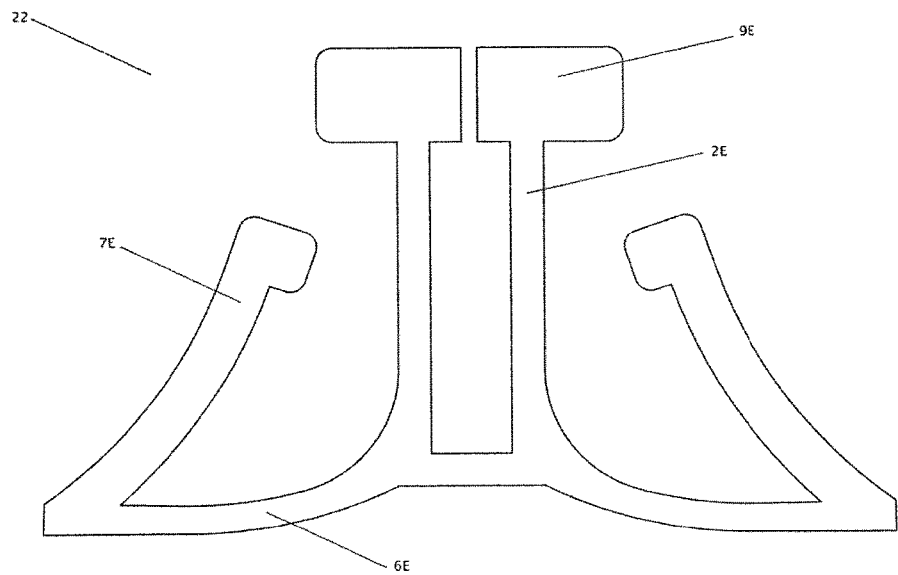
FIG. 14 depicts an embodiment of the neck supporting apparatus with reinforcement projections that radiate from the shoulders and base of the neck toward the head.
Figure 14A:
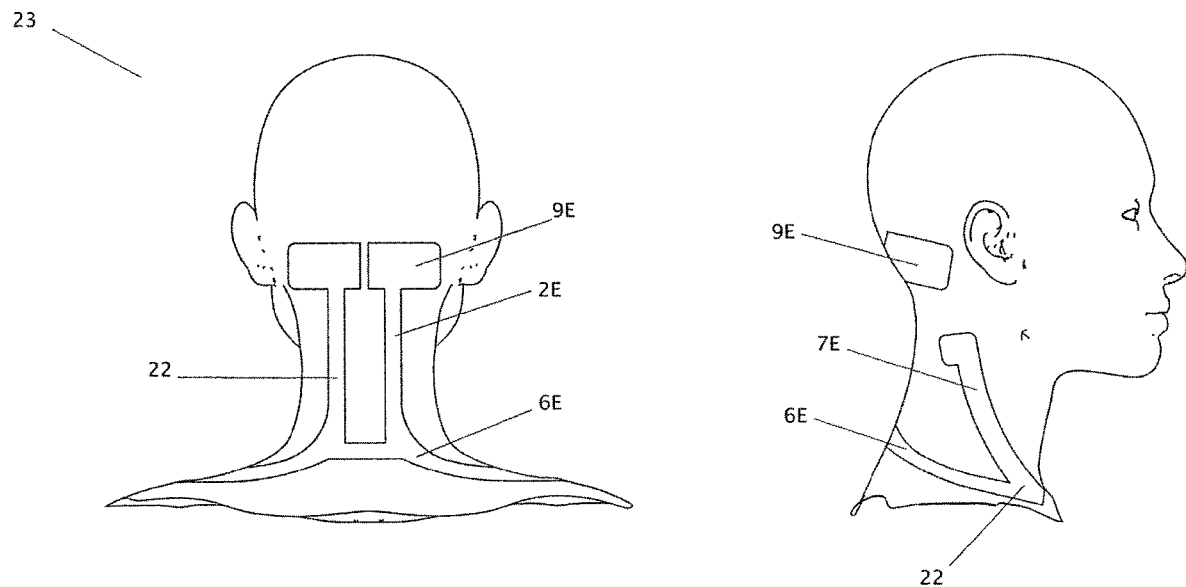
FIG. 14a depicts the embodiment of FIG. 14 as it would appear on a human neck both from a rear and profile perspective.

FIG. 14 depicts an embodiment 22 of the neck support apparatus comprised of materials with structural properties the shoulder support 6E serves as the base of the device with reinforcements moving upwards to the head. The trapezius supports 2E stabilize the upper portion of the neck. The SCM supports 7E reinforce rotational and lateral movement and the cranial supports provide stabilization for the occipital bone in the skull. FIG. 14a depicts the embodiment 23 on a human neck from both rear and profile views.

Figure 15:
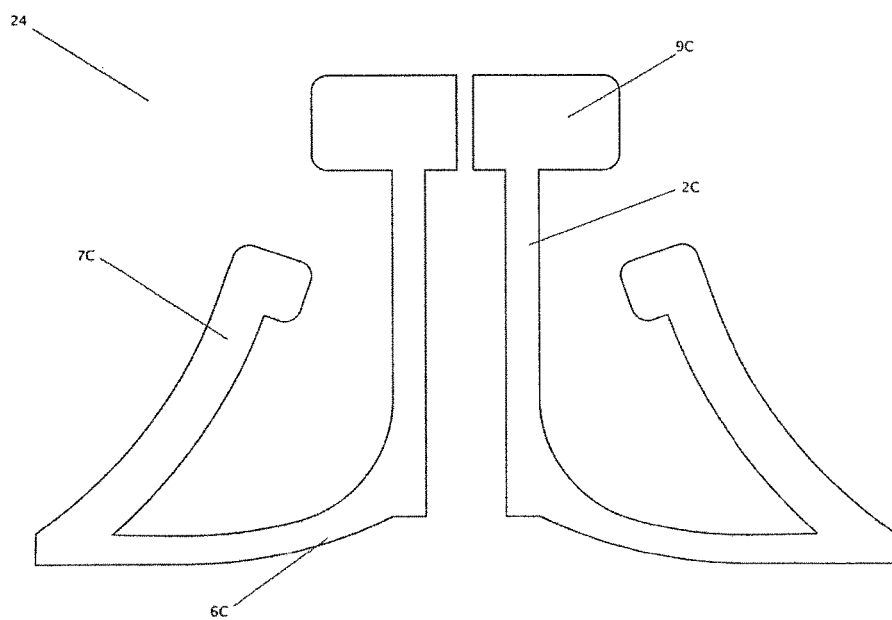
FIG. 15 depicts an embodiment of the neck supporting apparatus with reinforcement projections that radiate from the shoulders and base of the neck toward the head.
Figure 15A:
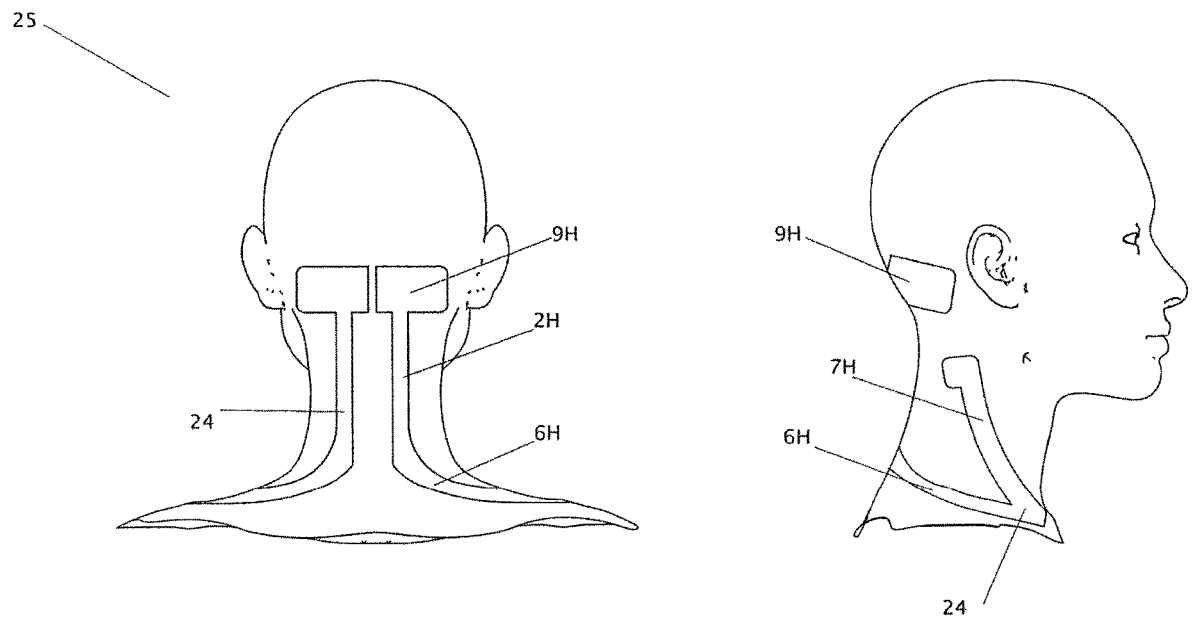
FIG. 15a depicts the embodiment of FIG. 15 as it would appear on a human neck both from a rear and profile perspective.

FIG. 15 shows the embodiment 24 of the neck support apparatus similar to the support system in FIG. 14. The base 6C provides support for the left and right shoulder. The reinforcements extend upward and serve as the trapezius supports. The pads behind the head 9C serve as the occipital bone support in the head, and the SCM supports 7C sustain the movement in rotational and lateral movement. FIG. 15a displays the embodiment 25 on the human neck from both the rear and profile view.

Figure 16:
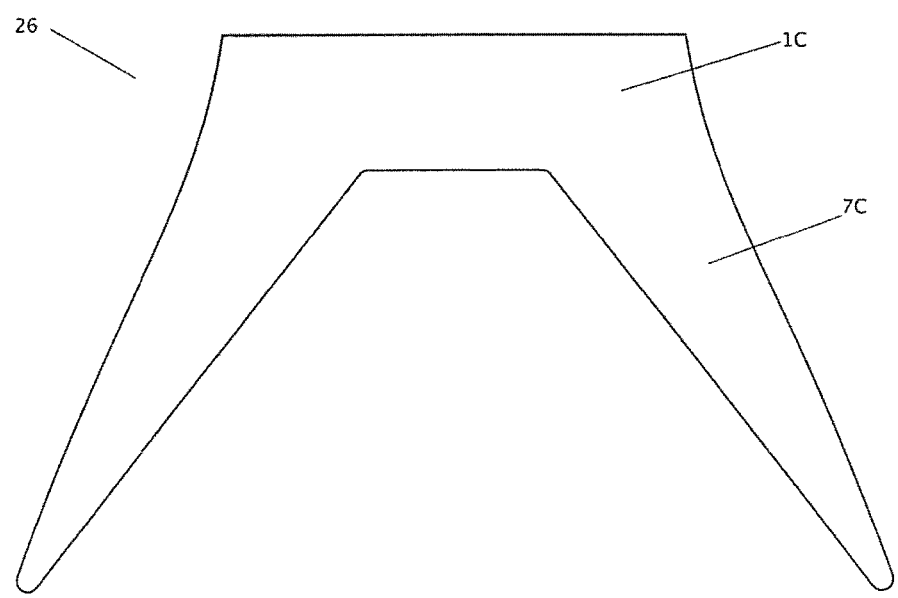
FIG. 16 depicts an embodiment of the neck supporting apparatus with reinforcement projections radiating from the base of the head toward the shoulders and base of the neck.
Figure 16A:
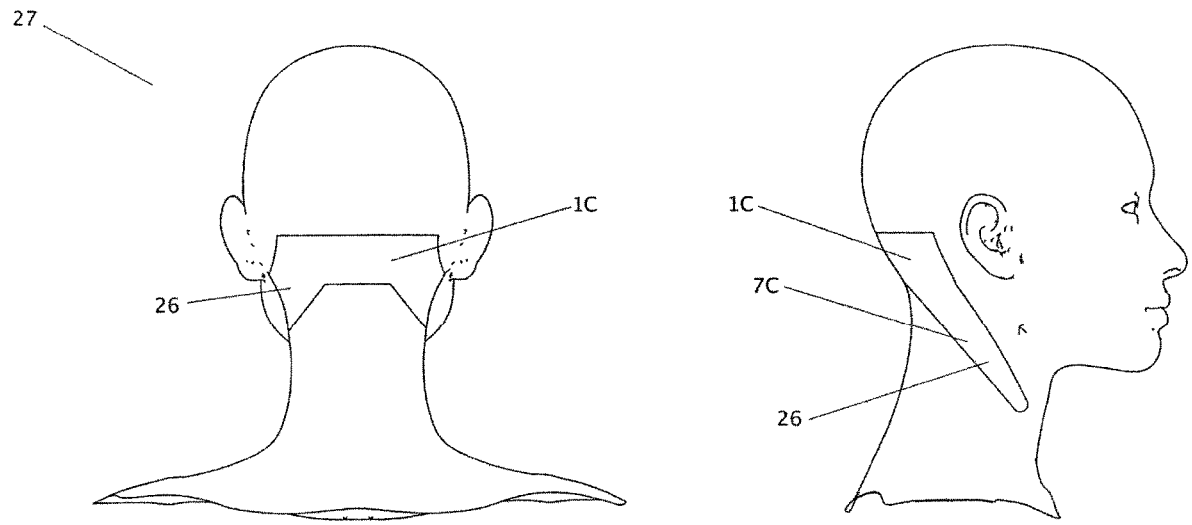
FIG. 16a depicts the embodiment of FIG. 16 as it would appear on a human neck both from a rear and profile perspective.

FIG. 16 depicts an embodiment 26 of the neck support apparatus made of similar material that is both flexible and rigid at the appropriate moments. There are no trapezius or scalene muscle supports. The SCM supports run through to the occipital bone supports 1C. This eliminates rotational and lateral movement as well as flexion and extension from the head. FIG. 16a depicts the embodiment 27 on the human neck from both the rear and profile view.

Figure 17:
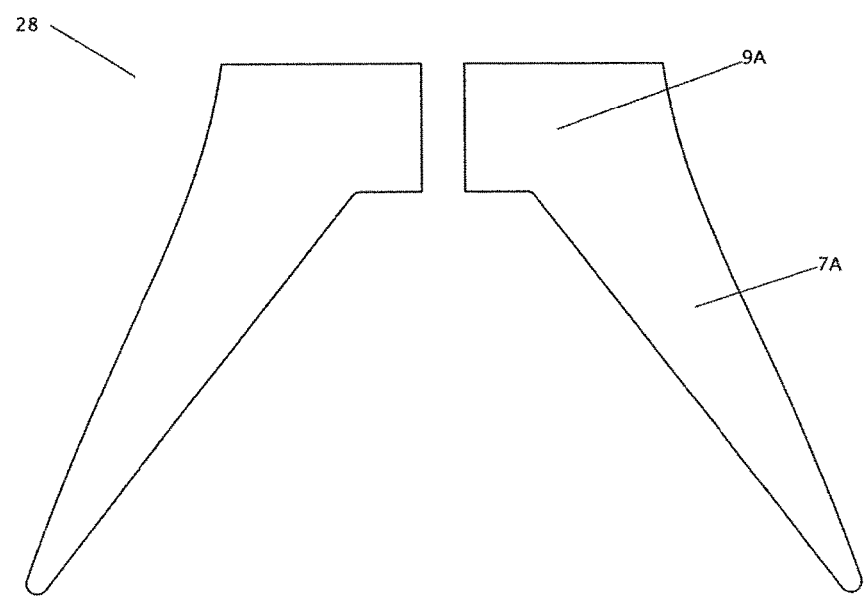
FIG. 17 depicts an embodiment of the neck supporting apparatus with reinforcement projections radiating from the base of the head toward the shoulders and base of the neck.
Figure 17A:
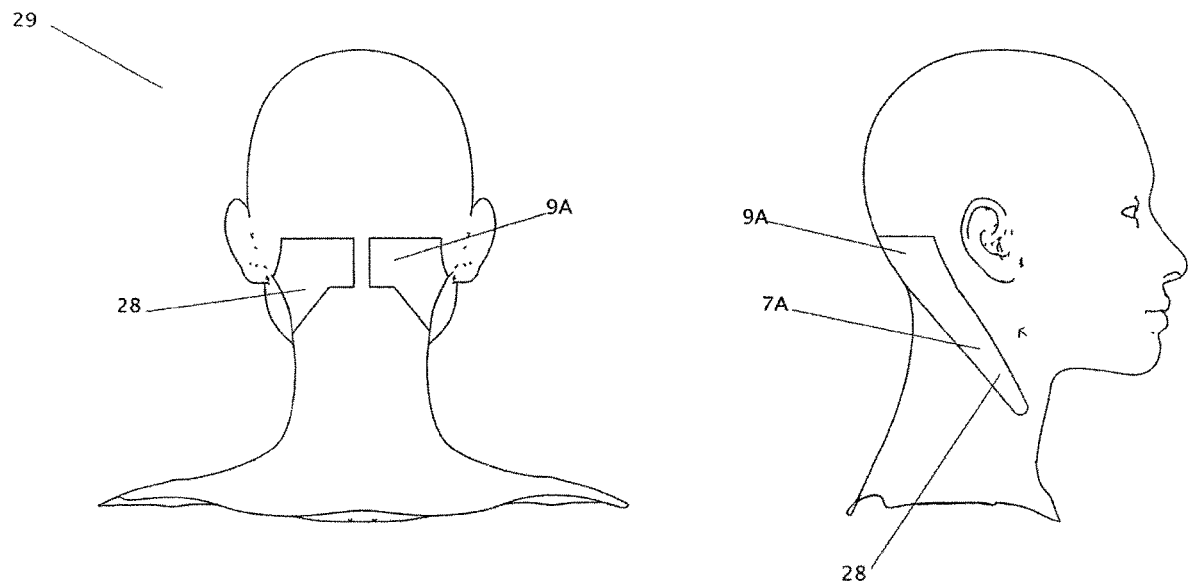
FIG. 17a depicts the embodiment of FIG. 17 as it would appear on a human neck both from a rear and profile perspective.

The embodiment 28 in FIG. 17 is similar to that in FIG. 16 where the SCM pads 7A support rotational and lateral movement and run upwards to connect to the head supports 9A. The neck support apparatus provides both flexibility and rigidity for support. FIG. 17a displays both the rear and profile view.

Figure 18:
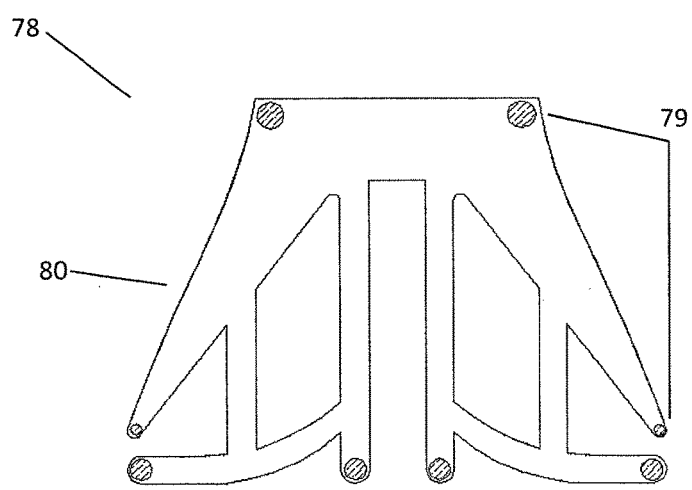
FIG. 18 depicts an embodiment of the neck supporting apparatus with placement markers.

FIG. 18 depicts an embodiment of the neck support apparatus 80 with a set of markers 79 to assist the user with proper placement of the neck apparatus. This apparatus provides support to the SCM through the outer flaps to eliminate rotation.

Figure 19:
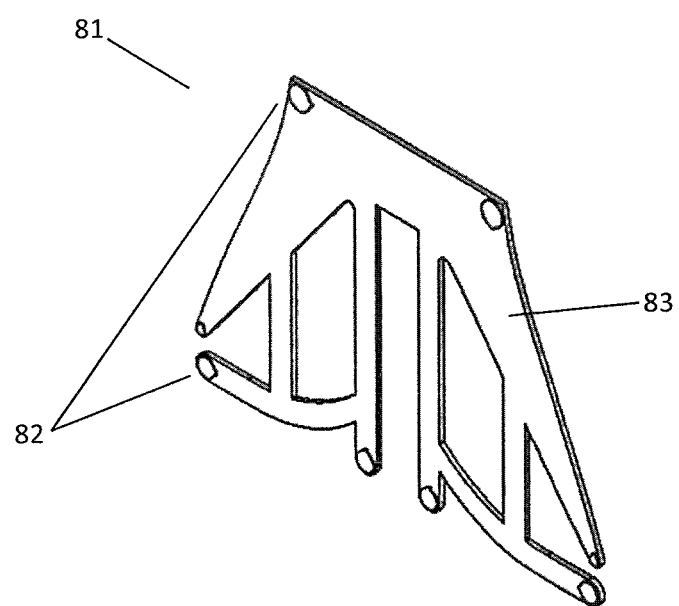
FIG. 19 depicts an embodiment of the neck supporting apparatus with adhesive release liners.

FIG. 19 depicts an embodiment of the neck support apparatus 83 having adhesive release liners 82 that allow repositionable placement of the apparatus on the user and proper alignment before the remaining liner is removed and the apparatus is firmly attached.

Figure 20:
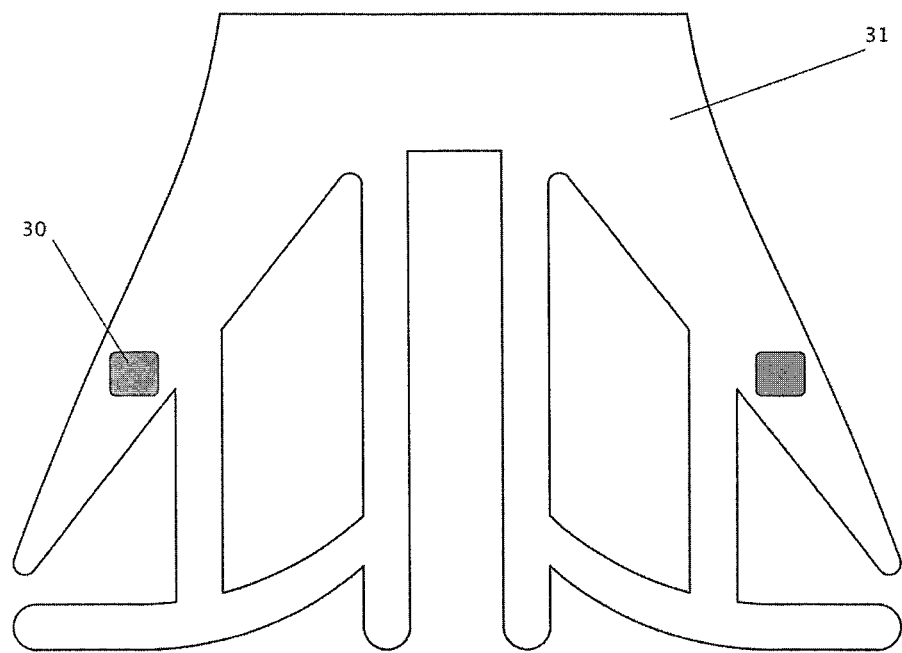
FIG. 20 depicts an embodiment of the neck supporting apparatus with reinforcement projections radiating from the base of the head toward the shoulders and base of the neck with jugular vein compression pads.

FIG. 20 shows an embodiment of the neck supporting apparatus similar to the embodiment 10 shown in FIG. 8. However, this embodiment 31 further includes jugular vein compression pads 30. These pads 30 apply slight pressure to the jugular vein on either side of the human neck; this action causes an increase in cranial pressure, which, in turn, leads to a higher volume and thus higher density of the intracranial fluid. The higher density fluid provides further shock absorption for the brain, and prevents excessive jostling upon impact.

Figure 21:
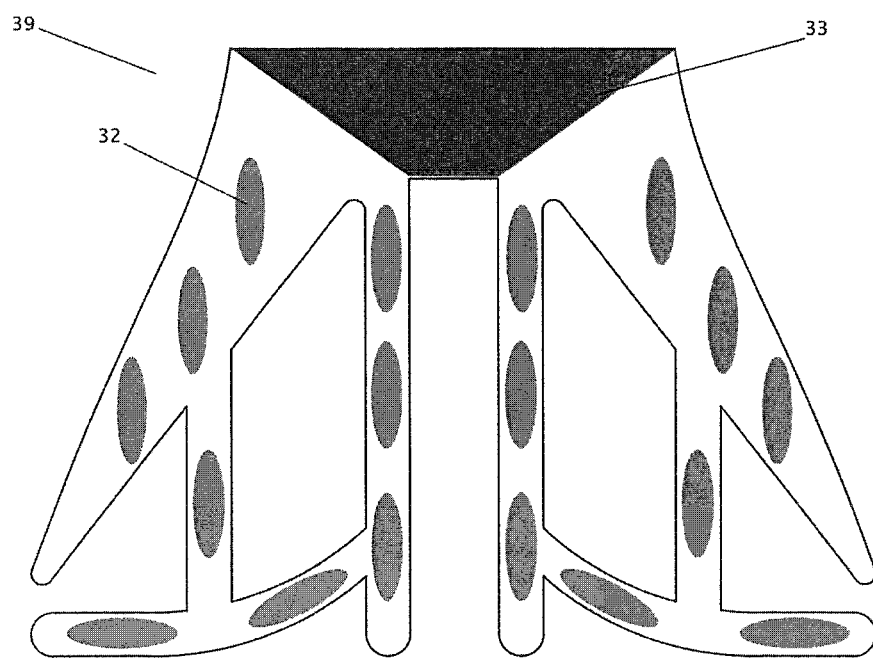
FIG. 21 depicts an embodiment of an adhesion method for the neck supporting apparatus.

FIG. 21 depicts an embodiment of the neck supporting apparatus 39 similar to the embodiment 10 shown in FIG. 8. This FIG. 21 serves to display an attachment mechanism for the neck supporting apparatus. Shown are adhesive patches 32, which may be reusable, disposable, peel-off, or require adhesive remover, as previously mentioned in this section. Further, there is high friction section 33 at the base of the head, which provides some displacement resistance while avoiding painful hair pulling. Alternatively, the high friction section 33 can be located on the lower section of the supporting apparatus 39.

The attachment of said neck supporting apparatus 39 may take many forms. The device may have a rigid clamshell structure and mechanism including a hinge point 36 (FIG. 23) and a maximum closing range that is suitable for a specific person's neck so as to fit comfortably without blood flow or airway restriction. In this embodiment of the concussion prevention neck support the interior lining of the device likely consists of a high friction material in section 33 to prevent device displacement. Alternatively, the neck supporting apparatus 39 may have spring like properties about a hinge point 36 (FIG. 23) made from an elastomer, rubber, graphene, or metal such as nitinol that lightly clamps the device around the back of the neck and uses a high friction material in section 33 or adhesive surface 32 to prevent device displacement. The device may also be a soft closed structure that fully encircles the wearer's neck like a balaclava as a means of attachment. Again, this embodiment would likely include a high friction interior lining in section 33 to prevent device displacement and to ensure that the neck supporting apparatus 39 displacement matches the skin displacement. The device may alternatively have an adhesive attachment mechanism. The adhesive interface may cover the entire interior surface as a single piece 34 (FIG. 22) or may consist of one or more smaller adhesive surfaces 32 (as in FIG. 21). This adhesive may be reusable either indefinitely or for a predetermined period of time. Additionally, the adhesive may be a single use, peel-off variety. For the single use adhesive embodiment, either the device includes multiple adhesive coverings so a new cover or covers are used for each wear or the entire device is single use and thus disposable. For both the reusable and single use adhesive varieties, their removal may be either a peel-off mechanism or prompted by a remover/solvent.

Figure 22:
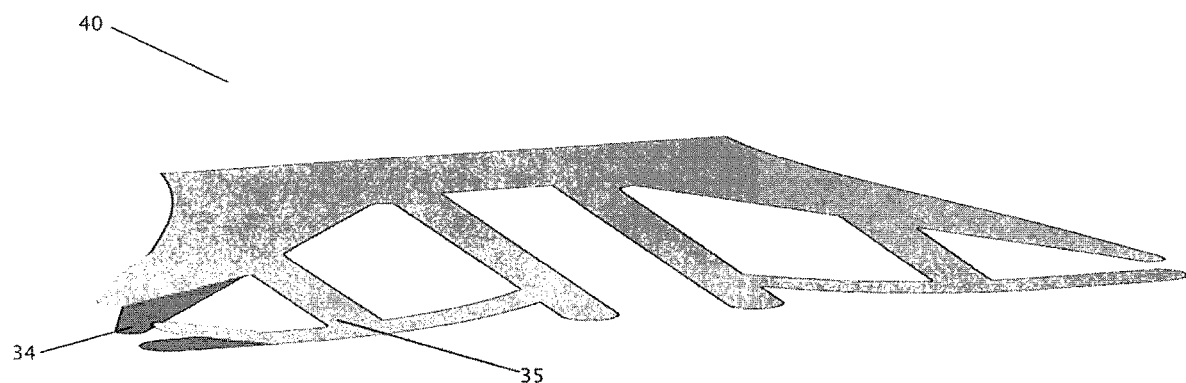
FIG. 22 depicts an embodiment of an adhesion method for the neck supporting apparatus.
Figure 23:
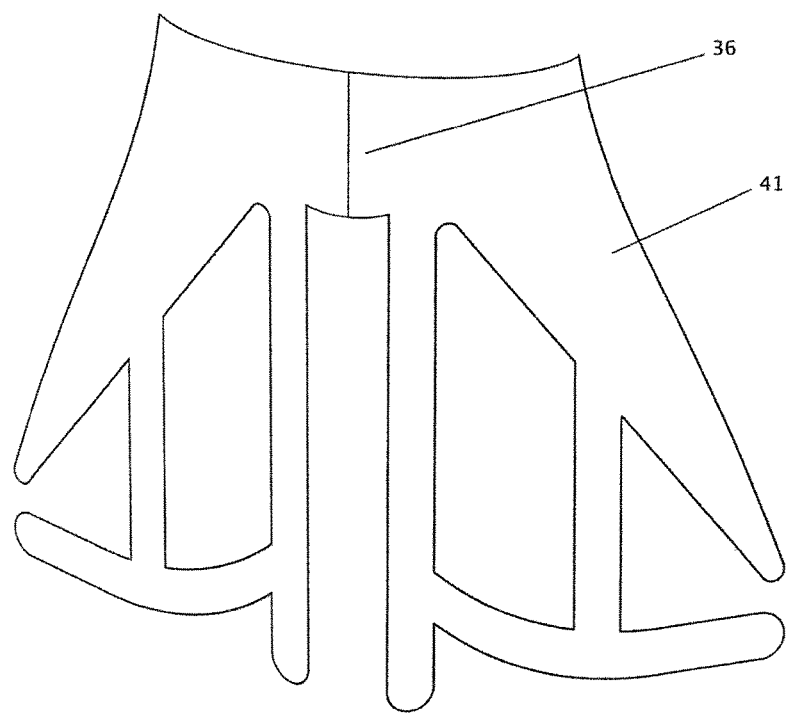
FIG. 23 depicts an embodiment of a clamshell attachment method for the neck supporting apparatus.

FIG. 22 depicts an embodiment of the neck support apparatus 40 similar to the embodiment 10 shown in FIG. 8. This FIG. 22 serves to display an attachment mechanism for the neck supporting apparatus 40. In this embodiment 40, the neck supporting apparatus adheres to the neck using a single-piece adhesive layer 34, which may be reusable, disposable, peel-off, or require adhesive remover, as previously mentioned in this section. This adhesive protective layer 35 lays over the adhesive surface 34 of the neck supporting apparatus. FIG. 23 depicts an embodiment of the neck support apparatus 41 similar to the embodiment 10 shown in FIG. 8. The attachment method of this apparatus is a clamshell like mechanism. The neck supporting apparatus collapses around a hinge 36 at the base of the head. The range of the mechanism is adjusted according to the individual diameter of the neck, so as to avoid restricted blood flow or air passages.

Figure 24:
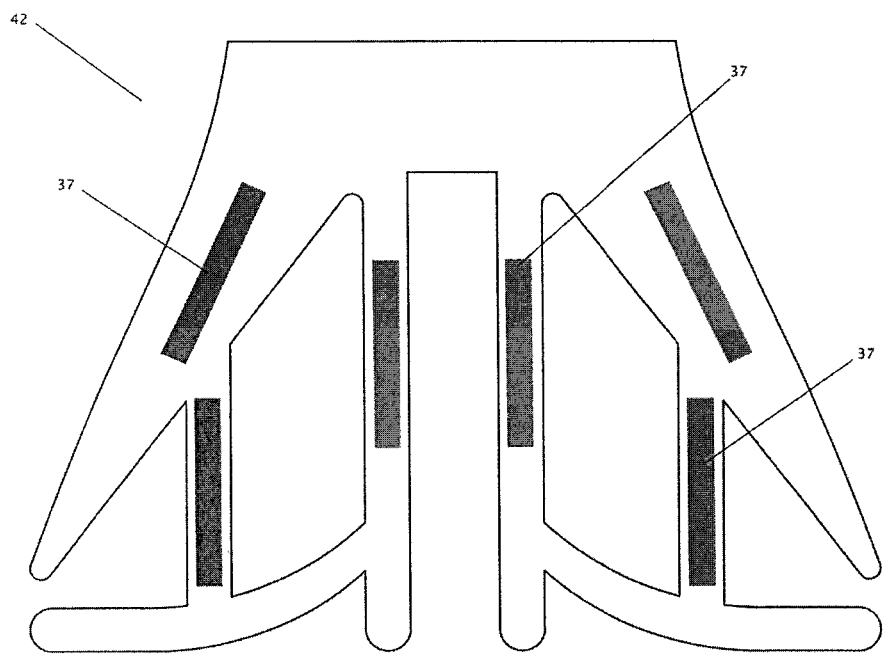
FIG. 24 depicts an embodiment of a magnetic attachment method for the neck supporting apparatus.
Figure 24A:
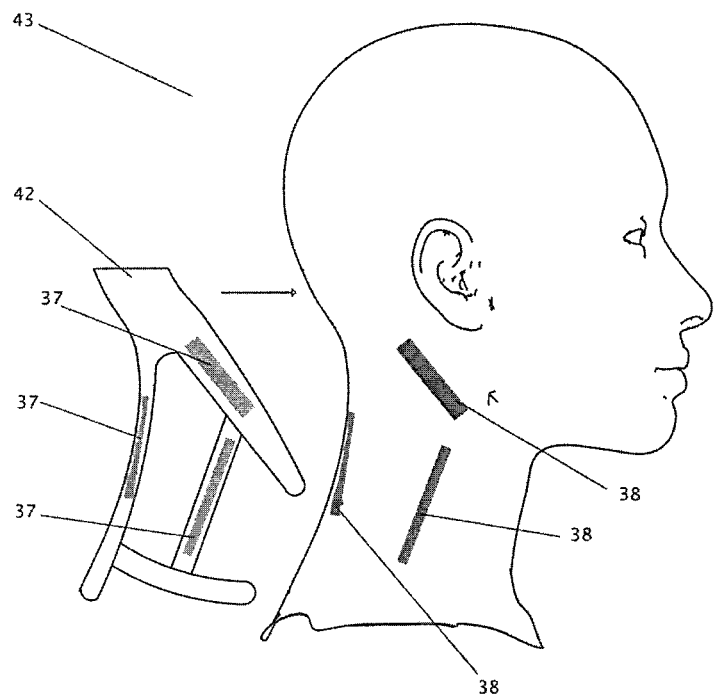
FIG. 24a depicts the embodiment of FIG. 24 showing the placement of magnetic strips on the neck supporting apparatus and the human neck.

FIG. 24 depicts an embodiment of the neck support apparatus 42 similar to the embodiment 10 shown in FIG. 8. The attachment method of this apparatus employs various magnetic pieces with one portion 38 (FIG. 24A) adhering to the neck and the other 37 to the neck supporting apparatus. FIG. 24a demonstrates the magnetic pieces 37, mating with their portions 38 on the neck. Further, there may be other intermediate interfaces between skin and device, such as Velcro, clips, or other self-adhering materials. In this embodiment of the neck supporting apparatus 42, one portion of the self-adhering 38 material is attached to the skin, likely by one of the previously mentioned adhesives, and the other portion of the self-adhering material 37 is attached, likely permanently, to interior lining of the device. Finally, the attachment mechanism may be any combination of the above-mentioned methods so as to best suite its functionality.

Figure 25:
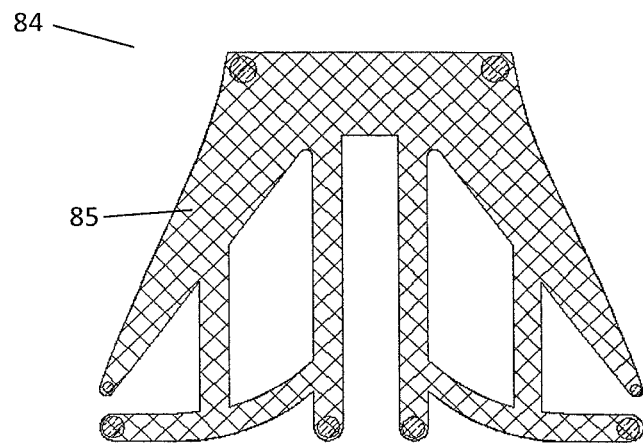
FIG. 25 depicts an embodiment of placement markers and breathability for the neck supporting apparatus.

FIG. 25 depicts an embodiment of the neck support apparatus 84 that is comprised of breathable material 85 so that perspiration can evaporate from the user.

Figure 26:
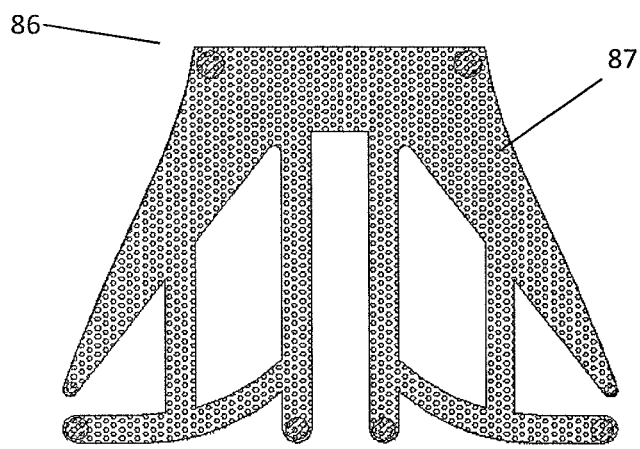
FIG. 26 depicts an embodiment of placement markers and breathability for the neck supporting apparatus.

Alternatively, the neck apparatus may have perforations 87 as shown in FIG. 26. Each of these embodiments of the neck supporting apparatus 84 and 85 serves to keep the users neck cooler as well as to assist adhesion by reducing moisture retention.

Figure 27:
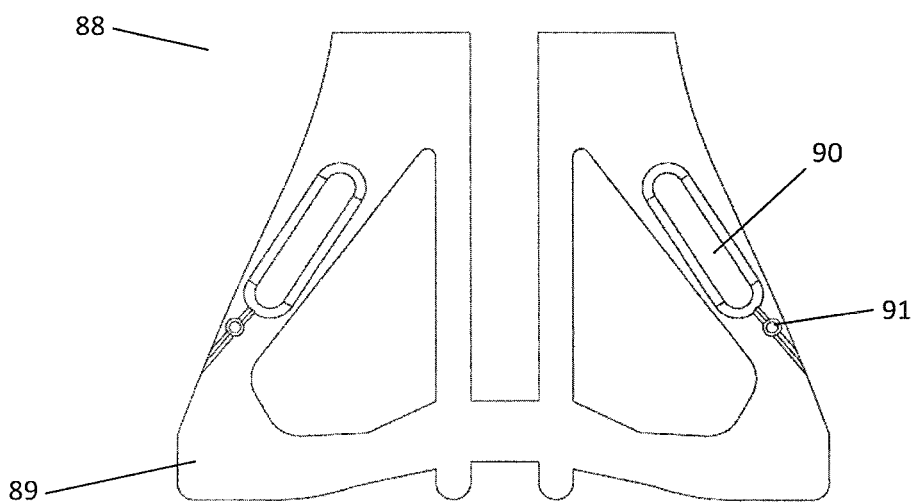
FIG. 27 depicts an embodiment of the neck supporting apparatus with reinforcement projections radiating from the base of the head toward the shoulders and base of the neck with jugular vein compression bladders.

FIG. 27 depicts another embodiment of the neck support apparatus 88 configured to allow compression of the jugular veins via patches 90 in the neck so as to increase cranial blood pressure, further reducing any trauma to the brain. This compression may be adjustable, may increase with movement to the neck apparatus or otherwise be triggered upon acceleration sensed at 91. Also note that the neck support apparatus may be configured with other geometries as shown.

Figure 28:
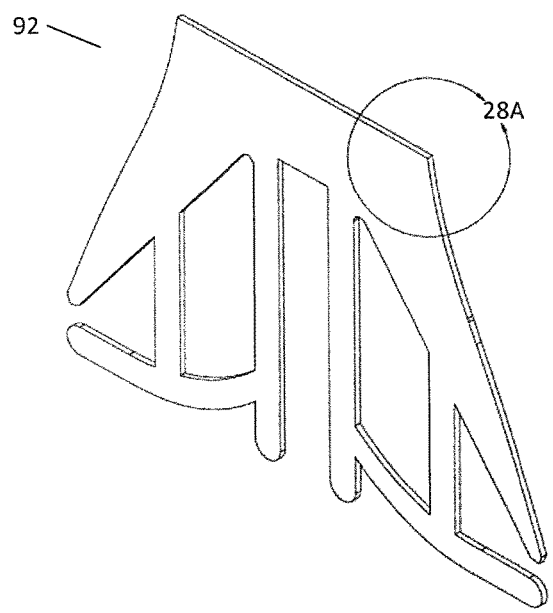
FIG. 28 depicts an embodiment of the neck supporting apparatus showing the edge detail.
Figure 28A:
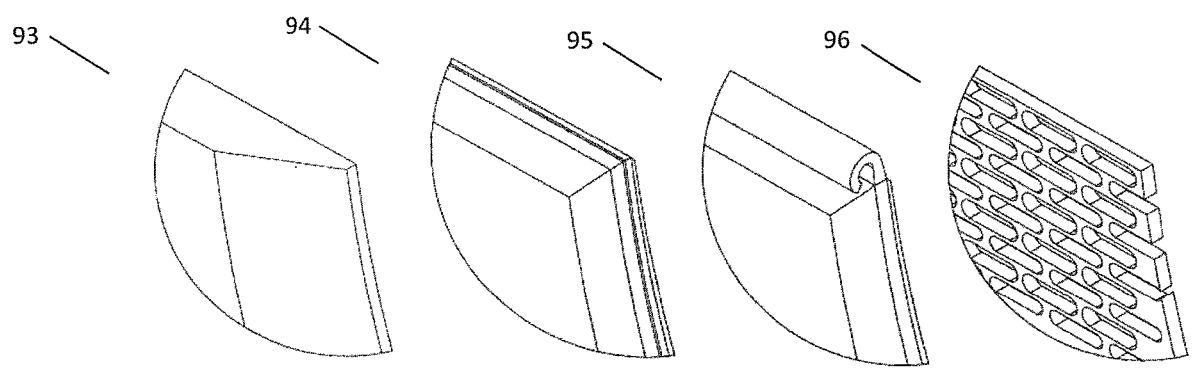
FIG. 28a depicts various edge detail embodiments for the neck supporting apparatus of FIG. 28.

FIGS. 28 and 28a depict an embodiment of the neck support apparatus 92 with exposed edges that reduce trauma to the neck when bending, these edges may be turned up, radiused 95, tapered 93, thinned 94, or cut in a fashion to act as a strain relief. One embodiment has staggered slots 96 through the thickness to reduce the flexural forces exhibited at the exposed edges.

It is beneficial that the neck supporting apparatus 45 as depicted in FIG. 1 for example both be supportive and allow the user 51 a full range of motion. Ideally, the apparatus 45 will be able to transition from free motion to stiff simply, efficiently, and with acceleration damping qualities. An optimal material for a structure such as this is Shear Thickening Fluid (STF) 140 depicted in FIG. 29. Also called a dilatant or strain-rate sensitive material, or more informally termed oobleck, STF 140 is a non-Newtonian fluid, gel, or suspension that displays an increase in viscosity with an increase in shear stress. This means that the STF 140 may act as a fluid or flexible structure normally, but then will stiffen when exposed to a rapid change in force. The STF 140 will add support in accordance with the magnitude of any compression, extension, or bending force.

Figure 29:
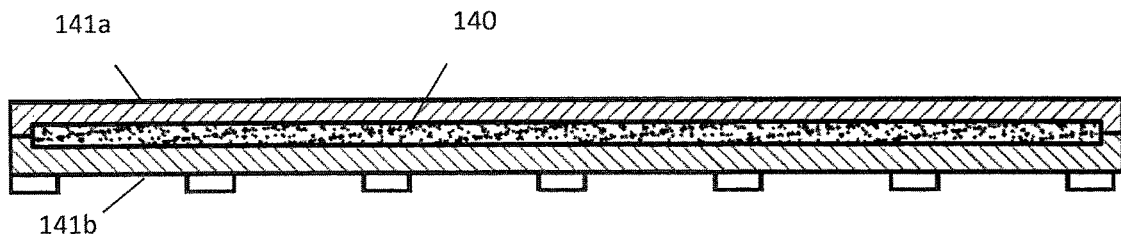
FIG. 29 is a cross-sectional view drawing of a composite material containing Shear Thickening Fluid.
Figure 30:
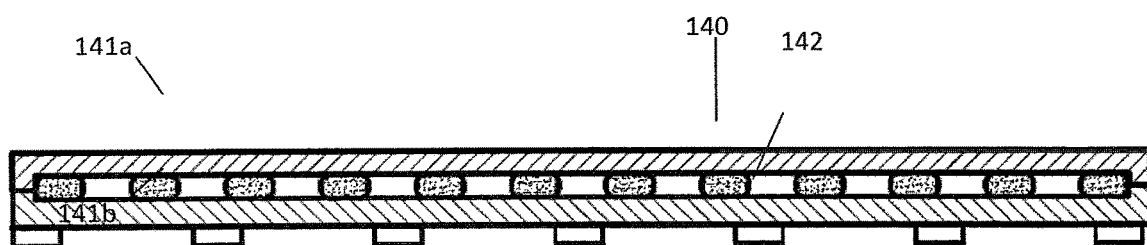
FIG. 30 is a cross-sectional view drawing of a composite material with Shear Thickening Fluid-containing compartments.

It is possible to integrate the STF 140 into a composite material 141, as seen in FIG. 29. The top 141a and bottom 141b portions of the composite material shown in the cross-sectional view may comprise any of the features noted in FIGS. 6 and 6a while enclosing the STF 140. This will give the STF 140 a structure with which to engage with the user 51 (not shown). FIG. 30 depicts the same concept, except the STF 140 is held in small compartments 142. These compartments 142 ensure an even distribution of the STF 140 throughout the area of the composite material 141.

Figure 31:
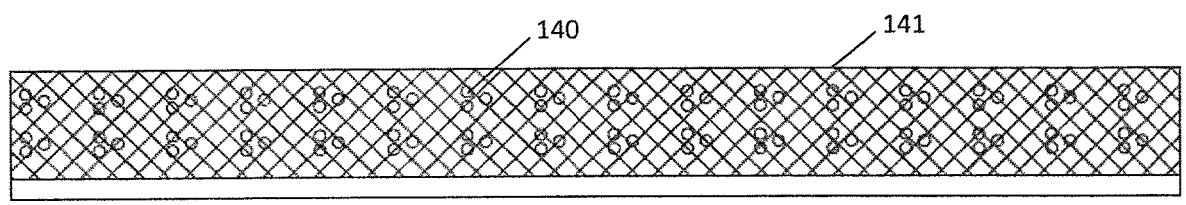
FIG. 31 is a cross-sectional view drawing of a composite material with embedded Shear Thickening Fluid.

Alternatively, the STF 140 may be embedded directly into the composite material 141, as shown in FIG. 31. Embedding the STF 140 will allow the composite material to be thinner because there will no longer be a need for pockets or compartments 142 in which to hold the STF 140.

Figure 32:
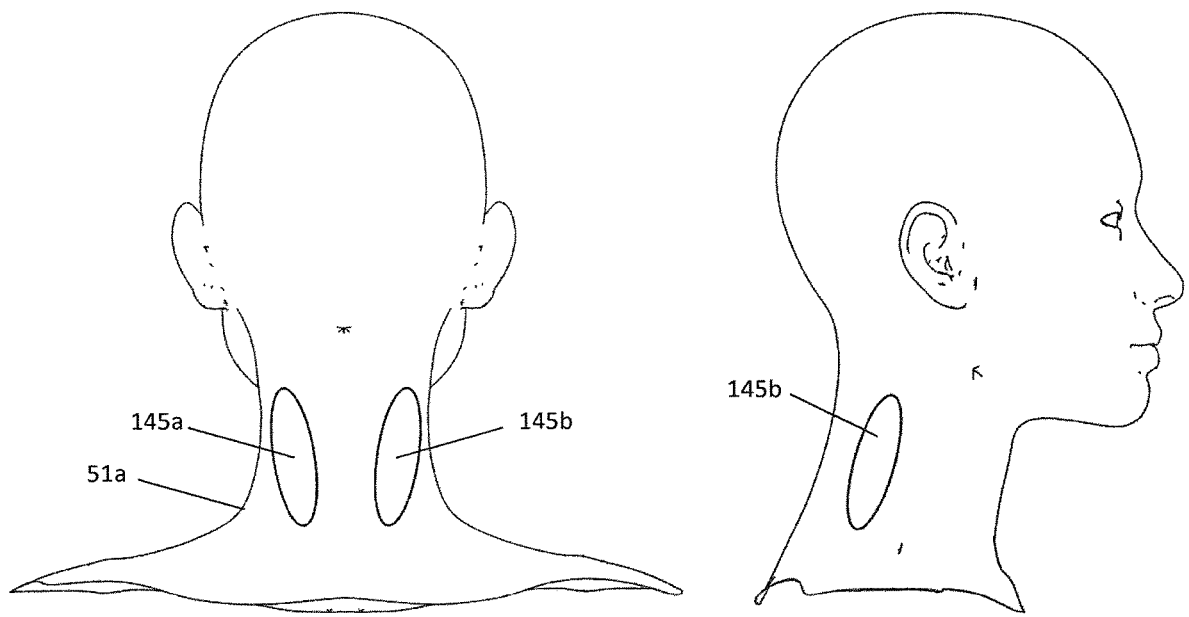
FIG. 32 is an embodiment of the neck supporting apparatus composed of STF-embedded elliptical bands from both from a rear and profile perspective.
Figure 33:
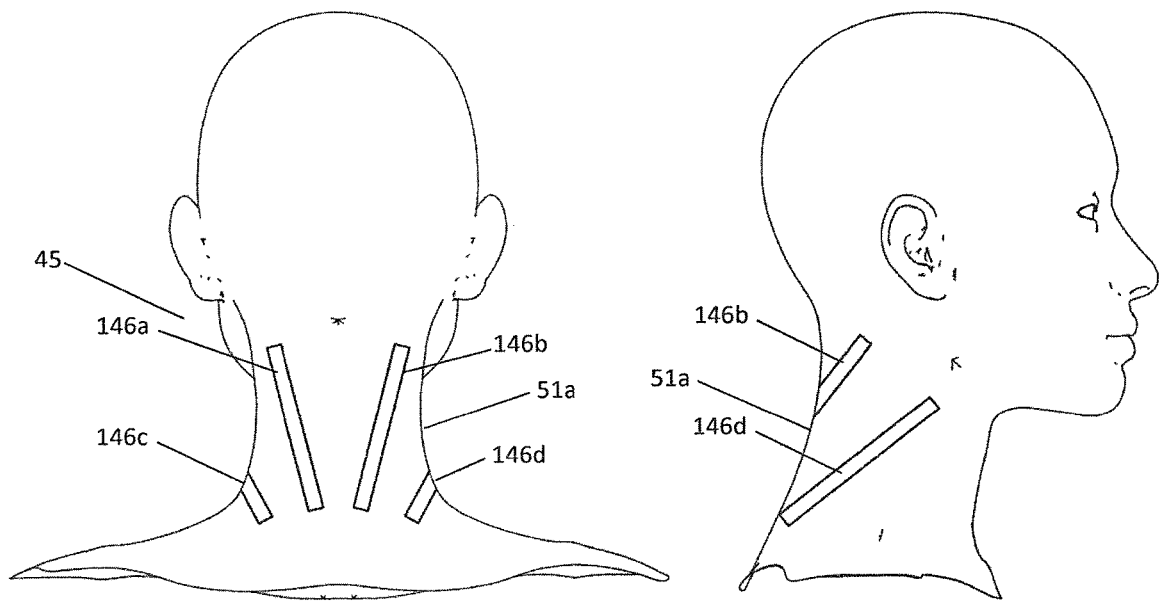
FIG. 33 is an embodiment of the neck supporting apparatus composed of STF-embedded straight bands from both from a rear and profile perspective.

FIG. 32 depicts the STF 140 (not shown) in a composite material 141 as described in FIGS. 29 through 31 engaged with the user's neck 51a by elliptical bands 145. The elliptical bands 145a and 145b are adhered to the user's neck 51a in any way as previously described and may bend, extend, or compress with the motion of the user 51. The stretching and bending of the elliptical bands 145a, b compresses the enclosed STF 140. At high rates of flexion or extension, the large force of compression will stiffen the STF 140, thereby causing the entire band 145 to become rigid. This rigidity will support the neck 51a and reduce the acceleration of the head, relative to the torso, before injury can occur. FIG. 33 depicts another embodiment of the neck supporting apparatus 45 using STF 140. This embodiment is similar to that of FIG. 32 above but with the composite material 141 formed into straight bands 146a-d. These bands may run the length of a muscle, such as the trapezius bands 146a and 146b or the SCM bands 146c and 146d, or they may be placed straight up or at any other angle on the neck 51a.

Figure 34:
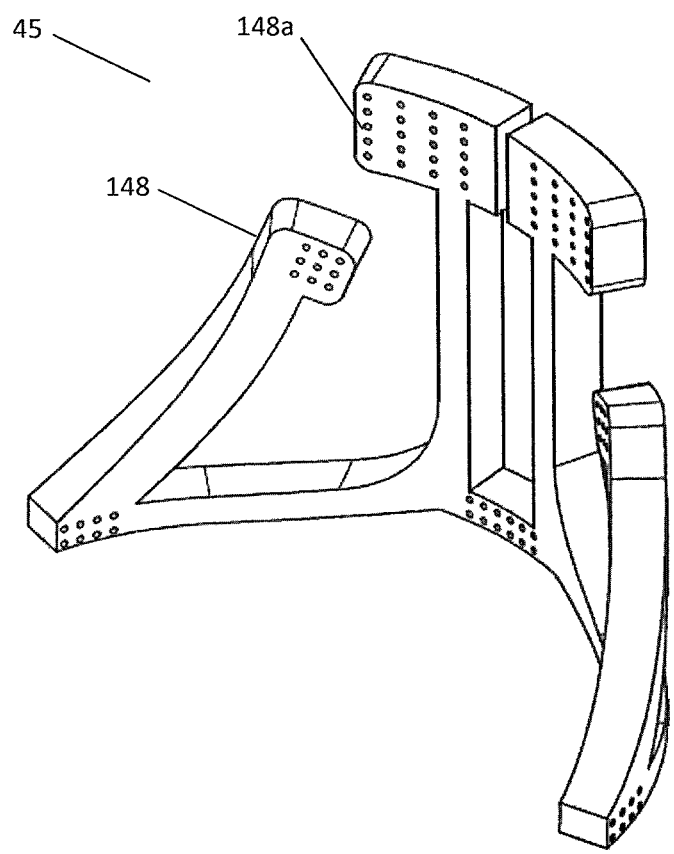
FIG. 34 depicts an embodiment of the neck supporting apparatus with STF embedded in a thick supporting structure.
Figure 35:
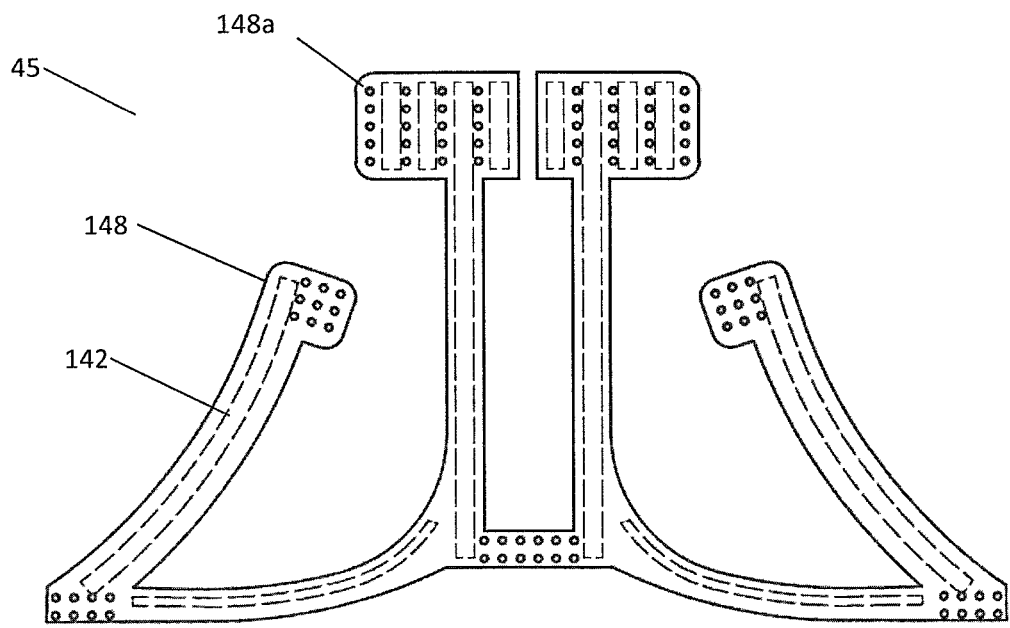
FIG. 35 is a cross-section drawing of an embodiment of the neck supporting apparatus with STF embedded in a thick supporting structure.

FIGS. 34 and 35 depict another embodiment of the neck supporting apparatus 45 wherein STF 140 is enclosed in a thick supporting structure 148. The embodiment is similar to that seen in FIG. 9, except this embodiment utilizes a thick supporting structure 148 rather than the minimal thin material. The thick supporting structure 148, which may be any foam, layered fabric, plastic, or other structural material, may be curved to securely fit the neck 51a (not shown), have linkages to hold it around the neck, or have adhesive to hold it against the neck. This structure will provide constant support. The thick supporting structure 148 will be somewhat flexible to allow for full range of motion, and it will be breathable, with a series of small airholes 148a to maintain user comfort while in use. Embedded compartments of STF 142 will be located throughout the structure 148, which will allow the structure 148 to stiffen and withstand larger impacts. This embodiment would be ideal for users such as football or lacrosse players who already utilize a large amount of padding. For these applications, the structure 148 may be able to attach to the user's helmet or shoulder pads.

Figure 36:
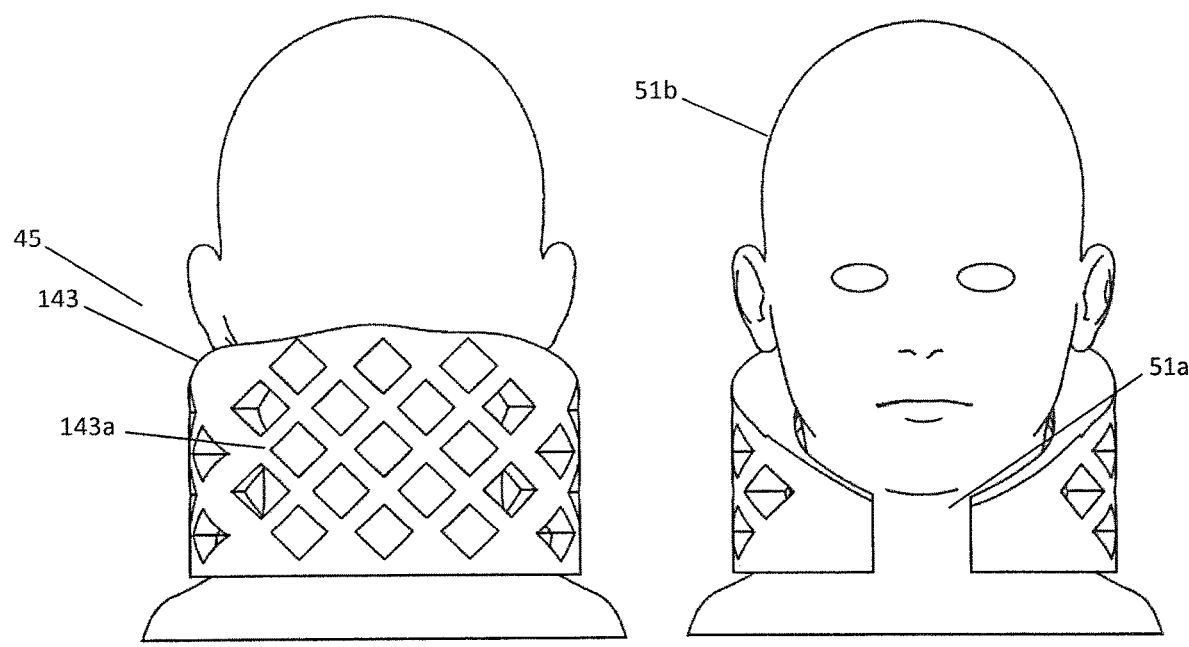
FIG. 36 depicts an embodiment of the neck supporting apparatus with a supporting collar embedded with STF both from a rear and profile perspective.

FIG. 36 depicts another embodiment of the neck supporting apparatus 45 wherein a supporting collar 143 is fitted around the user's neck 51a. This embodiment is similar to that of FIG. 35, as STF 140 (not shown) is embedded in the structure to give it further support during large impacts. The structure is thick and soft, allowing for a cushioning effect if the user's head 51b is forced too far in one direction. The lattice structure 143a, shown here as cross hatching but may also be any triangular pattern, chevron pattern, woven pattern, or other series of shapes, allows the structure to compress slightly with the head's 51b movement while still allowing the overall collar 143 to be breathable. STF 140 embedded within the lattice structure 143a increases the stiffness only when great amounts of force are applied.

Figure 37:
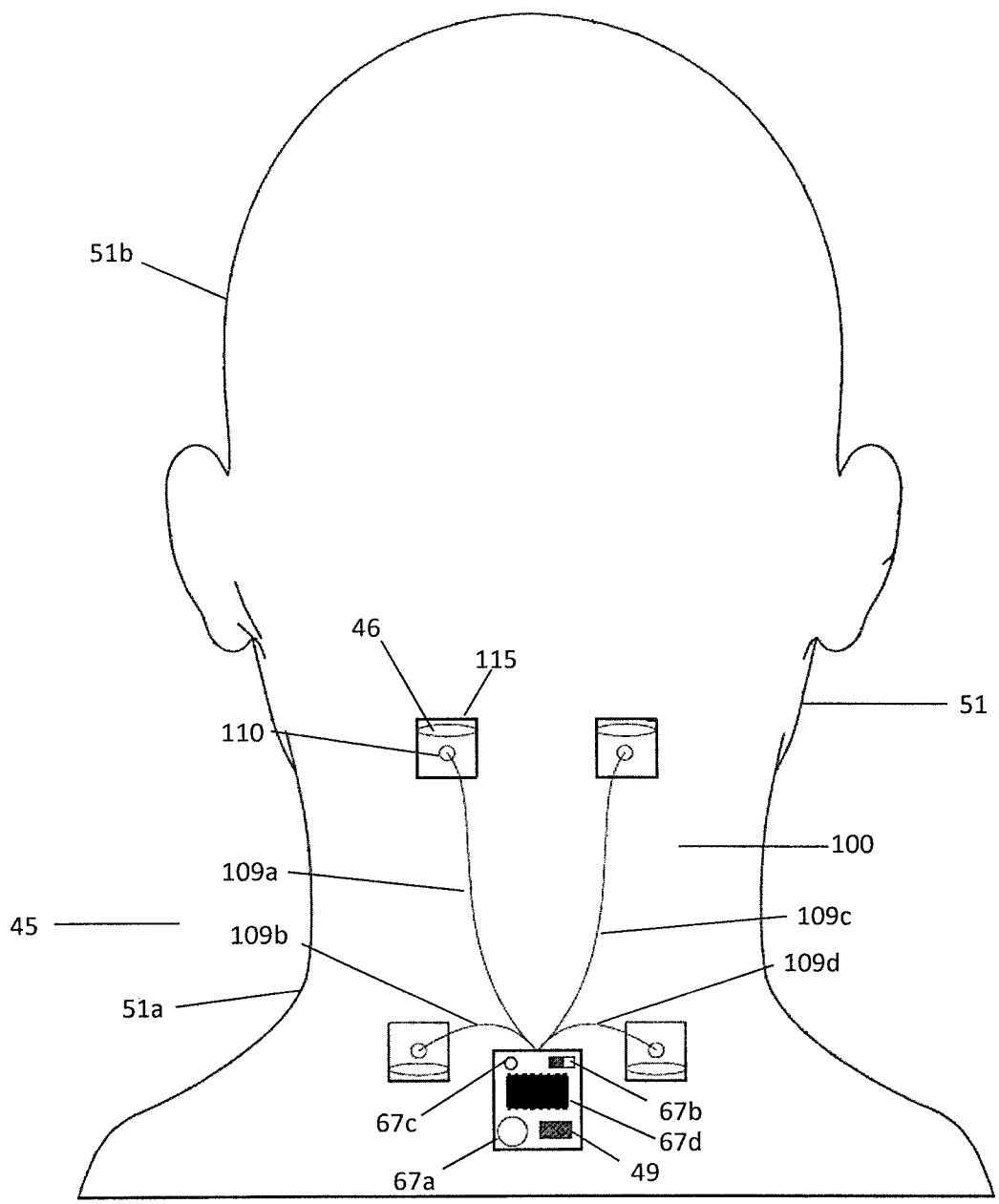
FIG. 37 depicts an embodiment of the neck supporting apparatus using electrical stimulation.

Further embodiments of the neck supporting system 44 and apparatus 45 may utilize muscle stimulation or otherwise employ features of the user's anatomy to reduce trauma. FIG. 37 depicts an embodiment of the neck supporting system 44 wherein the user's musculature, at least including, but not limited to, the trapezius, scalenes, levator scapulae, and sternocleidomastoid, are made to tighten, contract, or otherwise stiffen by means of external electrical stimulation. The neck supporting system 44 includes a series of sensors 46, which may be any type of strain gauge, accelerometer, force sensor, motion sensor, or other movement monitoring device. The sensors 46 will measure the movement of and forces acting against the user's head 51b and/or neck 51a. This data will be sent to the control system 67, which is comprised of any necessary electronics including a power supply 67a, an on/off switch 67b or other power control, an LED 67c or other means of displaying power output such as a buzzer, and a microcontroller 67d or any other means of programming the control system 67. The power supply 67a may be comprised of one or multiple rechargeable batteries, piezoelectric devices, kinetic charging devices, or any other device that may power the system 44 using the thermal or kinetic energy created by the user 51.

The control system 67 may also include wireless communication 49, which will allow the sensor 46 data and any actions taken by the control system 67 to be relayed to an optionally included user interface 52 (not shown) or to an external database 47 (not shown), which may also give the user 51 the ability to program the support system 100. The external database 47 (not shown) will include options for programming the muscle stimulation for each user and may include variables such as age, gender, weight, neck girth, and muscle strength. The database may also include instructions for the user in the placement of the support apparatus 100 as well as how to manually alter the frequency, duration, and intensity of the stimulation.

When the sensors 46 relay force data to the microcontroller 67c, the program will decide if the force is large enough to require protection of the user's musculature. If the force is large, then the microcontroller 67c will activate one or more pairs of electrodes 110, which are connected to the control system 67 by a conductive material 109a-d such as a wire or film or wirelessly. These electrodes 110, which have been engaged with the user 51 via repositionable adhesives 115, will use steady or pulsed electrical voltage to elicit muscle contractions. The stiffening or tensing of the muscles in the neck 51a will provide the needed structure to dampen the effect of the forces that caused the head to accelerate, thereby reducing the possibility of trauma. Following the reduction of outside forces upon the user 51, the electrodes 110 will stop the voltage potential and return full motion control to the user 51. The number of electrodes 110 and their placement may vary depending upon the amount of support required or on the muscles to be engaged. FIG. 37 shows two electrode 110 pairs placed vertically along the left and right trapezius muscles. The electrodes 110, along with their adhesives 115, may be also be removably attachable from the rest of the neck supporting system 100. The electrodes 110 may have snap, hook-and-loop, button, magnetic, or any other form of removable connection so that the electrodes 110 and adhesives 115 may be replaced if necessary.

There are many different modes of Electronic Muscle Stimulation (EMS) that could be utilized by the apparatus 45. The three most common types used are Transcutaenus Electrical Stimulation (TENS), Russian Stimulation, High Voltage Pulse Currents, and Interferential Currents (IFC). The apparatus 45 could also utilize EMS techniques such as Aussie Stimulation or Burst Mode Alternating Current Elongated Period (BMACEP).

TENS is primarily used to decrease chronic pain. The concept behind TENS is to disrupt the electrical responses the muscle sends to the brain to signal pain. The apparatus 45 can be used therapeutically to help reduce acute neck pain caused by trauma to the neck or other forms of neck damage. The system would utilize TENS to test a range of electrical frequencies that may help reduce the severity of pain the user experiences in the affected muscle regions. The amplitude of the current the apparatus produces can be altered by the user 51 within a predetermined safe range in order to reach deeper muscle tissue the user would like to treat. The apparatus could also be used to help reduce migraines. The FDA has previously approved similar devices. The apparatus 45 would not utilize TENS across the front of the neck (risk of hypotension), over the eyes (risk of increasing intraocular pressure), directly over the spinal column or transcerebrally. TENS concentrates on the specific location the electrodes 110 are placed on the user's skin 51. The apparatus 45, could also integrate a non-invasive Electrical Twitch Obtaining Intramuscular Stimulation (ETOIS) system to therapeutically help reduce acute neck pain caused by trauma to the neck or other forms of neck damage.

Russian stimulation, a type of Burst Mode Alternating Current (BMAC), utilizes electrical currents to contract muscle tissue. Russian stimulation is primarily used in order to increase muscle mass and force gains in targeted muscles by stimulating the muscles into flexing repeatedly. The apparatus 45 can utilize Russian stimulation in two different ways. The apparatus 45 can use the current approach of 10 seconds of stimulation followed by 50 seconds of rest for up to 10 minutes in order to strengthen the muscles in the neck. The stronger the neck muscles are the more resistance there will be by the neck to a force that could potentially cause a concussion. Many sports teams and leagues, including the National Football League (NFL) are currently using the practice of using strengthening exercises focused on the player's necks in order to minimize the risk or severity of concussions overall. The apparatus 45 could be used in place of these exercises or work tangentially alongside these exercises in order to create a stronger neck that would better protect any user from concussion or neck related injuries.

A second method of utilizing Russian stimulation would be to use the same frequency in order to stimulate the muscles for a short period of time immediately after a strong force subjected to the user's head 51b is detected. When force sensors 46 detect a force greater than the maximum allowed safe force the apparatus 45 would send a current through the desired areas of the neck to stimulate those muscles. This would reduce the acceleration of the neck along with the acceleration of the brain causing the severity of the concussion to decrease. The apparatus 45 could use the force sensors 46 located in various locations to determine where the stimulation is necessary, or the stimulation could be applied to the entire neck. The onboard control system 67d would calculate the most effective muscles to stimulate.

Aussie Stimulation, another type of BMAC, is similar to Russian stimulation except it uses 1000 Hz frequencies instead of the 2500 Hz frequency Russian stimulation utilizes. Recent studies have shown that using the frequencies suggested by the Aussie stimulation create 71.7% torque compared to the Russian torque of 50.8%. Depending on the level of stiffness the microcontroller 67d calculates should be used the apparatus 45 can stimulate an alternating current at either frequency.

Pulsed Currents use a pulse of high voltage to stimulate muscle rather than the alternating current Russian and Aussie stimulation use. Recent studies have shown that a pulsed current with a voltage of 200 volts produce roughly the same amount of torque in the muscle as Aussie stimulation, around 70.1%. A pulsed current using a voltage of 500 volts producing a larger torque of 76.9% as shown by recent studies.

IFC similar to TENS is used to decrease pain while also increasing blood flow and circulation to the affected areas. The major difference between the two is the frequency at which the current is applied. IFC, either 2 or 4 polar frequency (difference in cycles per second), usually runs at a higher frequency of 4000 Hz while TENS runs around 125 Hz. The difference in frequency changes which nerve fibers are blocked from either sending or receiving the pain signals from the muscle. The apparatus 45 could, just like the TENS application, use a higher current to reduce pain in the neck of the user 51 caused by a previous trauma or other reason. IFC would generally be used in the same way to TENS, but IFC is known to deliver currents with much more comfort to the user 51. IFC could also be used by the apparatus 45 in order to reach a much greater depth or deeper muscle tissue than TENS could typically reach. IFC would be used to reach tissue located between the positive and negative electrodes 110 applied to the skin.

BMACEP would be a combination of an Aussie or Russian stimulation used in a high voltage pulse setting. BMAC stimulation along with pulse stimulation is currently only used to increase muscle mass by creating a cyclic pattern to test and then rest the muscle. The apparatus could use BMACEP in order to apply a high voltage pulse with a Russian or Aussie frequency for an elongated period of time. The extra time would keep the muscles stimulated after a force is detected by the apparatus 45 until the user 51 is determined to be no longer in any danger. The pulse could be set to last a predetermined amount of time or an automatic feature could be used by the microcontroller 67d. The automated elongated pulse time would be the time from when the sensors 46 initially record the extreme force until when the apparatus' accelerometers 46 record the user 51 has finally come to rest. A maximum time the elongated pulse would be applied would be built into the microcontroller 67d along with a kill switch 67b on the microcontroller 67d.

Alternatively, the electrodes 110 may all be stimulated simultaneously if the microcontroller 67c detects a large force. Instead of providing enough muscle support to just dampen the motion of the user's head 51b this will stiffen all muscles in the neck and upper torso creating one rigid body for the force to act upon. Utilizing Newton's law of motion, force equals mass times acceleration, the mass that the force is acting upon greatly increases which in turn will significantly reduce the acceleration of the user's head 51b thus minimizing the severity or even eliminating the resulting concussion.

The electrodes 110 have to be placed on very precise muscle locations in order to achieve maximum contraction. A physician or trainer could apply markers to the desired locations and record the locations in the external database 47 (FIG. 38) for future reference. The locations could also be determined from software using the information in the database 47 recorded about the particular user. The electrode 110 locations could be marked using washable or semi-permanent tattoos. A mark on the surface of the skin could be removed by the user after the electrodes 110 are placed, or a semi-permanent tattoo could be placed in the epidermis above the dermis layer where any mark would become permanent. Such marks would be gone in 3 to 4 weeks when the epidermis has regenerated.

Studies have shown that the brain does not have the time necessary to contract the neck muscles after a large blow to the head. As a large force is applied to the head the acceleration will be at a maximum. The acceleration would constantly be recorded by the sensors 46. The microcontroller 67d would read the accelerations measured by the sensors 46 and if the acceleration measured is greater than a predetermined allowable maximum the microcontroller 67d would activate the electrodes 110. In order for the microcontroller 67d to process the accelerations fast enough a very simple code would be used. All accelerometer values would be sampled by the microcontroller 67d in small increments (milliseconds or smaller). These values would run through a simple code that only has two conditions, if a sample size is greater than or equal to the predetermined max execute electrodes 110; or if less than, continue sampling.

As the sample increment decreases the power consumption will increase decreasing the battery life. Kinetic energy by the user or solar energy could be utilized to charge the power supply as well as rechargeable and replaceable batteries. To decrease the amount of time between the impact and the shock discharge each electrode could have their own capacitor which would be used to create the charge. These capacitors would still be connected to the main battery which would recharge the capacitors once they were released.

FIG. 38 is a table depicting a listing of the external database 47 that will allow the user 51 to interact with and change settings of the neck supporting apparatus 45. This database 47 will allow for any inputs necessary to develop a precise and effective method of muscle stimulation for any purpose. Such variable inputs include, but are not limited to, those listed herein or in FIG. 38. Desired Use (Line 1) gives the user, physician, trainer, or assistant the ability to select what the neck supporting apparatus 46 will be used for including, but not limited to, concussion prevention, therapy, massage, and training. There may also be a designation for specific activities or sports (Line 2) which will help determine the amount, placement, and settings for any included electrodes. Depending on the selections for these settings, the following options may become fixed or editable to ensure proper use of the device. The User Characteristics section (Lines 3-12) asks for input of physical characteristics such as age and weight, which factor into calculations for the electrode settings. It is also possible to input the name of the user so that personal settings may be saved and identified. Sensor Characteristics (Lines 13-14) may be altered based on the type of sensor to be used in the neck supporting system and on the level of precision desired. The Muscles to be Stimulated section (Lines 15-23) may include particular muscles that the user 51 desires to focus on. Certain muscles or muscle groups may be isolated to ensure proper contraction reactions to impact forces or to allow for focused therapeutic and training sessions. This device may then show the user the precise locations to place the electrodes 110 in FIG. 37 as determined by the user inputs from the external database 47. The Electrode Settings section (Lines 24-28) includes such variables as the frequency and intensity of the current to be utilized by the electrodes 110. The user 51 may also select different modes (Line 25) such as burst, continuous, pulsed, and sinusoidal. Certain settings may be preferred during therapy based on user 51 comfort, but specific modes will be required and not editable if concussion prevention is selected as the desired use. For instance, it may be determined that a short pulsed mode gives the most desirable muscle contraction, so the mode selection will not be editable. The user 51 may also be able to leave feedback (Line 29) on the database so that the user 51 and anyone else who may utilize the device may gain insight into such things as how well certain settings worked or what options to pay attention to when setting up the device.

The apparatus 45 could provide data using Bluetooth or any other method of wireless communication to a computer, tablet, smartphone as well as a smartwatch from a wireless communicator 49 located on the neck apparatus 45 (FIG. 37). The apparatus would be housed with many sensors 46 (FIG. 37) which may include accelerometers and health sensors that could be able to measure heart rate, blood pressure, distance travelled, blood sugar, cholesterol, calories burned, breathing rate, hydration, blood oxygen saturation and other data. Knowing the location, velocity, acceleration as well as the heart rate of the user 51 at all times could lead to very precise calculations of calories burned along with more intricate calculations and data such as which muscles have been used and what muscles should be worked out in future activities. Software specifically designed for this apparatus could be viewed live on any device and would be recorded for future analysis by the user 51 into the external database 47. Third party software could also connect to the apparatus 45 to access the data provided by the apparatus 45. The apparatus could also use data entered by the user 51 about previous neck or head injuries into the external database 47 in order to not only monitor those areas, but also take preventative action against further injury to those areas. The external database 47 may also be stored online or in the cloud and be accessed by any device with a wired or wireless connection.

Figure 39:
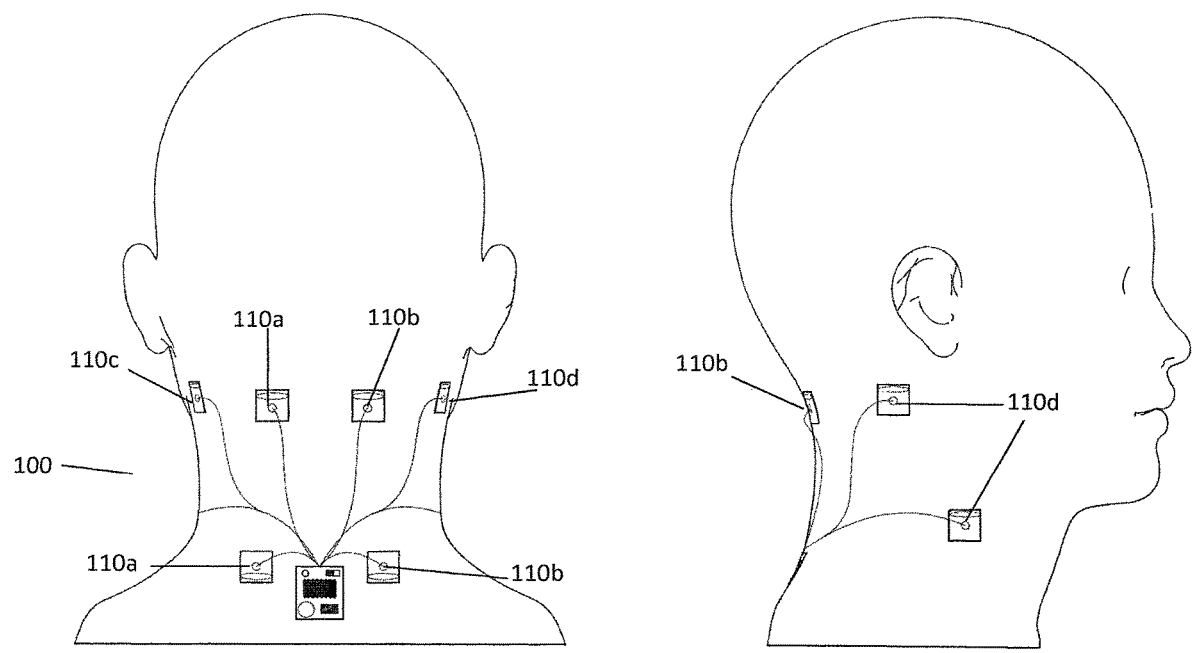
FIG. 39 depicts an embodiment of the neck supporting apparatus using electrical stimulation to stimulate both the trapezius and sternocleidomastoid muscles both from a rear and profile perspective.

FIG. 39 depicts an embodiment of the muscle stimulating neck supporting apparatus 100 similar to that of FIG. 37 but with a larger array of electrodes 110. The electrode pairs shown in this embodiment are placed vertically along the left electrode 110a and right electrode 110b to stimulate the trapezius muscles and along the left electrode 110c and right electrode 110d to stimulate the SCM muscles. The contraction of the trapezius muscles will dampen the flexion and extension of the head while the contraction of the SCM muscles will dampen rotation and lateral motion.

Figure 40:
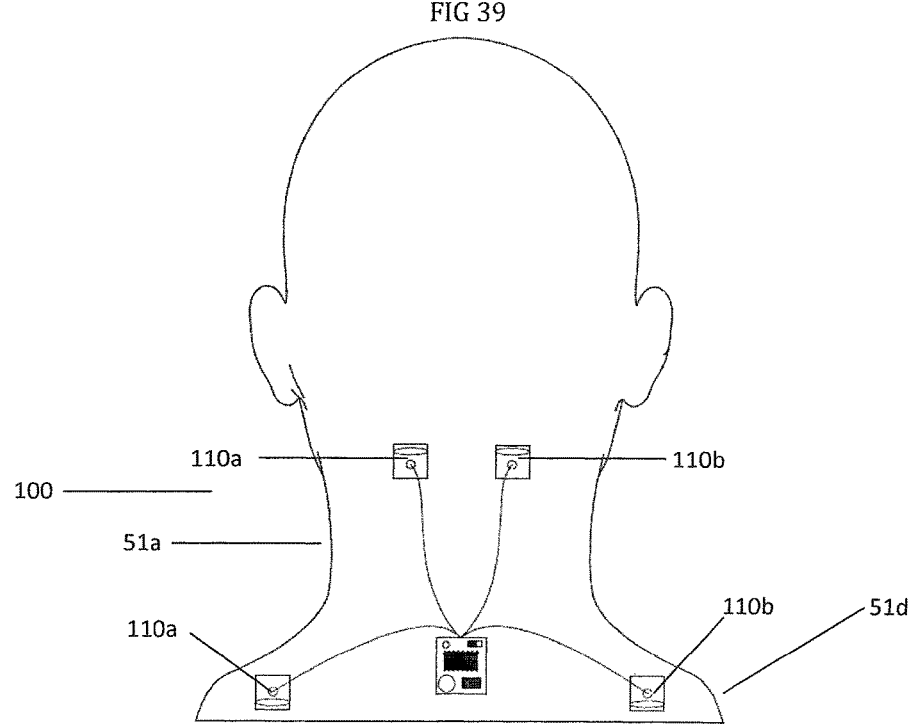
FIG. 40 depicts an embodiment of the muscle stimulating neck supporting apparatus used to stimulate the shoulder muscles.

FIG. 40 depicts an embodiment of the muscle stimulating neck supporting apparatus 100 similar to that of FIG. 37 but with electrodes placed closer to the shoulders 51d. The left electrode pair 110a and right electrode pair 110b both have upper electrodes close together at the upper portion of the trapezius muscle, while their pairs are placed lower down and spaced more widely to engage with lower fibers of the trapezius. The contraction of longer, wider reaching fibers of the trapezius will cause the shoulder blades (not shown) to rise in a motion similar to shrugging the shoulders. In addition to the dampening effect caused by the contracted muscles, the rise of the shoulder blades would reduce the effective length of the neck 51a, thereby decreasing the neck's range of motion and further dampening the motion.

Figure 41:
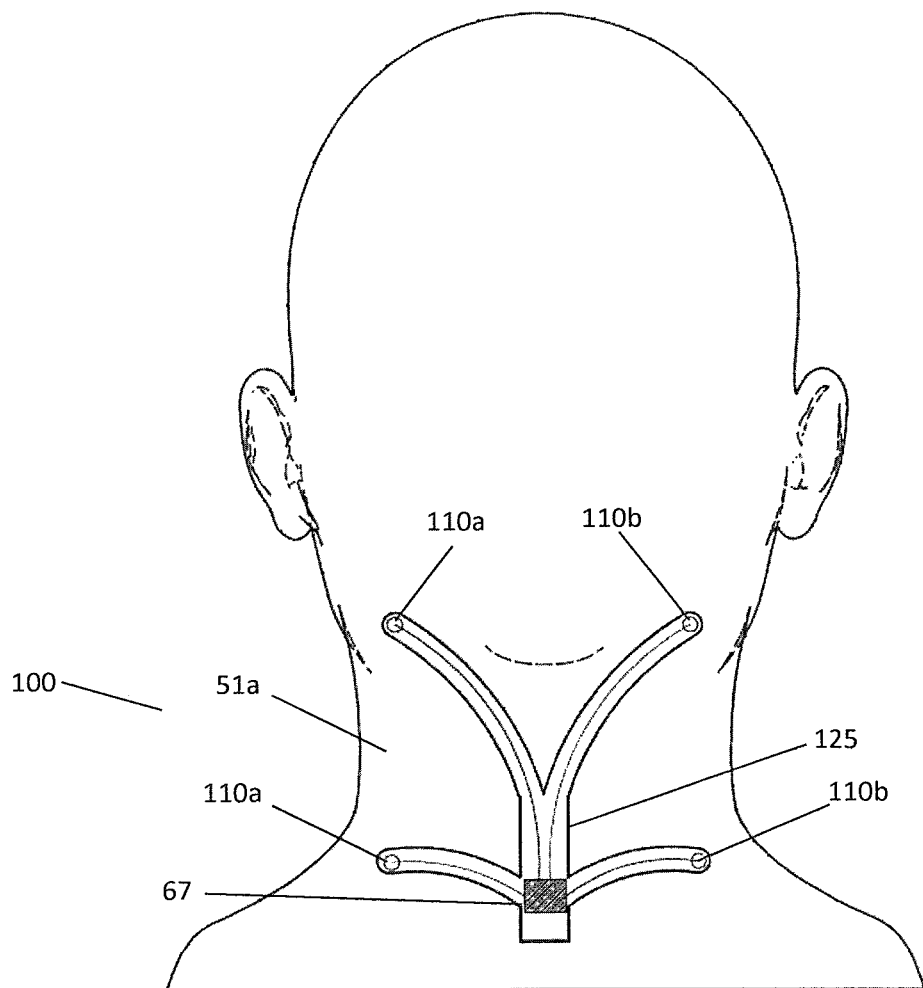
FIG. 41 depicts an embodiment of the neck supporting apparatus using electrical stimulation comprised of flexible electronics.
Figure 42:
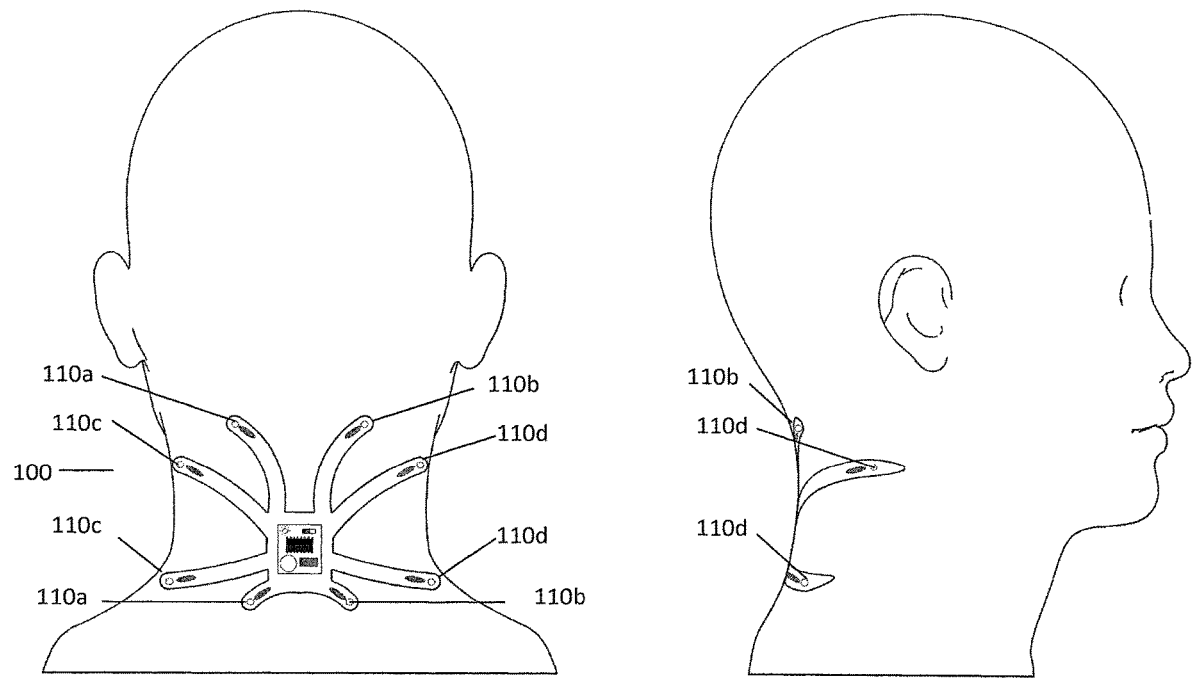
FIG. 42 depicts an embodiment of the neck supporting system using electrical stimulation comprised of flexible electronics and stimulating both the trapezius and sternocleidomastoid muscles.

Another embodiment of the muscle stimulating neck supporting apparatus 100 is shown in FIGS. 41 and 42 wherein the electrodes 110a and 110b are joined to the control system 67 by flexible electronics 125. The flexible electronics 125 will allow the circuitry to conform more closely to the user's body 51 and move with the neck. An adhesive layer (not shown) will allow the structure of the apparatus 100 to be positioned as desired. Further, the control system 67 will be able to flex and will lie flush to the user's neck 51a. FIG. 41 shows the flexible electronics 125 connecting electrode pairs for the left and right trapezius muscles with electrodes 110a and b. The overall structure of the flexible electronics 125 is flat and spider-like or web-like, allowing the electrodes to branch out from the control system 67 and conform readily to the neck 51a without adding bulk or appreciable interference. The given shape will also be such that when the control system 67 is positioned properly the flexible electronics 125 will be configured to automatically lie against the neck 51a. FIG. 42 depicts a similar trapezius electrode 110a, b placement with the addition of the SCM muscle electrode 110c, d placement.

Figure 43:
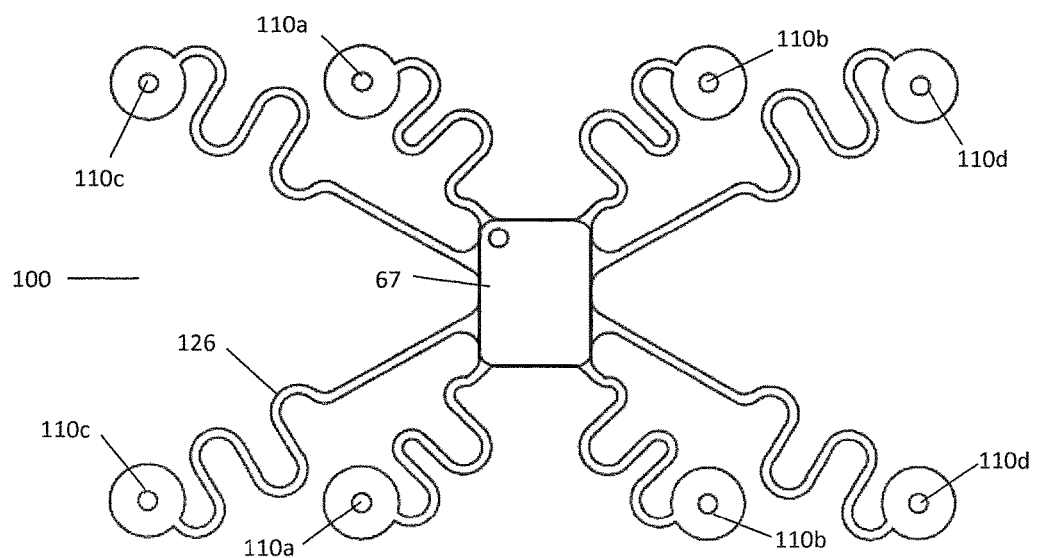
FIG. 43 depicts an embodiment of the muscle stimulating neck supporting system with sinusoidal shaped flexible, extensible electronics.

FIG. 43 depicts an embodiment of the muscle stimulating neck supporting apparatus 100 with sinusoidal shaped flexible, extensible electronics 126. The connections between the control system 67 and the electrodes 110a-d may have coiled, corrugated, sinusoidal, s-shaped, v-shaped, or other geometric patterns, which will allow them to expand or contract with the user's (not shown) movements. This will also allow the supporting apparatus 100 to engage with a variety of users in a large range of positions.

Figure 44:
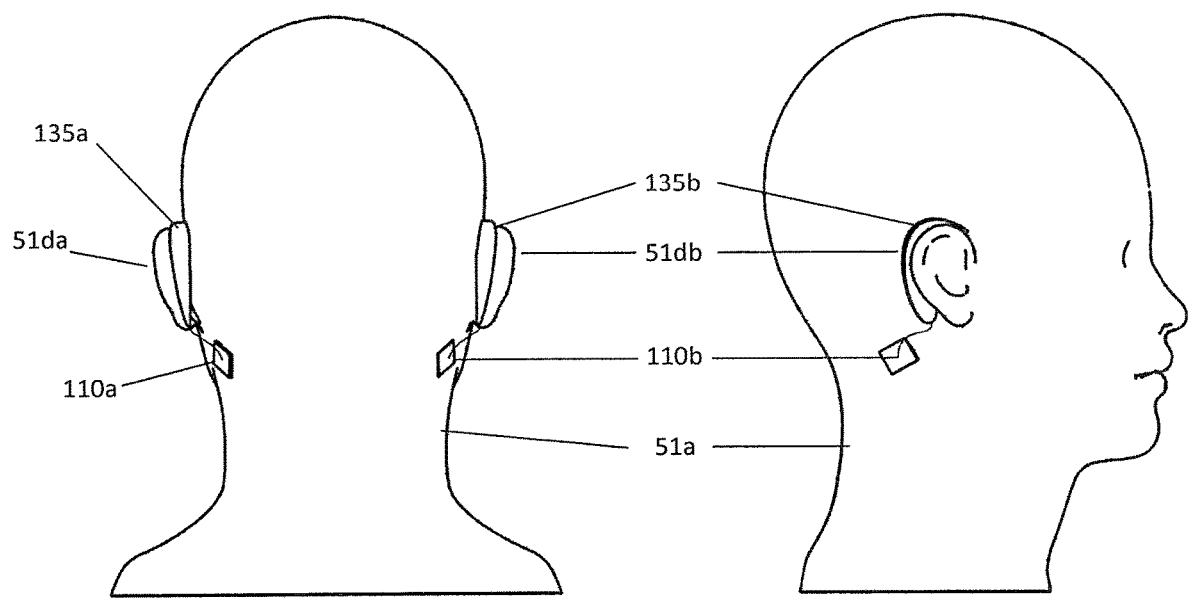
FIG. 44 depicts an embodiment of the muscle stimulating neck supporting apparatus utilizing ear mounts.

It is crucial that the user 51 be able to align the neck supporting apparatus 45 properly for the electrical stimulation to have the desired effect. It may be desirable to utilize anatomical landmarks, such as the ears, jaw, clavicle, or the spinous process or another portion of the spine, as markers or reference points from which to position the structure. Positioning off of these areas may be done be feel, by sight, by shaping the structure to fit certain areas, or by adding an attachment that will aid the user 51 in placing and positioning the apparatus 45 and then be either folded away or removed. FIG. 44 shows an embodiment of the neck supporting apparatus 45 with ear mounts 135*a, b*. The ear mounts 135*a, b* may contain any feature of the control system 67 (not shown) mentioned above and be able to communicate wirelessly with a user interface 52 (not shown) or external database 47 (not shown). The ear mounts 135 will also conform readily to the shape of the user's ears 51*da* and 51*db*, which will make the device be more out of the way and comfortable. Because the ear mounts 135 are engaged with a specific part of the anatomy, they may also serve as a stable platform with fixed positioning that will make it easy to position the electrode patches 113*a, b* which may include any electrodes, adhesives, sensors, and other features that may be needed for proper stimulation. The placement of a left ear mount 135*a* and right ear mount 135*b* will allow electric stimulation to flow easily across the user's neck musculature 51*a*.

Figure 45:
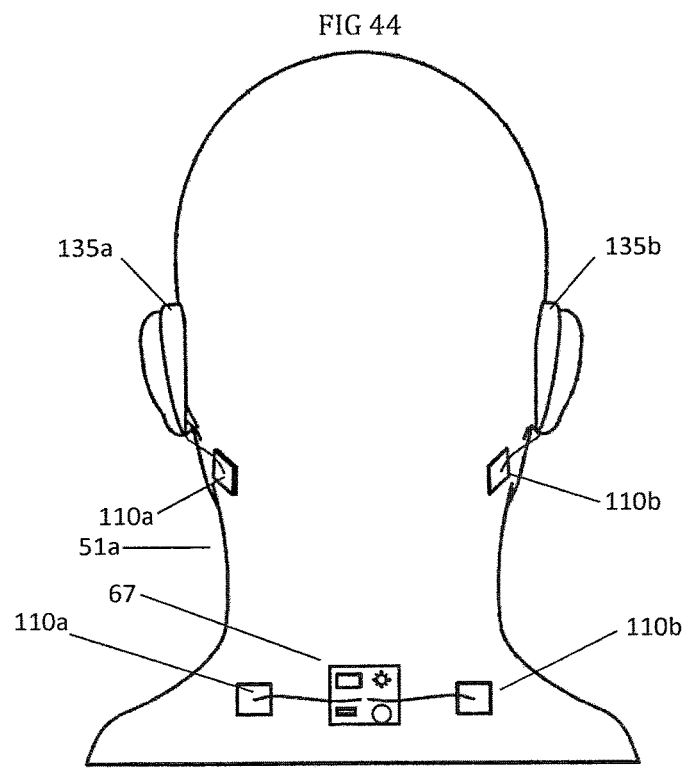
FIG. 45 depicts an embodiment of the muscle stimulating neck supporting system utilizing ear mounts and a separate electrode structure.

FIG. 45 shows the neck stimulation apparatus 100 embodiment of FIG. 37 wherein the ear mounts 135*a,b* are used in conjunction with an electrode structure including trapezius electrodes 110*a, b* and a control system 67. This embodiment would allow for both easy attachment using the ear mounts 135*a, b* and full electrical stimulation of the neck 51*a*.

Figure 46:
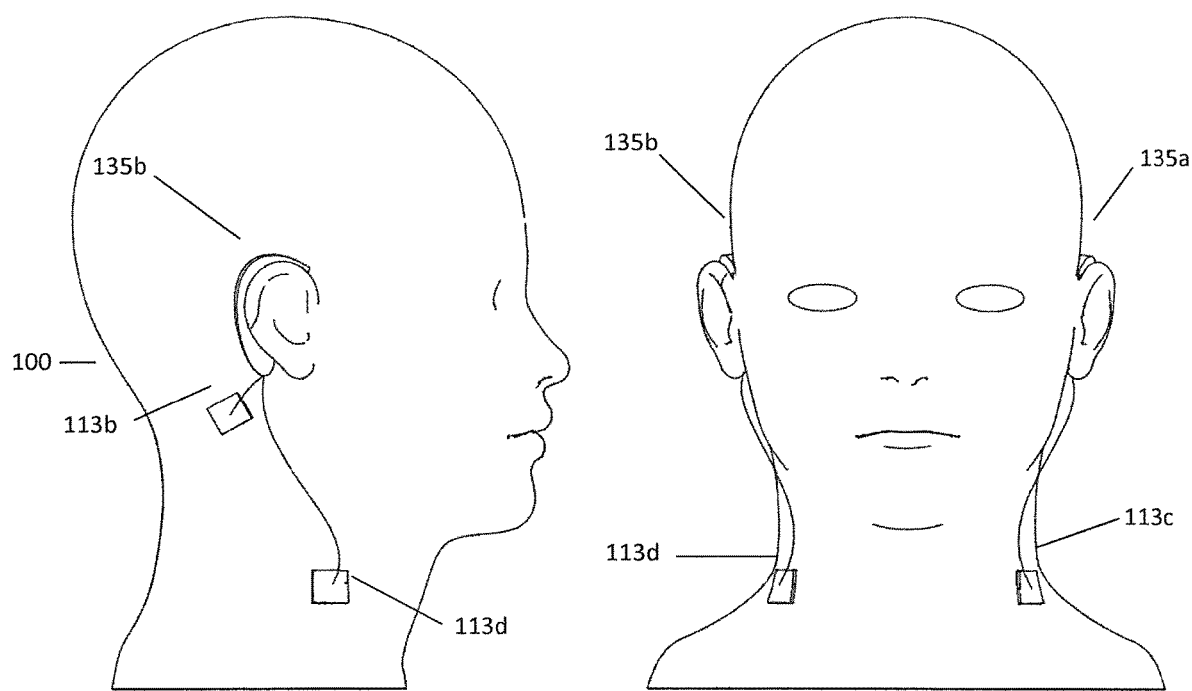
FIG. 46 depicts an embodiment of the muscle stimulating neck supporting apparatus utilizing ear mounts and targeting the sternocleidomastoid muscles.

FIG. 46 shows the neck stimulation apparatus 100 embodiment of FIG. 37 wherein the ear mounts 135*a,b* are targeting the full SCM muscles using left and right upper SCM electrode patches 113*a, b* and right and left lower SCM patches 113*c, d*.

Figure 47:
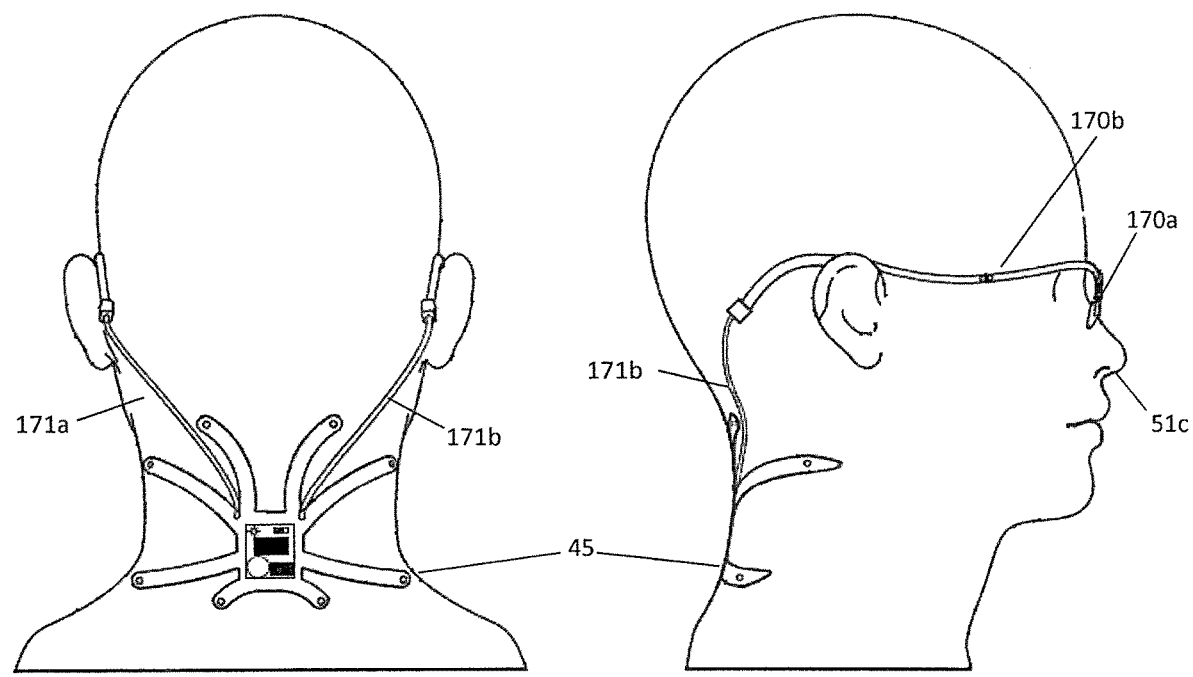
FIG. 47 depicts an embodiment of the neck supporting apparatus being placed using a supporting frame both from a rear and profile perspective.

An alternative method for the utilization of anatomical landmarks for positioning is shown in FIG. 47. A supporting frame 170, such as would be used for eyeglasses, including a nosepiece 170*a*, that lets the frame 170 sit firmly and comfortably on the user's nose 51*c*, and temple supports 170*b*, which are supported by and may curve slightly around the user's ears 51*d*, may engage with any neck supporting apparatus 45 embodiment that must be positioned accurately. This figure shows the supporting frame 170 engaged with the muscle stimulation apparatus 100 of FIG. 42 via connecting cords 171*a* and 171*b*, which may engage and disengage with either the frame 170 or system 100 as needed. The frame 170 and connecting cords 171*a, b* allow the apparatus 100 to be oriented correctly for every use because it guides the structure to lay against the neck 51*a*. Once the muscle stimulation apparatus 100 has been placed and engaged with the neck 51*a*, the connecting cords 171*a, b* may detach to allow the supporting frame 170 to be removed. Alternatively, the frame 170 may remain attached, and optionally included features such as lenses or a digital display system may act as a user interface 52 (not shown) so that the user 51 may be able to view real time data output from the apparatus 45.

Figure 48:
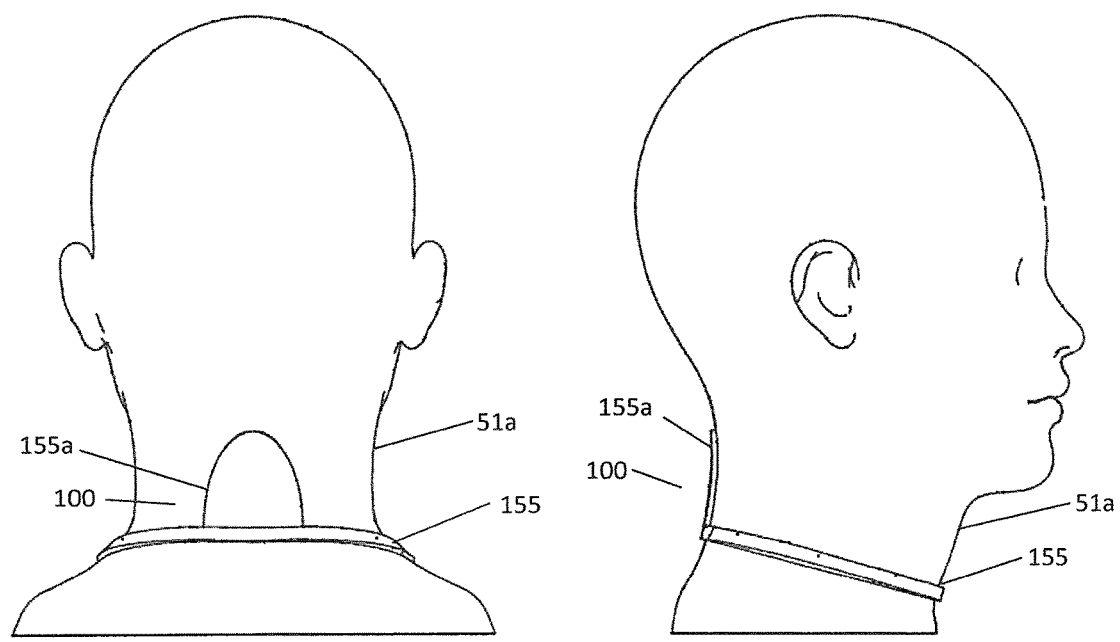
FIG. 48 depicts a neck band that may hold all features of the neck supporting apparatus.
Figure 49:
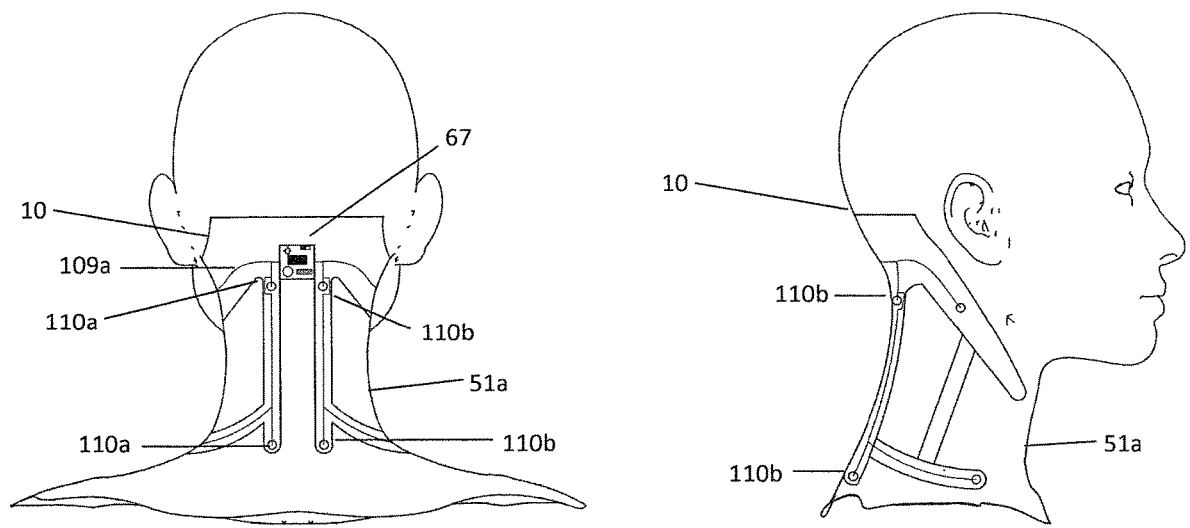
FIG. 49 depicts an embodiment of the neck supporting apparatus from FIG. 8 with the addition of muscle stimulation both from a rear and profile perspective.

FIG. 48 depicts an embodiment of the muscle stimulation neck supporting apparatus 100 wherein a neck band 155 engages with the neck 51*a* to hold all necessary features of the apparatus 100 in position. The neck band 155 may fully encircle the neck 51*a*, or it may be open at the throat or reach only a small portion of the way around the neck 51*a*. The neck band 155 may then engage with the neck simply by encircling it and resting at the base, or it may conform to the neck, tighten down, or use some form of adhesive for engagement. A projection 155*a* at the back of the neck band 155 describes the location of the features necessary to fully utilize the apparatus 100 including, but not limited to, electrodes, sensors, a control system, and any other necessary circuitry. These features may also be embedded directly into the neck band 155. This embodiment would ideally be of a minimum size so that it may be light and unobtrusive to the user. Muscular stimulation may be combined with any of the other neck apparatus embodiments mentioned in this description. FIG. 49 depicts an embodiment of the neck supporting apparatus 10 from FIG. 8 enhanced by muscle stimulation. Embedded into the neck supporting apparatus 10 are electrodes 110*a-d*, a control system 67, wires 109*a-d*, and any sensors 46 (not shown) or other features necessary to allow the apparatus 10 to electrically engage with the neck musculature 51*a*. The stiffer supporting structure gives the user 51 support at all times, while the electrical stimulation protects against larger impacts or accelerations.

Figure 50:
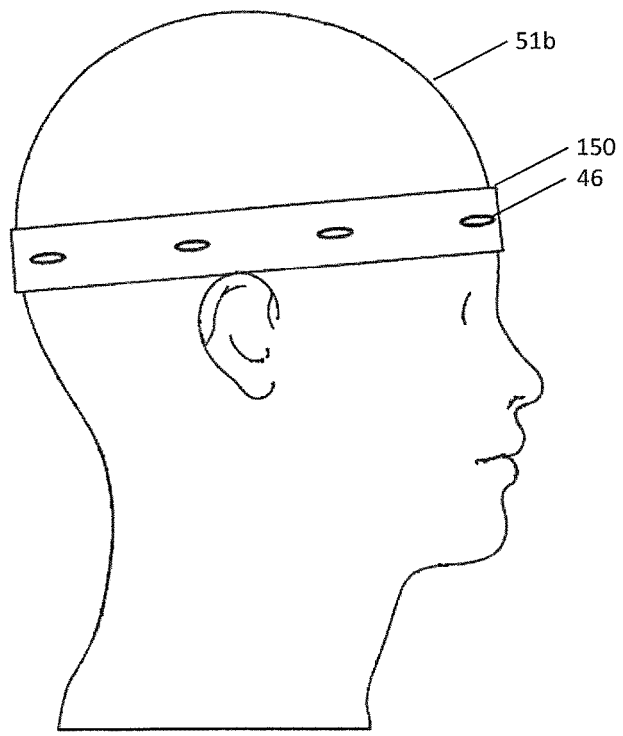
FIG. 50 depicts an embodiment of a headband with sensors.

FIG. 50 depicts a headband 150 to be worn around the user's head 51*b*. The headband 150 may be used in conjunction with any embodiment of the neck supporting apparatus 45 (not shown) described previously or subsequently and may include a series of sensors 46 that may communicate with other sensors 46 (not shown) or a control system 67 (not shown). The addition of the sensors 46 around the head 51*b* will provide a better understanding of the full motion of the head during use.

Figure 51:
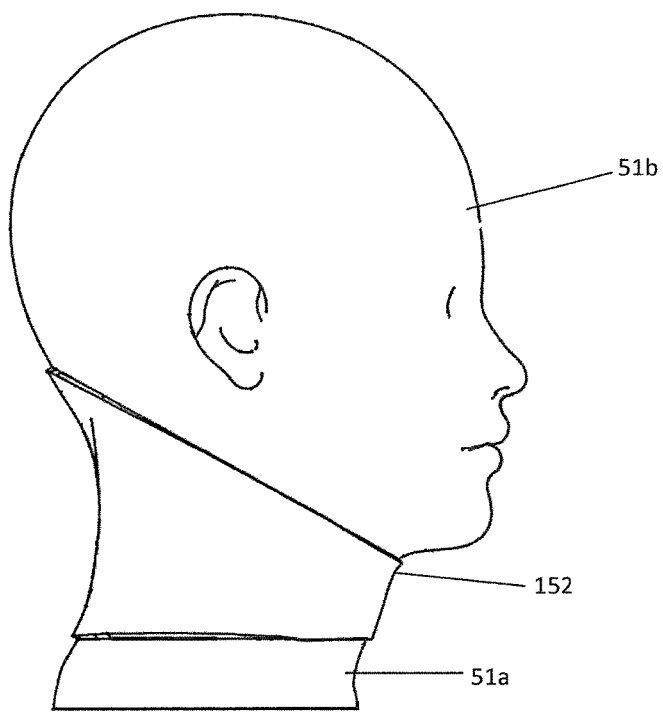
FIG. 51 depicts an embodiment of a collar that may cover the neck supporting apparatus.

FIG. 51 depicts a collar 152 which may be worn to cover any of the neck supporting apparatus 45 embodiments described previously or subsequently. The collar 152 may be any flexible material that is comfortable and breathable for the user 51 to wear, or it may be a garment or part of a garment already worn by the user 51 such as a shirt or jacket. The collar 152 may also be elastic so as to conform to the user's neck 51*a* or to allow it to be pulled over the user's head 51*b*. Alternatively, the collar 152 may have one or more zippers, buttons, hook and loop fasteners, or other methods or closure with which to secure it around the user's neck 51*a*. The collar 152 will cover any and all of the features of the neck supporting apparatus 45 mentioned previously, most importantly the muscle stimulation neck supporting apparatus 100 (not shown), with its included electrodes, microelectronics and conductive materials. The collar 152 will ensure that these features remain secured to their designated locations while protecting the user 51 and anyone else who may come in contact with the user 51 from being injured by potentially sharp, hard, or electrically active features.

Figure 52:
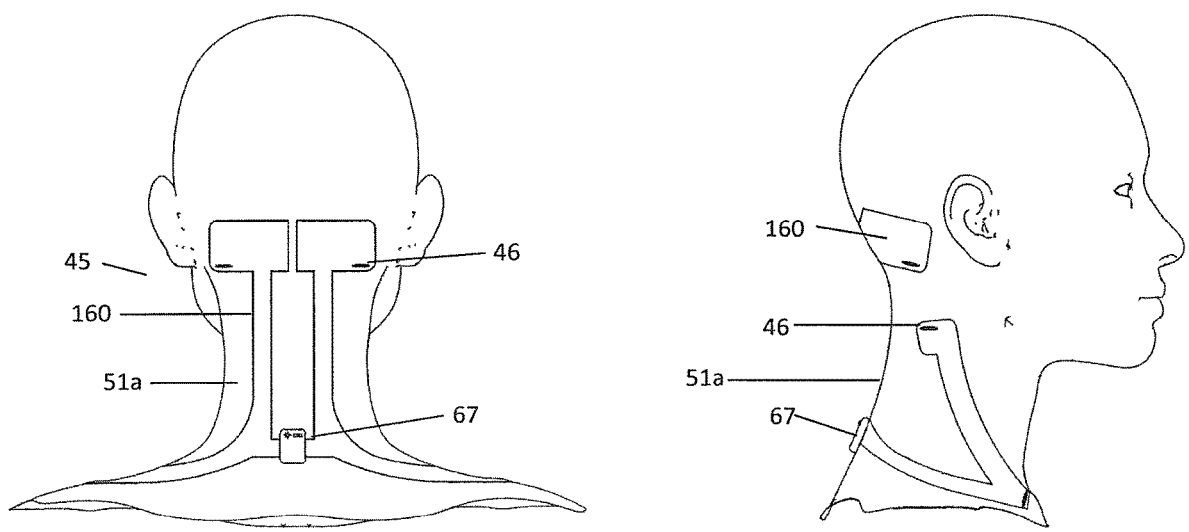
FIG. 52 depicts an embodiment of the neck supporting apparatus utilizing electroactive materials.

An embodiment of the neck supporting apparatus 45 may also utilize electroactive materials 160, as seen in the embodiment in FIG. 52. The main structure of the neck supporting apparatus 45 will be comprised of an electroactive material 160, which may be any polymer, fabric, or other material that will conform to the user's neck 51*a* during regular use but may change shape, size, or become rigid when stimulated by an electric field. When the sensors 46 detect a change in position, speed (velocity), acceleration, or force, the control system 67 may apply an electric current to the apparatus 45, thereby causing it to become a rigidly supportive structure. Once the sensors 46 show that the force has been mitigated, the control system 67 may deactivate the material 160, allowing the user 51 to regain full range of motion.

Figure 53:
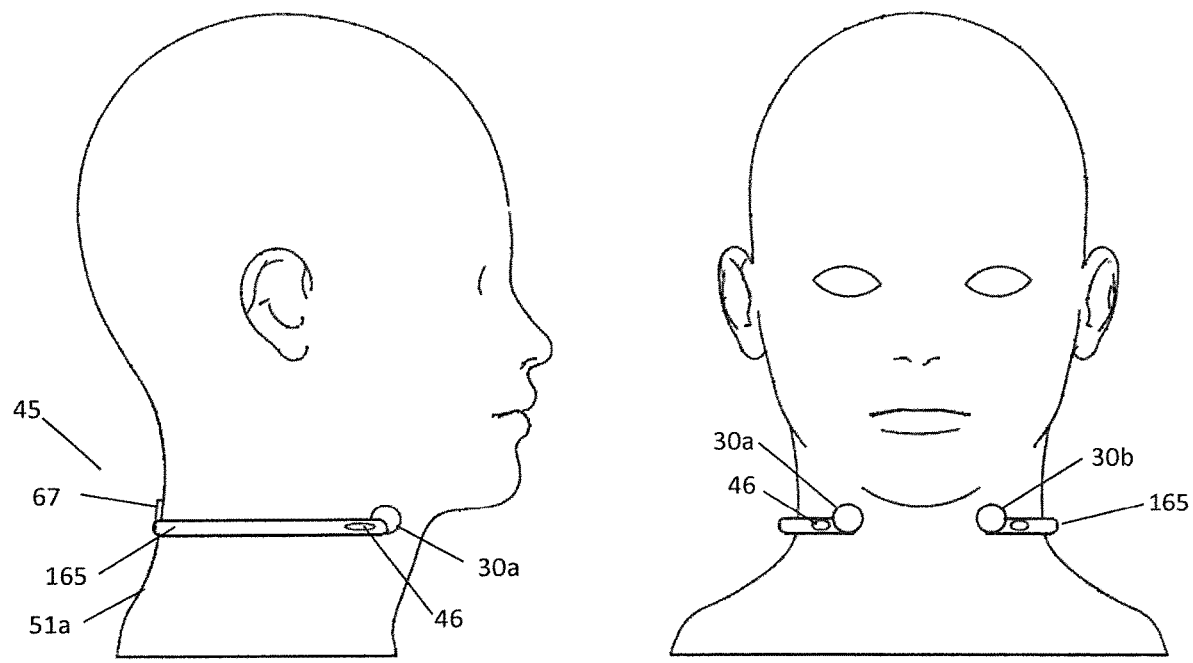
FIG. 53 depicts an embodiment of the neck supporting apparatus, wherein a shape memory alloy is utilized to vary intracranial pressure.

FIG. 53 depicts an embodiment of the neck supporting apparatus 45, wherein a shape memory alloy is utilized to vary intracranial pressure. This embodiment includes a shape memory actuator 165, which wraps around the user's neck 51a, a control system 67, and compression pads 30, which may be any size, shape, or material necessary to apply pressure to the jugular veins.

The shape memory actuator 165 will be comprised of a shape memory alloy which will be pre-formed to engage with the user's neck 51a so that the compression pads 30a, b apply light pressure to the jugular vein. A pressure sensor (not shown) embedded within the compression pads 30a, b may show the resulting cranial pressure increase. Other sensors 46, will track when forces are present. When these sensors 46 measure a large force, an alarm (not shown), which may be any beeper, buzzer, blinking light, vibrational alarm, or other means of drawing the user's 51 attention to the device, will engage. This will warn the user 51 that the control system 67 is going to activate an electrical current, which will flow through the shape memory actuator 165. This current will heat the shape memory actuator 165 slightly, thereby causing it to move to its secondary shape, which will have slighter compression on the neck 51a. Relieving the pressure on the jugular vein will allow the blood to flow freely and decrease intracranial pressure. This pressure reduction is crucial in order to reduce the risk of damage to the brain in the event of swelling due to an impact. After a specified time or when directed by the user 51, the control system 67 may disengage the electrical current so that the shape memory actuator 165 may bend back to its original, compressive position and begin to increase the intracranial pressure once again.

It may also be possible to increase intracranial pressure via contraction of the omohyoid muscle or another muscle in contact with the jugular vein. This embodiment might include electrical stimulation of the omohyoid muscle to contract the muscle and thereby constrict blood flow from the head. This may require the use of implantable electrodes so as to ensure the stimulation of the specific muscles.

These implantable electrodes may also include an implantable controller, though they need not be connected to the controller, but may be wirelessly connected to a controller that is not implanted.

When utilizing the muscle stimulation neck supporting apparatus 100, it may be desirable to control which electrodes 110 stimulate the musculature and when. When a relatively large force is detected, it may be beneficial to stimulate all of the muscles in the neck simultaneously, stimulate one muscle group at a time, or utilize some other combination.

Figure 54:
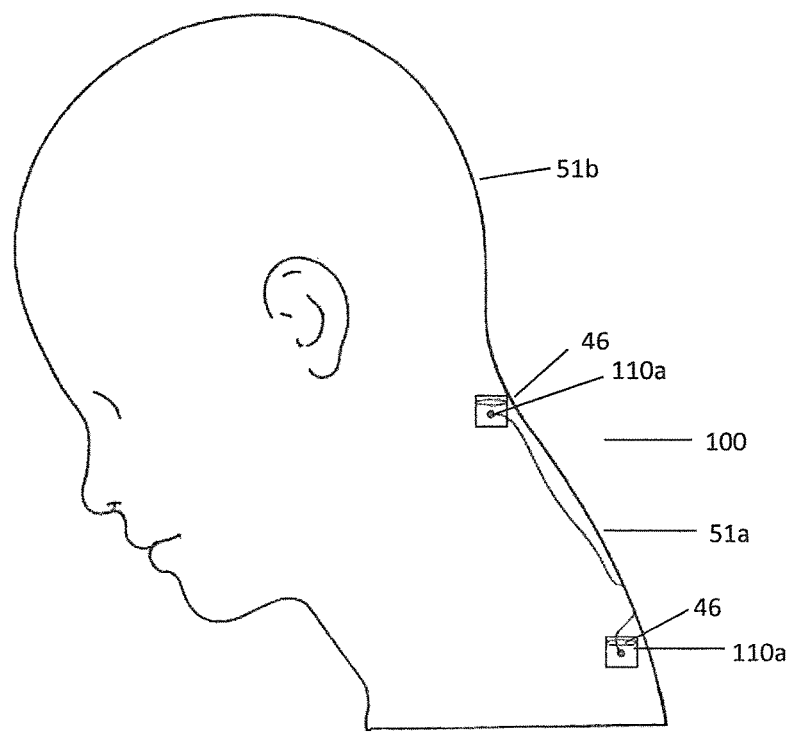
FIG. 54 depicts an embodiment of the neck supporting apparatus being used on a head in flexion.

FIG. 54 shows an embodiment of the muscle stimulation neck supporting apparatus 100 engaged with a head 51b experiencing ventral flexion, or forward bending. The range of motion for the average human head in ventral flexion is about 50 degrees. The extent of range of motion in ventral flexion is 50 degrees on average. When the sensors 46, either by acceleration, position, rotation, or other changes, detect that a relatively large force is causing flexion, the trapezius electrodes 110a and 110b (not shown) will engage with the superior and middle fibers of the trapezius muscle, or the Levator scapulae which will contract as if it means to cause extension, or backward bending, of the head 51b. If the intensity of the electrical stimulation is large enough, the current may reach deeper into the tissue, thereby also engaging smaller extension muscles including the Splenius Captivis and Cervicis and the Semispinalis Captivis and Servicis.

The electrodes 110a,b may be engaged fully for a set amount of time, or they may increase or decrease in intensity or pulse on and off depending on the desired muscular reaction. Pulsation may be desirable because it would allow the muscle to contract to dampen the impact force and then relax to reduce muscle damage and allow the neck 51a to realign naturally.

Figure 55:
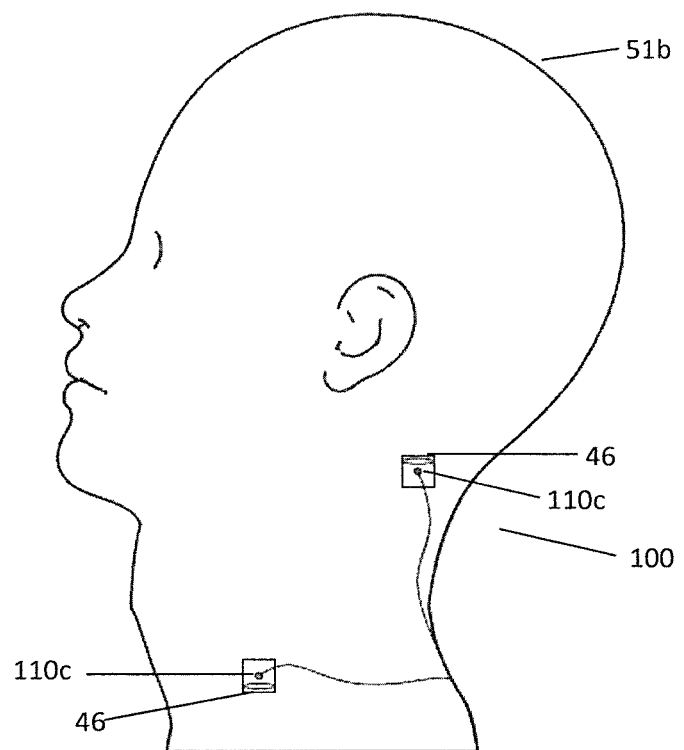
FIG. 55 depicts an embodiment of the neck supporting apparatus being used on a head in extension.

FIG. 55 depicts a similar embodiment of the muscle stimulation neck supporting apparatus 100 to FIG. 54 except now the head 51b is in extension. When the sensors 46 detect that a relatively large force is causing dorsal flexion, extension, or backward bending, of the head and neck, the electrodes of the SCM 110c will engage. The range of motion for the average human head in dorsal flexion, or extension is about 60 degrees. The extent of range of motion in dorsal flexion is 60 degrees on average. The SCM muscles or the Levator scapulae, along with other muscles including but not limited to the Longus Capitis and Colli and the Rectus Capitis Anterior and Lateralis, will contract as they would to cause flexion, thereby dampening the effect of the opposing extension.

Figure 56:
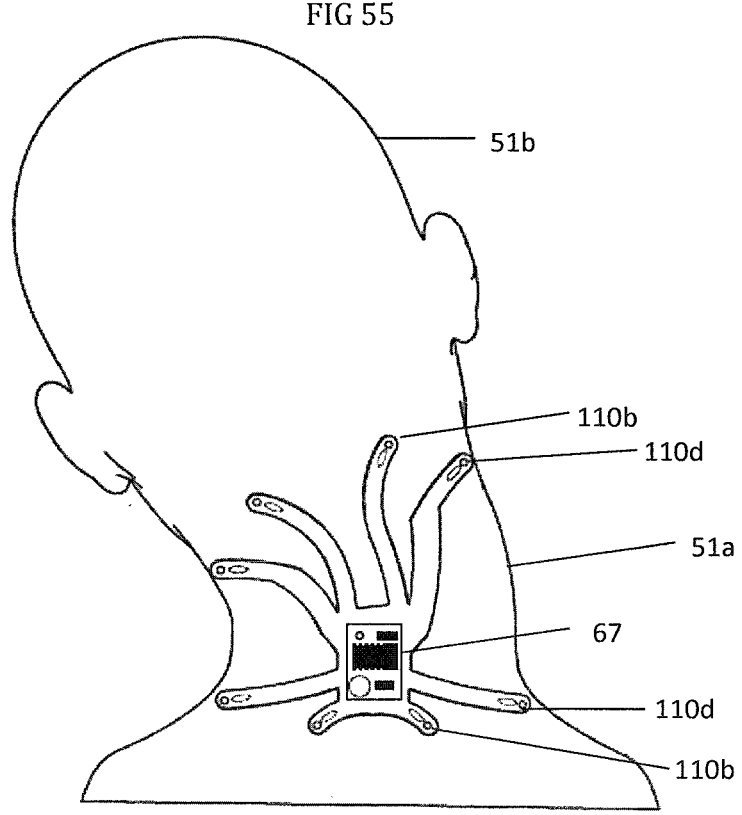
FIG. 56 depicts an embodiment of the neck supporting apparatus being used on a head in lateral flexion.

Similar to FIG. 54, lateral flexion of the head may require stimulation of certain muscles. FIG. 56 details lateral flexion of the head 51b to the left. When a large force causes this motion, the control system 67 may choose to engage only the right trapezius electrodes 110b and right SCM electrodes 110d, which will cause the above mentioned muscles of only the right side to contract and counteract the force. The same may be said for right lateral flexion, where only muscles on the left side of the neck 51a may engage. The range of motion for the average human head in lateral flexion is about 90 degrees. The extents of range of motion in lateral flexion is 45 degrees to the right and 45 degrees to the left on average.

It is noted that various ornamental shapes can be selected for the apparatus embodiments illustrated in the figures while still performing the same functionality. For example, there may be two, four, six, eight, or any number of electrode extensions out of the control center, making the apparatus look like a beetle, ant, spider ("neckspider"), or other known legged creature. Alternatively, the apparatus may take on a futuristic shape of a space ship or other science fiction article including metallic, pearlescent, or glowing materials, and led lights. Or the apparatus may take on the free form of the neck with natural skin-looking ("neckskin"), translucent, or transparent materials so as to be camouflaged or less apparent. These and other ornamental shapes may be selected or varied to improve the aesthetic appearance of the apparatus or to identify a source of the apparatus while still achieving the functionality of the apparatus.

Figure 57:
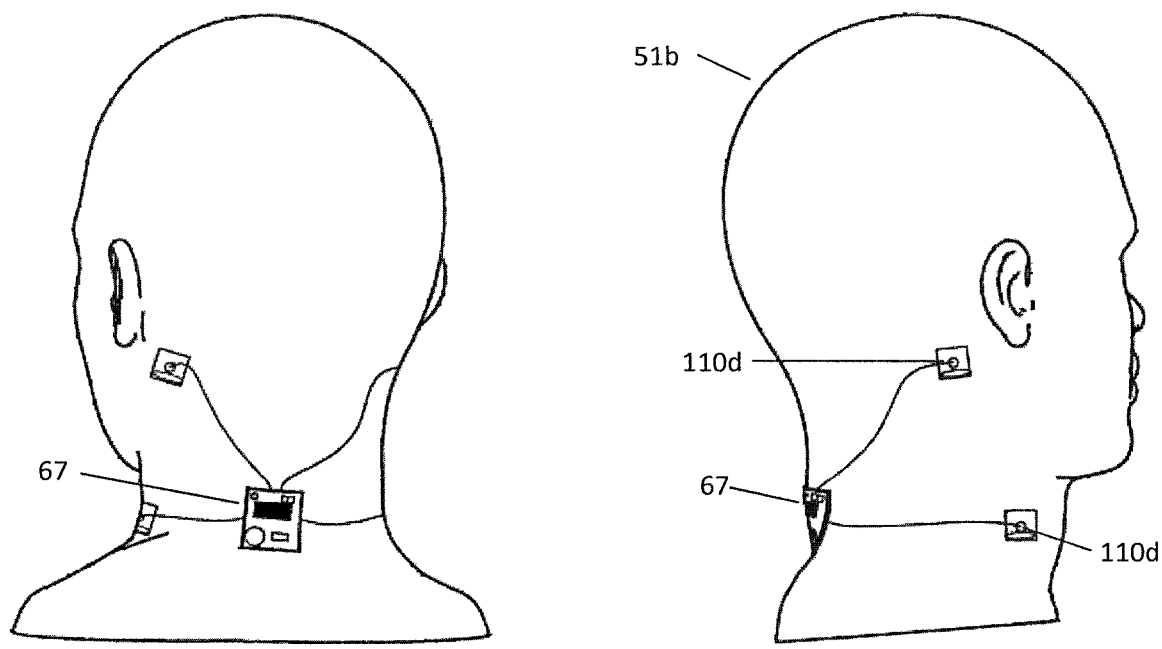
FIG. 57 depicts an embodiment of the neck supporting apparatus being used on a head that is rotated to the left both from the back and right side views.

In a similar manner to FIG. 54, rotation of the head 51b and neck 51a may require the stimulation of certain muscles. FIG. 57 details the rotation of the head 51b to the left. When a large force causes this motion, the control system 67 may choose to engage only the SCM electrodes 110d and/or other muscles on the right side such as the right trapezius, splenius capitis and cervicis, and the scalenes. The contraction of these muscles would cause rotation and lateral flexion in the direction opposite of the force, thereby dampening its effect and reducing the rotation. Similarly, rotation of the head 51b to the right will result in unilateral contraction of the left-side muscles. The range of motion for the average human head in rotation is about 160 degrees. The extents of range of motion in rotation are 80 degrees to the right and 80 degrees to the left on average. As mentioned previously, it will likely be necessary to include sensors 46 with the neck supporting apparatus 45 in order to better understand the motion of the user 51. Sensors 46 may be placed at any location on the user's 51 body that will aid in the understanding of the movement of the user 51. The sensors 46 may be placed at even intervals, at specified points, or they may be mounted to a garment or device that will be placed on the user 51 in a specified way. These sensors may also have the ability to track position, velocity, acceleration, jerk, rotation, or any other variable that will allow the control system 67 to understand how the head, neck, shoulders, and the rest of the body are moving relative to each other.

Because a user 51 experiencing jerk may be experiencing load changes faster than the user's 51 muscle control can compensate for, the sensors must have a very high sampling rate and short processing time to ensure that the apparatus 45 engages fast enough to dampen the forces.

Figure 58:
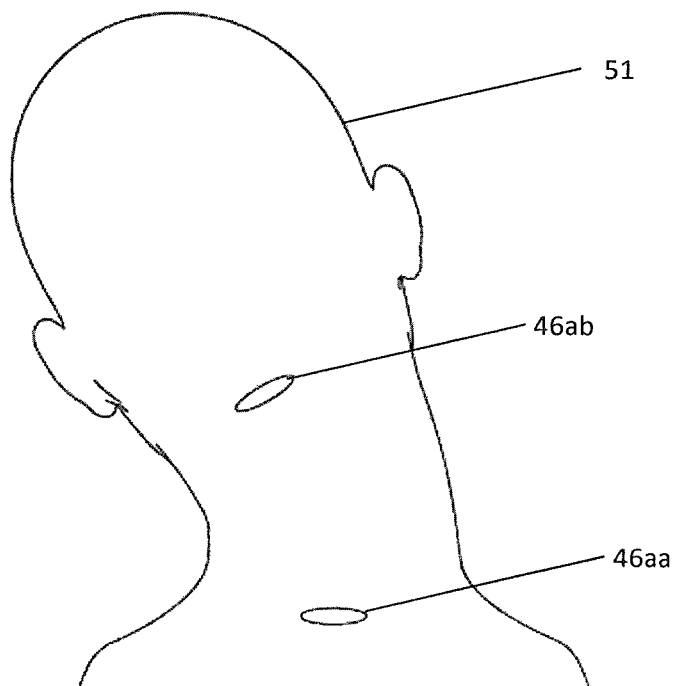
FIG. 58 depicts a possible embodiment of triaxial accelerometers used to measure the acceleration of the head and neck.

FIG. 58 illustrates one possible embodiment of sensor placements, wherein a triaxial accelerometer 46aa is placed at the base of the neck 51a and another triaxial accelerometer 46ab is placed at the base of the skull. The triaxial accelerometers 46aa and 46ab may measure accelerations on three different axes. These accelerometers 46aa,ab may work separately, simply sending overall acceleration data to the control system 67 (not shown), or their data may be compared. If the upper triaxial accelerometer 46ab shows a larger acceleration or jerk, which is the rate of change of acceleration, than the base triaxial accelerometer 46aa, then it would be clear that the head is experiencing a whiplash-like motion. The axes that show greater variance will tell the control system 67 (not shown) the direction in which the head 51b is moving relative to the shoulders 51d and allow the apparatus 45 (not shown) to react accordingly. Additional sensors may also be incorporated into the apparatus 45 (not shown) to track the user's 51 pulse, temperature, blood oxygen level or any other variables that may be desirable.

Figure 59:
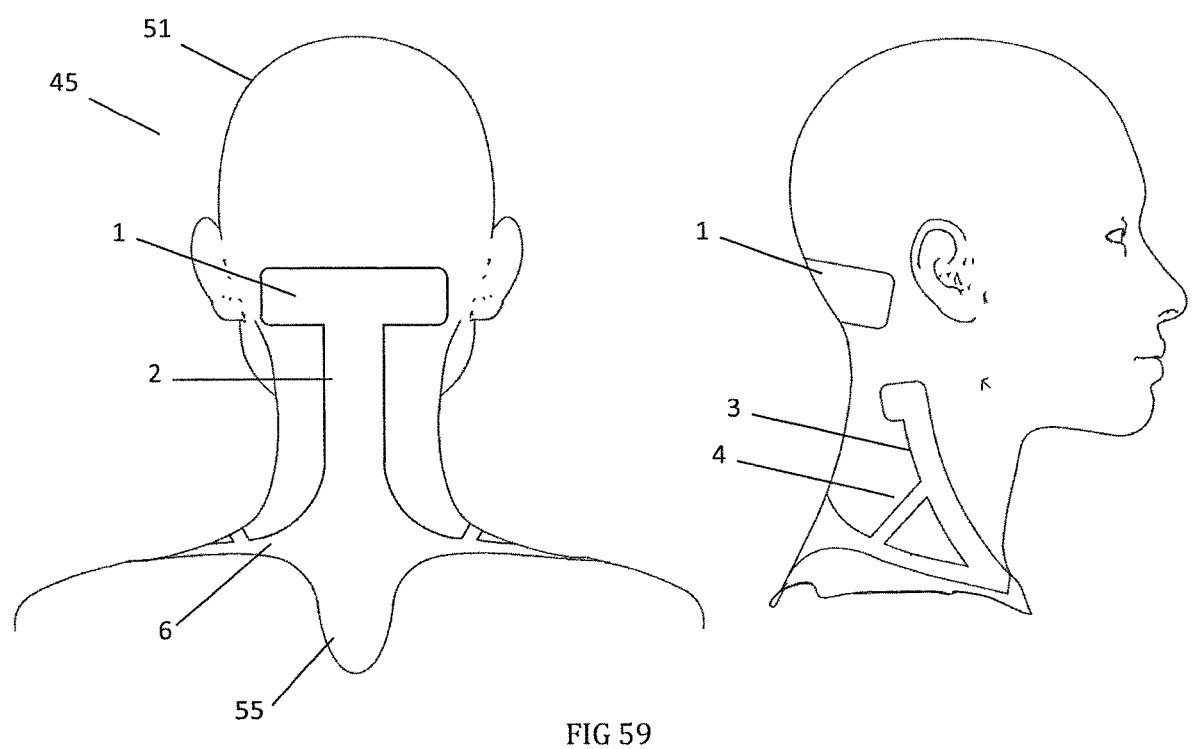
FIG. 59 is an embodiment of the neck supporting apparatus with reinforcement projections down the back.

FIG. 59 depicts an embodiment of the neck supporting apparatus 45 with head, shoulder, and upper back support. This embodiment is based at the shoulders 6 with a single large trapezius support 2 running from the base of the head support 1 downward. Similar to FIG. 9, the SCM supports 3 and the scalene supports 4 further reinforce the structure of the neck to protect from rotational and lateral motions. A back support 55 may extend as far below the shoulders as necessary to fully support the spine and the neck. The back support 55 may be as wide or as long as necessary, and it may be branched, curved, or shaped in any way to best mount the apparatus 45 and protect the user 51 from impact or strain.

Electrically stimulating a shoulder shrug prior to or during head acceleration can decrease the effective length of the neck thereby reducing the acceleration experienced by the head. Furthermore, the shoulders can act as a natural support or brace, limiting the heads motion or travel. Electrical muscle stimulation of the shoulder and neck can effectively induce a shoulder shrug. Experiments have been conducted to evaluate this technique with different electrical settings.

Figure 60:
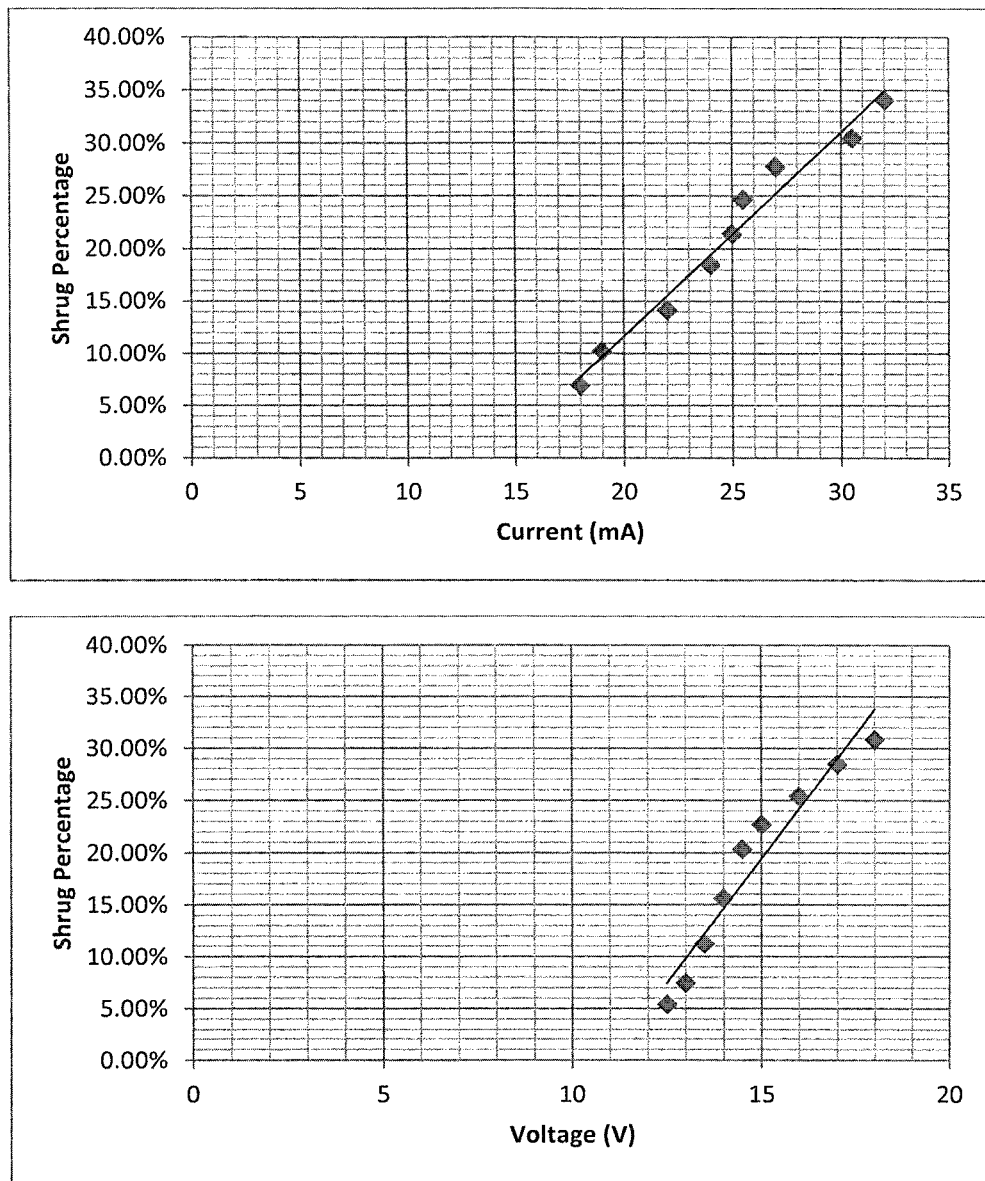
FIG. 60 is two graphs showing recorded values of shrug percentage as a function of current and voltage using interferential current stimulation. A trend line shows a linear progression.

The graph shown in FIG. 60 represents the shrug percentage achieved by stimulation over a range of milliamps (mA) or volts (V). An IFC setting was used for this data meaning a frequency of 4000 Hz. The data was obtained by measuring the length of shoulder movement at the same point on the shoulder over the entire range of milliamps or volts. The shoulders were then shrugged to a maximum height without any stimulation to find the maximum possible height which was used to calculate the shrug percentage. Since the shoulders do not move in a straight line and rather an arc approximations were made in measuring the maximum height which leads to a possible error of ±1.5%. Current less than 15 mA and voltage less than 12 volts created no stimulation. On both graphs a linear trend of shrug height can be seen as the current or voltage progressively increases followed by an immediate halt of any more increase. The following points were not graphed to show the trend line, but they can be seen in FIG. 61.

Figure 61:
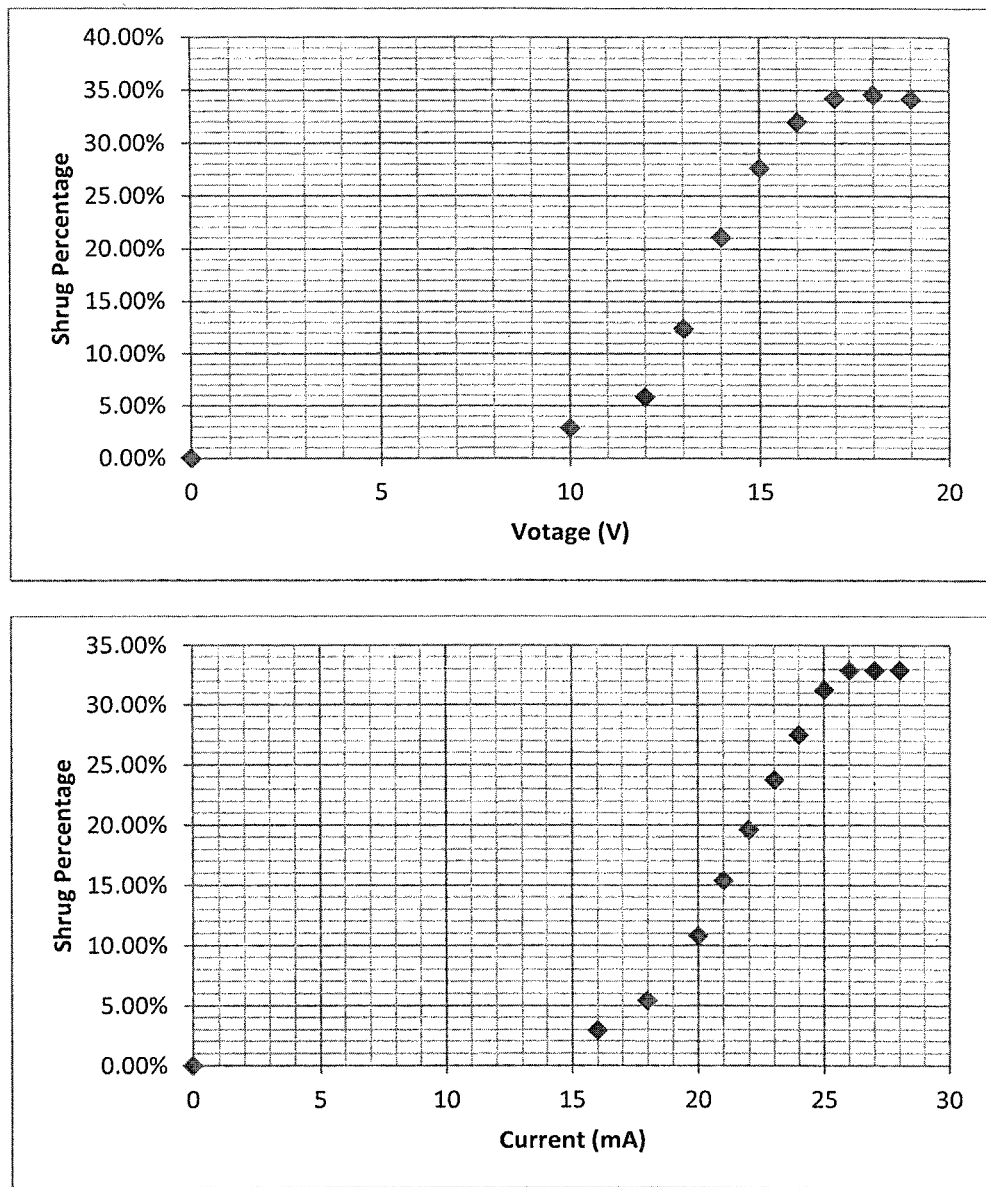
FIG. 61 is two graphs showing recorded values of shrug percentage as a function of current and voltage using Russian stimulation.

FIG. 61 shows a similar approach to the previous graph, but instead utilizes Russian stimulation. The frequency is set at 2500 Hz while both the voltage and current progressively increase. Using a lower frequency allows stimulation to occur at a lower setting while also creating a slightly higher shrug percentage at higher settings. Like IFC the shrug height tends to level off at a specific value depending on the frequency. The graph also includes a possible error of ±0.84%.

Figure 62:
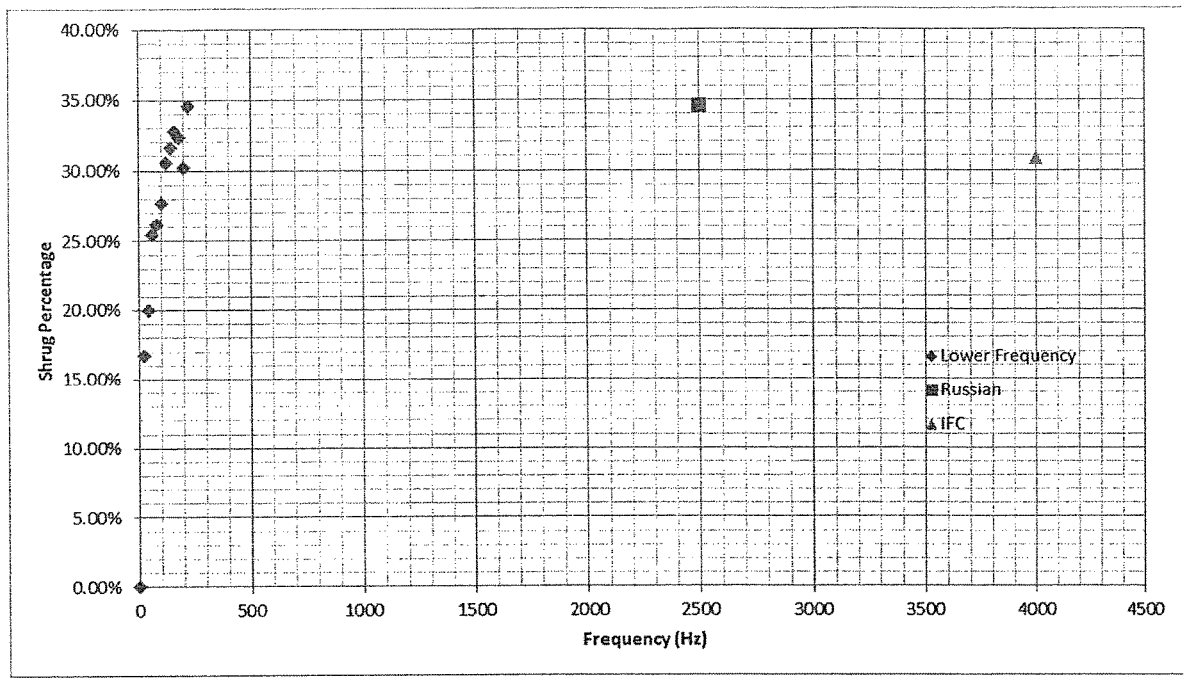
FIG. 62 is a graph showing shrug percentage as a function of frequency. A constant voltage pulse was used at each frequency.

The graph in FIG. 62 shows the shrug percentage as a function of frequency. Due to limitations of the stimulation equipment only a range between 20 and 220 Hz was achievable on the lower frequency range. All points were taken at a constant voltage of 18 V. Both the Russian and IFC points were taken from the 18 V values. Russian frequency and IFC frequency are always set to 2500 Hz and 4000 Hz respectively. The error for the lower frequency range is ±2.18%. The graph shows a possible maximum shrug percentage between the 220 Hz point and the 2500 Hz Russian stimulation point. This value is between 1000 and 1500 Hz which is consistent with the findings that an Aussie Stimulation of 1000 Hz creates the highest possible torque.

Figure 63:
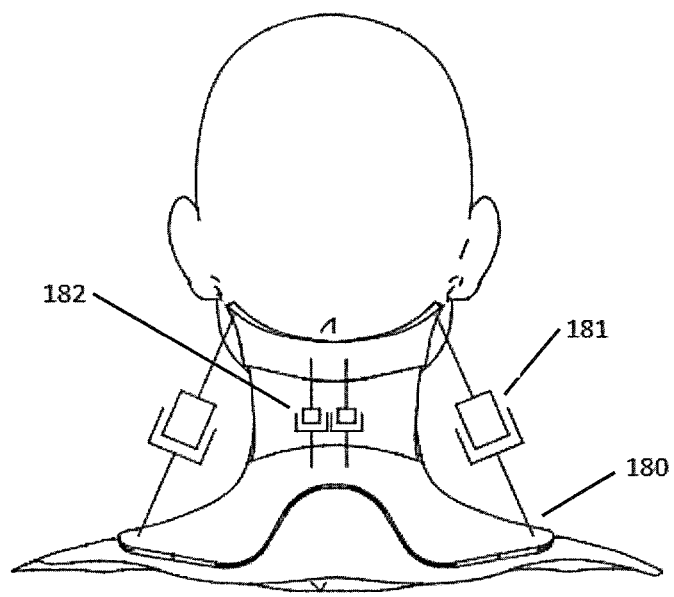
FIG. 63 is a depiction of the neck supporting apparatus with representative dashpots showing the dampening effects.

FIG. 63 illustrates with representative dashpots the dampening effects experienced by the user from the neck supporting apparatus 180. The side dashpots 181 and back dashpots 182, can more generally be referred to as dampers, and can represent either mechanical dampening from the mechanical properties of the physical material, electromechanical damping from electrically active materials, or physiological damping from electrical stimulation of the user's muscles. Mechanical dampening could include oil, grease, stress thickening fluids, magnetic materials, viscoelastic materials or any other type of mechanical dampening previously described or later discovered. Electrical or electromechanical dampening could include ferrofluid resistance, eddy current braking or any other type of electrical resistance previously described or later discovered. Physiological dampening could include electrodes, conductive skin attachments, conductive implants, or any other type of muscle stimulation dampening previously described or later discovered. The side dashpots 181 show dampening provided by the apparatus 180 during lateral motion of the user's head. The back dashpots 182 show dampening provided by the apparatus during a front to back nodding motion of the user's head.

Figure 64A:
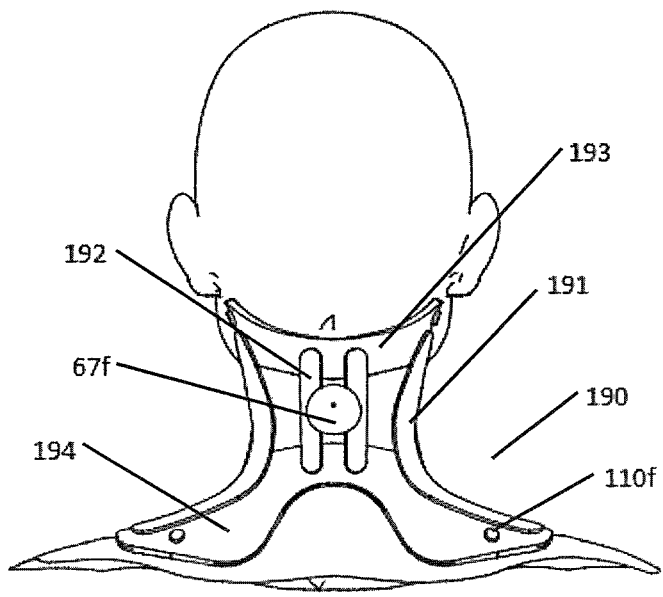
FIGS. 64a-64c depict an embodiment of the neck supporting apparatus containing structural dampening, electrically activated dampers and electrical stimulation.
Figure 64B:
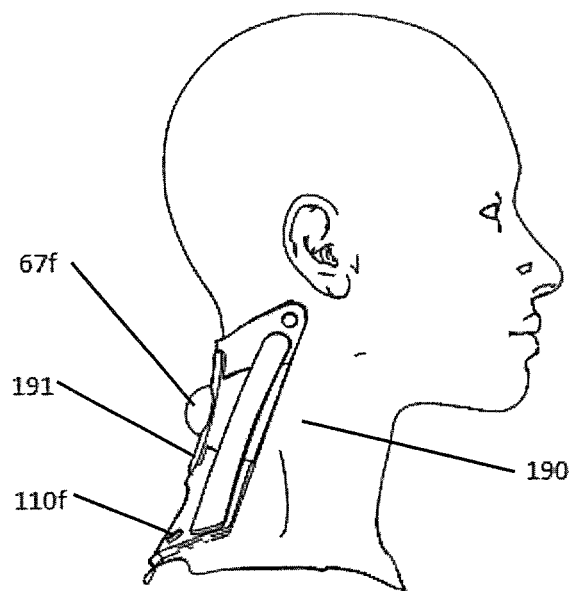
Figure 64C:
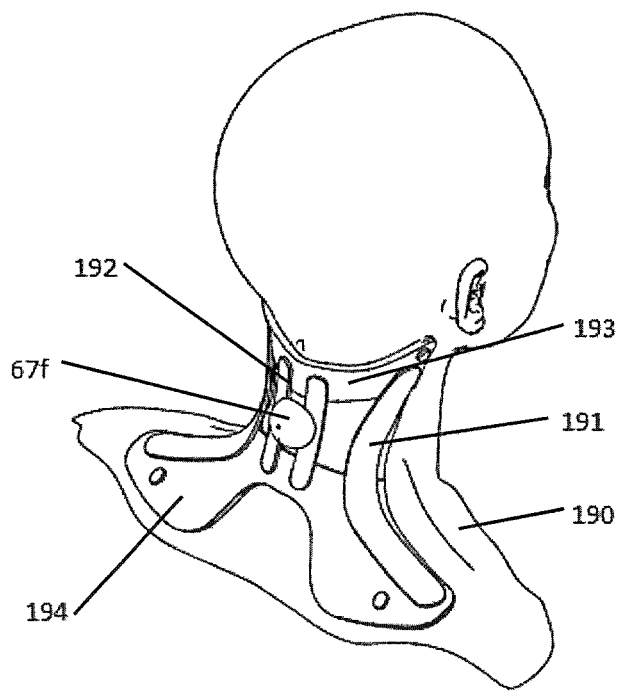

The neck supporting apparatus 190 of FIG. 64a through FIG. 64c depicts a combination of structural dampening, electrically active dampening and EMS described previously. The upper neck or lower head support 193 is coupled to the outer dampers 191 and inner dampers 192. Similarly, the lower neck or upper shoulder support 194 is coupled to the opposing ends of the outer dampers 191 and inner dampers 192. Outer dampers 191 and inner dampers 192 would be designed to provide resistance and dampening under axial elongation, compression, bending, or rotation. The dampening could be created by an interface of high viscosity oil, grease, a shear thickening fluid, or a low durometer elastomer or viscoelastic material in frictional contact of various layers, chambers, or sections making up the damper. For example, the outer dampers 191 and inner dampers 192 could be configured as thin, though relatively inextensible sheets or films that are built up into layers with grease in between each layer. The thin films could be polymer, metal, or any other material that does not easily elongate with the expected forces applied to the damper. Each alternating layer (every other layer) would be connected to the upper neck support 193, and the remaining layers (every other layer that was not connected to the upper neck support 193) would be connected to the lower neck support 194. The layers would be held together and encapsulated with a flexible, extensible membrane. Any bending, elongation, or compression of the dampers would result in in a dynamic shear viscosity relationship between each layer, allowing the damper to bend, or longitudinally move freely at slower speeds with negligible opposing forces, but at higher speeds of bending or longitudinal movement would create resistance to the motion by producing greater opposing forces.

These same dampers 191 and 192 could also be configured to be electrically active (e.g., ferrofluid, eddy current braking) and respond to the speed of elongation, compression, bending or rotation as a function of time. In this case, the control system 67$f$ would continuously monitor the axial elongation of the dampers and provide electrical stimulus to increase or decrease the forces of elongation, compression, rotation, or bending based on the acceleration. This acceleration would be calculated by the control system 67$f$ by dividing the measured movement or motion by the corresponding time twice. The apparatus 190 may also embody electrodes 110$f$ in direct contact with the skin so as to provide electrical muscle stimulation to the muscles in the neck and or shoulders. Contraction of these muscles may further support the head and lessen accelerations in one or multiple directions.

Further anatomical descriptions of the neck supporting apparatus are as follows and can be seen in FIG. 64$a$. An upper U shaped support 193 that runs from just below the mastoid process of the posterior part of the skull across the occipital bone (neck-skull interface) and back up to the opposite mastoid process. There is a larger lower inverted U shaped support 194 that runs from the distal end of the Levator scapulae up across the middle trapezius muscle and back down to the opposite Levator scapulae distal end. There are multiple connective supporting members that attach to both the upper 193 and lower U shaped supports 194. The two outer dampers 191 would be longer and would attach at the end of the upper U shaped support 193 on the mastoid process and the end' of the lower U shaped support 194 on the distal Levator scapulae on the same side. These two members would have the ability to extend or shorten due to a sleeve-like arrangement. The inner dampers 192 connect both U supports at their vertices. The entire apparatus may be encased in a solid breathable membrane layer, not shown, which may have a variety of color options to choose from. This may provide an aesthetic appeal to the user.

Alternatively, the apparatus 190 comprises a curved strip, similar to the upper U support 193 previously described, which may adhere to the neck horizontally, inferior to the base of the skull and superior to spinal vertebrae C3. The lateral ends of the strip would extend from behind one ear, just inferior to the earlobe but superior to the external carotid artery and jugular vein, and dorsal to the carotid artery and jugular vein, but ventral to the spinal column, to the same placement behind the opposing ear. Another curved strip, similar to the inverted U support 194 previously described, may be placed on the top of the shoulders. The two ends of the strip would be positioned just medial to the spine of the scapulae and just superior to the medial end of the spine of the scapulae, and the center of the strip would sit at the midline of the base of the neck between C7 and TI. Inner dampers 192 previously shown, would connect the centers of the upper support 193 to the bottom support 194, and outer dampers 191 would connect the lateral ends of the upper support 193 to the corresponding ends of the lower support 194. The lateral ends of the superior and inferior supports may incorporate EMS electrodes 110$f$, such that each the right and the left side of the device would have a positive terminal on either the superior or inferior strip and a negative terminal on the opposing strip. When the controller 67$f$ detects levels of acceleration over a pre-determined threshold, the EMS would activate the electrodes 110$f$ in order to cause stiffening in the levator scapulae muscles and trapezius muscles to dampen the impact. The device would be flexible and comfortable for users to wear.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub combination or variation of a sub combination.

For example, embodiments of this invention may include means for mitigating the speed or acceleration of the head relative to the torso within a range of motion. Such means encompasses structures such as a damper configured to provide a lower resistance to the motion when the speed or acceleration of the head relative to the torso is lower and a higher resistance to the motion when the speed or acceleration of the head relative to the torso is higher. It also encompasses structures such as a damper configured to provide a lower resistance to the motion when the position of the head relative to the torso is closer to a center of the range of motion and a higher resistance to the motion when the position of the head relative to the torso is closer to extents of the range of motion. The means for mitigating the speed or acceleration of the head relative to the torso also encompasses structures such as the mechanical dampers, physiological dampers and electromechanical dampers described or illustrated herein, as well as structures that are equivalent in one or more of their functionality, performance, and effect.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed is:

1. A method for reducing trauma in the head or neck of a living being caused by acceleration of the head relative to a torso of the living being within a range of motion, the method comprising:
engaging a support with at least one of the head, neck, and shoulder without limiting the range of motion of the head or neck relative to the torso; and
reducing the speed at which the head moves relative to the torso and increasing the time needed for the head to move through the range of motion using a physiological damper including at least one electrode associated with the support.

2. The method of claim 1, wherein the reducing step is performed at least in part by the damper, which provides a lower resistance to the motion when the speed or acceleration of the head relative to the torso is lower and a higher resistance to the motion when the speed or acceleration of the head relative to the torso is higher, thereby reducing the acceleration of the head relative to the torso.

3. The method of claim 1, wherein the reducing step includes stimulating a muscle of at least one of the head, neck, or shoulder.

4. The method of claim 1, wherein the reducing step includes sensing a condition associated with the support.

5. The method of claim 4, wherein sensing includes sensing one or more of position, speed, acceleration, compression, rotation, bending, skin conduction, or cardiovascular physiological parameters associated with the support.

6. The method of claim 1, wherein the reducing step includes the living being responding to a user interface in electrical communication with the support.

7. The method of claim 6, wherein responding includes viewing a graphical display.

8. The method of claim 1, wherein the reducing step includes inhibiting contraction of one or more muscles while contracting one or more different muscles.

9. The method of claim 1, wherein the reducing step includes activating the electrode.

10. The method of claim 1, further comprising sensing a condition associated with the support, and activating the electrode in response to the sensed condition.

11. The method of claim 10, wherein sensing includes sensing one or more of position, speed, acceleration, compression, rotation, bending, skin conduction, or cardiovascular physiological parameters associated with the support.

12. A method for reducing trauma in the head or neck of a living being caused by acceleration of the head relative to a torso of the living being within a range of motion, the method comprising:
engaging a support with at least one of the head, neck, and shoulder without limiting the range of motion of the head or neck relative to the torso; and
strengthening the muscle of the living being as the head moves through the range of motion using a physiological damper including at least one electrode associated with the support.

13. The method of claim 12, wherein the strengthening step includes stimulating a muscle of at least one of the head, neck, or shoulder.

14. The method of claim 12, further comprising using a mechanical damper or an electromechanical damper.

15. The method of claim 12, further comprising increasing the range of motion of the head by increasing flexibility of the living being through extended duration or repeated movements of the head relative to the torso while the support is engaged.

16. The method of claim 12, wherein the strengthening step includes inhibiting contraction of the muscle while contracting one or more different muscles.

17. The method of claim 12, wherein the strengthening step is performed in response to sensing a parameter associated with the support.

18. The method of claim 17, wherein sensing a parameter includes sensing a position, speed, acceleration, compression, rotation, bending, skin conduction, or cardiovascular physiological parameter associated with the support.

19. The method of claim 12, wherein the strengthening step is performed in response to signals transmitted by a user interface in electrical communication with the support.

20. The method of claim 19, wherein the user interface is a graphical display.

21. The method of claim 19, wherein the strengthening step includes sending coordinated signals from the user interface to the support and to the living being to cause the action of the support to dampen or facilitate the movement of the living being as directed by the user interface.

22. The method of claim 19, further comprising the user interface directing the living being to perform movements or remain fixed against actions from the support.

23. The method of claim 17, the sensing step providing feedback to a user interface.

24. A method for reducing trauma in the head or neck of a living being caused by acceleration of the head relative to a torso of the living being within a range of motion, the method comprising:
engaging a support with at least one of the head, neck, and shoulder without limiting the range of motion of the head or neck relative to the torso; and
increasing a muscle contraction speed of the living being as the head moves through the range of motion using a physiological damper including at least one electrode associated with the support.

25. The method of claim 24, wherein the increasing step includes stimulating a muscle of at least one of the head, neck, or shoulder.

26. The method of claim 24, wherein the increasing step is performed in response to sensing a position, speed, acceleration, compression, rotation, bending, skin conduction, or cardiovascular physiological parameters associated with the support.

27. The method of claim 24, wherein the increasing step is performed in response to signals transmitted by a user interface in electrical communication with the support.

28. The method of claim 24, further increasing the range of motion of the head by increasing flexibility of a muscle of the living being through extended duration or repeated movements of the head relative to the torso while the support is engaged.

29. The method of claim 24, the increasing step including inhibiting contraction of one or more muscles while contracting one or more different muscles.

30. The method of claim 27, further comprising increasing a speed of the living being's initiation of movement by repeated responses to communication from the user interface.

31. The method of claim 27, further comprising communicating instructions to the living being using the user interface while simultaneously communicating signals to the support to vary a dampening effect.

32. The method of claim 31, further comprising increasing a rate of reaction of the living being to the instructions of the user interface by repeated communication.

33. The method of claim 27, further comprising increasing a flexibility of a muscle of the living being by repeated or extended duration responses to the user interface.

34. The method of claim 24 further comprising increasing the range of motion of the head relative to the torso through dampening variations of the physiological damper.

35. The method of claim 24, wherein the increasing step includes lowering a physiological electrical threshold of the muscle of the living being.

\* \* \* \* \*